US008507501B2

(12) United States Patent
Yu et al.

(10) Patent No.: US 8,507,501 B2
(45) Date of Patent: Aug. 13, 2013

(54) INHIBITORS OF THE BMP SIGNALING PATHWAY

(75) Inventors: Paul B. Yu, Boston, MA (US); Gregory D. Cuny, Houston, TX (US); Kenneth D. Bloch, Brookline, MA (US); Randall T. Peterson, Belmont, MA (US); Charles C. Hong, Nolensville, TN (US)

(73) Assignees: The Brigham and Women's Hospital, Inc., Boston, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 12/922,122

(22) PCT Filed: Mar. 13, 2009

(86) PCT No.: PCT/US2009/001606
§ 371 (c)(1),
(2), (4) Date: Nov. 17, 2010

(87) PCT Pub. No.: WO2009/114180
PCT Pub. Date: Sep. 17, 2009

(65) Prior Publication Data
US 2011/0053930 A1    Mar. 3, 2011

Related U.S. Application Data

(60) Provisional application No. 61/069,219, filed on Mar. 13, 2008, provisional application No. 61/134,484, filed on Jul. 9, 2008.

(51) Int. Cl.
*A01N 43/90* (2006.01)
*A61K 31/519* (2006.01)
*C07D 487/00* (2006.01)

(52) U.S. Cl.
USPC ........................................ 514/259.3; 544/281

(58) Field of Classification Search
None
See application file for complete search history.

(56) References Cited

U.S. PATENT DOCUMENTS

| 6,235,741 | B1 | 5/2001 | Bilodeau et al. |
| 7,276,525 | B2 | 10/2007 | Miyazono et al. |
| 2002/0041880 | A1 | 4/2002 | DeFeo-Jones et al. |
| 2006/0063208 | A1 | 3/2006 | Woolf et al. |

FOREIGN PATENT DOCUMENTS

| WO | WO-98-52038 A1 | 11/1998 |
| WO | WO98/54093 | * 12/1998 |
| WO | WO-98/54093 A1 | 12/1998 |
| WO | WO-2006-052913 A1 | 5/2006 |
| WO | WO-2007-041712 A1 | 4/2007 |
| WO | WO-2008-033408 A2 | 3/2008 |
| WO | WO-2009-114180 A1 | 9/2009 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Su et al., The transforming growth factor beta 1/SMAD signaling pathway involved in human chronic myeloid leukemia, Tumori, 96:659-666 (2010).
Vogt et al., "The specificities of small molecule inhibitors of the TGFβ and BMP pathways," Cellular Signalling, 23:1831-1842 (2011).
European Search Report for European Application No. EP 10 17 2229 dated Oct. 8, 2010.
Fraley et al., Database Biosis [Online] Biosciences Information Service, "Synthesis and initial SAR studies of 3, 6-disubstituted pyrazolo(1,5-a)pyrimidines: A new class of KDR kinase inhibitors," Database accession No. PREV200200560660 abstract & Bioorganic and Medicinal Chemistry Letters, 12(19):2767-2770 (2002).
Fraley et al., "Optimization of a Pyrazolo[1,5-*a*]pyrimidine Class of KDR Kinase Inhibitors: Improvements in Physical Properties Enhance Cellular Activity and Pharmacokinetics," Bioorganice & Medicinal Chemistry Letters, 12(24):3537-3541 (2002).
Zhou et al., "Role of AMP-activated protein kinase in mechanism of metformin action," Journal of Clinical Investigation, 108(8):1167-1174 (2001).
Cuny et al., "Structure-activity relationship study of bone morphogenetic protein (BMP) signaling inhibitors," *Bioorganic and Medicinal Chemistry Letters*, 18(15):4388-4392 (2008).
Daly et al., "Transforming growth factor beta-induced Smad1/5 phosphorylation in epithelial cells is mediated by novel receptor complexes and is essential for anchorage-independent growth," *Molecular and Cellular Biology,* 28(22):6889-6902 (2008).
Fukuda et al, "A unique mutation of ALK2, G356D, found in a patient with fibrodysplasia ossificans progressiva is a moderately activated BMP type I receptor," *Biochemical and Biophysical Research Communications,* 377(3):905-909 (2008).
Fukuda et al., "Constitutively activated ALK2 and increased SMAD1/5 cooperatively induce bone morphogenetic protein signaling in fibrodysplasia ossificans progressiva," *Journal of Biological Chemistry,* 284(11):7149-7156 (2009).
Hao et al., "Dorsomorphin, a selective small molecule inhibitor of BMP signaling, promotes cardiomyogenesis in embryonic stem cells," *PLoS One,* 3(8):e2904 (2008).
Hong, "Large-scale small-molecule screen using zebrafish embryos," *Methods in Molecular Biology,* 486:43-55 (2009).
International Search Report and Written Opinion mailed Jul. 28, 2009 for PCT/US2009/001606.
International Search Report and Written Opinion mailed Oct. 17, 2008 for PCT/US07/19831.
Lim et al., "Noggin Antagonizes BMP Signaling to Create a Niche for Adult Neurogenesis", Neuron, vol. 28, 713-726, (2000).
Liu et al., "TGFbeta-stimulated Smad1/5 phosphorylation requires the ALK5 L45 loop and mediates the pro-migratory TGFbeta switch," *EMBO Journal,*28(2):88-98 (2009).

(Continued)

*Primary Examiner* — Jeffrey Murray
(74) *Attorney, Agent, or Firm* — Ropes & Gray LLP

(57) ABSTRACT

The present invention provides small molecule inhibitors of BMP signaling. These compounds may be used to modulate cell growth, differentiation, proliferation, and apoptosis, and thus may be useful for treating diseases or conditions associated with BMP signaling, including inflammation, cardiovascular disease, hematological disease, cancer, and bone disorders, as well as for modulating cellular differentiation and/or proliferation.

8 Claims, 24 Drawing Sheets

(56) References Cited

OTHER PUBLICATIONS

Moreno-Miralles et al.., "New insights into bone morphogenetic protein signaling: focus on angiogenesis," *Current Opinion in Hematology*, 16(3):195-201 (2009).

Nam et al., "Compound C inhibits clonal expansion of preadipocytes by increasing p21 level irrespectively of AMPK inhibition," *Archives of Biochemistry and Biophysics*, 479:74-81 (2008).

Niehrs et al., "Dickkofp1 and the Spemann-Mangold Head Organizer," International Journal of Developmental Biology, 45(1):237-240 (2001).

Nishimatsu et al., "Ventral mesoderm induction and patterning by bone morphogenetic protein heterodimers in Xenopus embryos," Mechanism of Development, 74(1-2):75-88 (1998).

Piccolo et al., "Dorsoventral Patterning in Xenopus: Inhibition of Ventral Signals by Direct Binding of Chordin to BMP-4," Cell, 86(23):589-598 (1996).

Re'em-Kalma et al, Competition between noggin and bone morphogenetic protein 4 activities may regulate dorsalization during Xenopus development, Proc. Natl. Acad. Sci. USA, Dec. 1995, vol. 92, pp. 12141-12145, see entire document.

Ross et al., "Twisted gastrulation is a conserved extracellular BMP antagonist," Nature, 410(6827):479-483 (2001).

Sasai et al., "Regulation of Neural Induction by the CHD and BMP-4 Antagonistic Patterning Signals in Xenopus," 376:333-335 (1995).

Seib et al., "Endogenous bone morphogenetic proteins in human bone marrow-derived multipotent mesenchymal stromal cells," *European Journal of Cell Biology*, 88(5):257-271 (2009).

Steinbeisser H. et al, The role of gsc and BMP-4 in dorsal-ventral patterning of the marginal zone in Xenopus: a loss-of-function study using antisense RNA, EMBO Journal, 1995, vol. 14, No. 21, pp. 5230-5243, see entire document.

Supplementary Partial European Search Report dated Oct. 22, 2009 for EP 07 83 8105.

Thomsen, G.H., "Antagonism within and around the organizer: BMP inhibitors in vertebrate body patterning," Trends in Genetics, 13(6):209-211 (1997).

Vucicevic et al., "AMP-activated protein kinase-dependent and -independent mechanisms underlying in vitro antiglioma action of compound C," *Biochemical Pharmacology*, 77(11):1684-1693 (2009).

Wrighton et al., "Transforming Growth Factor {beta} Can Stimulate Smad1 Phosphorylation Independently of Bone Morphogenic Protein Receptors," *Journal of Biological Chemistry*, 284(15):9755-9763 (2009).

Xu, R.H et al, Involvement of Ras/Ra6'AP-1 in BMP-4 signaling during Xenopus embryonic devlopment, Proc. Natl. Acad..Sci. USA, Jan. 1996, vol. 93, pp. 834-838, sec entire document.

Yu et al., "BMP type I receptor inhibition reduces heterotopic [corrected] ossification," Nature Medicine, 14(12):1363-1369 (2008).

Zimmerman et al., "The Spemann Organizer Signal Noggin Binds and Inactivates Bone Morphogenetic Protein 4," Cell, 86(23):599-606 (1996).

Anderson et al., "Small-molecule dissection of BMP signaling," Nature Chemical Biology, 4(1):15-16 (2008).

Yu et al., "Dorsomorphin inhibits BMP signals required for embryogenesis and iron metabolism," Nature Chemical Biology,4(1):33-41 (2007).

Extended European Search Report for European Application No. EP 09 72 0039 dated Jul. 25, 2011.

Hong et al., "Applications of small molecule BMP inhibitors in physiology and disease," Cytokine Growth Factor Rev., 20(5-6):409-418 (2009).

\* cited by examiner

INHIBITORS OF THE BMP SIGNALING PATHWAY

CROSS-REFERENCE TO RELATED APPLICATIONS

This application is a national stage filing under 35 U.S.C. 371 of International Application PCT/US2009/001606, filed Mar. 13, 2009, which claims priority to and benefit of U.S. Provisional Application Nos. 61/069,219, filed Mar. 13, 2008, and 61/134,484, filed Jul. 9, 2008. All the teachings of the above- referenced applications are incorporated herein by reference. International Application PCT/US2009/001606 was published under PCT Article 21 (2) in English.

STATEMENT REGARDING FEDERALLY SPONSORED RESEARCH OR DEVELOPMENT

This invention was supported in part by the United States Government under National Institutes of Health Grants 5R01HL074352, 5K08HL079943, and 5R01HL079267. The Government may have certain rights in this invention.

BACKGROUND OF THE INVENTION

Signaling involving the Transforming Growth Factor β (TGF-β) superfamily of ligands is central to a wide range of cellular processes, including cell growth, differentiation, and apoptosis. TGF-β signaling involves binding of a TGF-β ligand to a type II receptor (a serine/threonine kinase), which recruits and phosphorylates a type I receptor. The type I receptor then phosphorylates a receptor-regulated SMAD (R-SMAD; e.g., SMAD1, SMAD2, SMAD3, SMAD5, SMAD8 or SMAD9), which binds to SMAD4, and the SMAD complex then enters the nucleus where it plays a role in transcriptional regulation. The TGF superfamily of ligands includes two major branches, characterized by TGF-β/activin/nodal and Bone Morphogenetic Proteins (BMPs).

Signals mediated by bone morphogenetic protein (BMP) ligands serve diverse roles throughout the life of vertebrates. During embryogenesis, the dorsoventral axis is established by BMP signaling gradients formed by the coordinated expression of ligands, receptors, co-receptors, and soluble antagonists (Massague et al. *Nat. Rev. Mol. Cell. Biol.* 1:169-178, 2000). Excess BMP signaling causes ventralization, an expansion of ventral at the expense of dorsal structures, while diminished BMP signaling causes dorsalization, an expansion of dorsal at the expense of ventral structures (Nguyen et al. *Dev. Biol.* 199: 93-110, 1998; Furthauer et al. *Dev. Biol.* 214:181-196, 1999; Mintzer et al. *Development* 128:859-869, 2001; Schmid et al. *Development* 127:957-967, 2000). BMPs are key regulators of gastrulation, mesoderm induction, organogenesis, and endochondral bone formation, and regulate the fates of multipotent cell populations (Zhao, *Genesis* 35:43-56, 2003). BMP signals also play critical roles in physiology and disease, and are implicated in primary pulmonary hypertension, hereditary hemorrhagic telangiectasia syndrome, fibrodysplasia ossificans progressiva, and juvenile polyposis syndrome (Waite et al. *Nat. Rev. Genet.* 4:763-773, 2003; Papanikolaou et al. *Nat. Genet.* 36:77-82, 2004; Shore et al. *Nat. Genet.* 38:525-527, 2006).

The BMP signaling family is a diverse subset of the TGF-β superfamily (Sebald et al. *Biol. Chem.* 385:697-710, 2004). Over twenty known BMP ligands are recognized by three distinct type II (BMPRII, ActRIIa, and ActRIIb) and at least three type I (ALK2, ALK3, and ALK6) receptors. Dimeric ligands facilitate assembly of receptor heteromers, allowing the constitutively-active type II receptor serine/threonine kinases to phosphorylate type I receptor serine/threonine kinases. Activated type I receptors phosphorylate BMP-responsive (BR-) SMAD effectors (SMADs 1, 5, and 8) to facilitate nuclear translocation in complex with SMAD4, a co-SMAD that also facilitates TGF signaling. In addition, BMP signals can activate intracellular effectors such as MAPK p38 in a SMAD-independent manner (Nohe et al. *Cell Signal* 16:291-299, 2004). Soluble BMP antagonists such as noggin, chordin, gremlin, and follistatin limit BMP signaling by ligand sequestration.

A role for BMP signals in regulating expression of hepcidin, a peptide hormone and central regulator of systemic iron balance, has also been suggested (Pigeon et al. *J. Biol. Chem.* 276:7811-7819, 2001; Fraenkel et al. *J. Clin. Invest.* 115: 1532-1541, 2005; Nicolas et al. *Proc. Natl. Acad. Sci. U.S.A.* 99:4596-4601, 2002; Nicolas et al. *Nat. Genet.* 34:97-101, 2003). Hepcidin binds and promotes degradation of ferroportin, the sole iron exporter in vertebrates. Loss of ferroportin activity prevents mobilization of iron to the bloodstream from intracellular stores in enterocytes, macrophages, and hepatocytes (Nemeth et al. *Science* 306:2090-2093, 2004). The link between BMP signaling and iron metabolism represents a potential target for therapeutics.

Given the tremendous structural diversity of the BMP and TGF-β superfamily at the level of ligands (>25 distinct ligands at present) and receptors (three type I and three type II receptors that recognize BMPs), and the heterotetrameric manner of receptor binding, traditional approaches for inhibiting BMP signals via soluble receptors, endogenous inhibitors, or neutralizing antibodies are not practical or effective. Endogenous inhibitors such as noggin and follistatin have limited specificity for ligand subclasses. Single receptors have limited affinity for ligand, whereas ligand heterotetramers exhibit rather precise specificity for particular ligands. Neutralizing antibodies are specific for particular ligands or receptors and are also limited by the structural diversity of this signaling system. Thus, there is a need in the art for pharmacologic agents that specifically antagonize BMP signaling pathways and that can be used to manipulate these pathways in therapeutic or experimental applications, such as those listed above.

SUMMARY OF THE INVENTION

In one aspect, the invention provides compounds that inhibit BMP-induced phosphorylation of SMAD1/5/8 including compounds represented by general formula I:

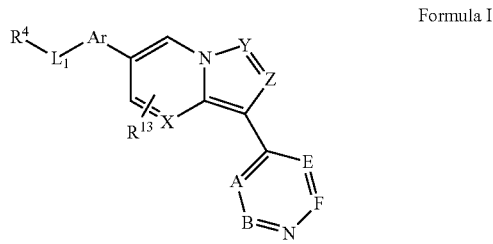

Formula I wherein
X is selected from $CR^{15}$ and N;
Y is selected from $CR^{15}$ and N;
Z is selected from $CR^3$ and N;
Ar is selected from substituted or unsubstituted aryl and heteroaryl, e.g., a six-membered ring, such as phenyl;

$L_1$ is absent or selected from substituted or unsubstituted alkyl and heteroalkyl;

A and B, independently for each occurrence, are selected from $CR^{16}$ and N, preferably $CR^{16}$, e.g., CH;

E and F, independently for each occurrence, are selected from $CR^5$ and N, preferably $CR^5$;

preferably chosen such that no more than two of A, B, E, and F are N;

$R^3$ represents a substituent, e.g., selected from H and substituted or unsubstituted alkyl, heteroalkyl, cycloalkyl, halogen, hydroxyl, alkoxyl, alkylthio, acyloxy, acylamino, carbamate, cyano, sulfonyl, sulfoxido, sulfamoyl, or sulfonamido, e.g., lower alkyl;

$R^4$ is selected from substituted or unsubstituted alkyl, alkenyl, alkynyl, heteroalkyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido, e.g., substituted or unsubstituted alkenyl, alkynyl, cycloalkyl, heterocyclyl, aryl, heteroaryl, acyl, carboxyl, ester, acyloxy, amino, acylamino, carbamate, amido, amidino, sulfonyl, sulfoxido, sulfamoyl, or sulfonamido, preferably substituted or unsubstituted heterocyclyl or heteroaryl;

$R^5$, independently for each occurrence, represents a substituent, e.g., selected from H and substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano), or two occurrences of $R^5$ taken together with the atoms to which they are attached form a substituted or unsubstituted 5- or 6-membered cycloalkyl, heterocycloalkyl, aryl, or heteroaryl ring, preferably an aryl or heteroaryl ring, e.g., a substituted or unsubstituted benzo ring;

$R^{13}$ is absent or represents 1-2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido, preferably substituted or unsubstituted alkyl, heteroalkyl, halogen, hydroxyl, alkoxyl, alkylthio, acyloxy, acylamino, carbamate, or cyano;

$R^{15}$, independently for each occurrence, represents a substituent, e.g., selected from H and substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido, preferably H or substituted or unsubstituted alkyl, heteroalkyl, halogen, hydroxyl, alkoxyl, alkylthio, acyloxy, acylamino, carbamate, or cyano;

$R^{16}$, independently for each occurrence, represents a substituent, e.g., selected from H and substituted or unsubstituted alkyl, alkenyl, alkynyl, heteroalkyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido, preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, or cyano, or a pharmaceutically acceptable salt, ester, or prodrug thereof.

In certain embodiments, either Y is N or Ar comprises a nitrogen atom in the ring.

In certain embodiments, E and F are each $CR^5$, and both instances of $R^5$ together with the intervening atoms form a 5-, 6-, or 7-membered ring optionally substituted by substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano). In certain embodiments, E and F together form a substituted or unsubstituted 6-membered cycloalkyl, heterocyclyl, aryl or heteroaryl ring (e.g., a pyridine, piperidine, pyran, or piperazine ring, etc.). In certain such embodiments, the ring comprises one to four amine groups, while in other embodiments, the ring is a substituted or unsubstituted benzo ring (e.g.,

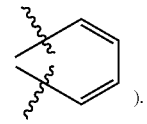
).

In certain such embodiments, the ring is substituted, e.g., by optionally substituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, Ar represents substituted or unsubstituted heteroaryl e.g., pyrrole, furan, thiophene, imidazole, oxazole, thiazole, pyrazole, pyridine, pyrazine, pyridazine, quinoline, and pyrimidine, In certain embodiments, Ar represents substituted or unsubstituted aryl, such as phenyl. In certain embodiments, Ar is a 6-membered ring, such as a phenyl ring, e.g., in which $L_1$ is disposed on the para-position of Ar relative to the bicyclic core.

In certain embodiments as discussed above, substituents on Ar are selected from substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, $L_1$ represents a linker $M_k$, wherein k is an integer from 1-8, preferably from 2-4, and each M represents a unit selected from $C(R^{18})_2$, $NR^{19}$, S, $SO_2$, or O, preferably selected so that no two heteroatoms occur in adjacent positions, more preferably with at least two carbon atoms between any nitrogen atom and another heteroatom; wherein $R^{18}$, independently for each occurrence, is selected from H and substituted or unsubstituted alkyl, heteroalkyl, cycloalkyl, heterocyclyl, cycloalkylalkyl, heterocyclylalkyl, hydroxyl, alkoxyl, alkylthio, acyloxy, amino, acylamino, carbamate, amido, amidino, cyano, sulfonyl, sulfoxido, sulfamoyl, or sulfonamido, preferably H or lower alkyl; and $R^{19}$ is selected from H and substituted or unsubstituted alkyl, cycloalkyl, heterocyclyl, heterocyclylalkyl, oxide, amino, acylamino, carbamate, amido, amidino, sulfonyl, sulfamoyl, or sulfonamido, preferably H or lower alkyl.

In certain embodiments, $L_1$ is absent. In certain embodiments, $L_1$ is selected from substituted or unsubstituted alkyl (e.g., $C_1$-$C_8$ chains, preferably $C_2$-$C_4$ chains) and heteroalkyl. In certain such embodiments, $L_1$ has a structure

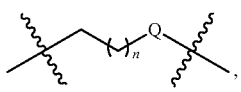

wherein n is an integer from 0 to 4, and Q is selected from $CR^{10}R^{11}$, $NR^{12}$, O, S, S(O), and $SO_2$; $R^{10}$ and $R^{11}$, independently for each occurrence, are selected from H and substituted or unsubstituted alkyl, heteroalkyl, cycloalkyl, heterocyclyl, cycloalkylalkyl, heterocyclylalkyl, hydroxyl, alkoxyl, alkylthio, acyloxy, amino, acylamino, carbamate, amido, amidino, cyano, sulfonyl, sulfoxido, sulfamoyl, or sulfonamido, preferably H or lower alkyl; and $R^{12}$ is selected from H and substituted or unsubstituted alkyl, cycloalkyl, heterocyclyl, heterocyclylalkyl, oxide, amino, acylamino, carbamate, amido, amidino, sulfonyl, sulfamoyl, or sulfonamido, preferably H or lower alkyl. In certain embodiments, $L_1$ has a structure

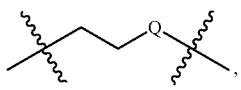

wherein Q is $CH_2$, NH, S, $SO_2$, or O, preferably O.

In certain embodiments, $R^4$ is

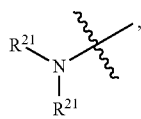

wherein $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamido, preferably H or lower alkyl.

In certain embodiments, $R^4$ is heterocyclyl, e.g., comprising one or two heteroatoms, such as N, S or O (e.g., piperidine, piperazine, pyrrolidine, morpholine, lactone, or lactam). In certain such embodiments, $R^4$ is heterocyclyl comprising one nitrogen atom, e.g., piperidine or pyrrolidine, such as

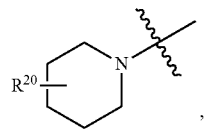

wherein $R^{20}$ is absent or represents from 1-4 substituents on the ring to which it is attached, e.g., selected from substituted or unsubstituted alkyl, heteroaryl, aralkyl, cycloalkyl, heterocyclyl, aryl, heteroaryl, heteroaralkyl, cycloalkylalkyl, heterocyclylalkyl, acyl, hydroxyl, alkoxyl, alkylthio, acyloxy, sulfonyl, sulfoxido, sulfamoyl, and sulfonamido, preferably H or lower alkyl. In certain embodiments, $R^4$ is heterocyclyl comprising two nitrogen atoms, e.g., piperazine. In certain embodiments, $R^4$ is heterocyclyl comprising a nitrogen and an oxygen atom, e.g., morpholine.

In certain embodiments, $R^4$ is a heterocyclyl or heteroaryl that includes an amine within the atoms of the ring, e.g., pyridyl, imidazolyl, pyrrolyl, piperidyl, pyrrolidyl, piperazyl, oxazolyl, isoxazolyl, thiazolyl, etc., and/or bears an amino substituent. In certain embodiments, $R^4$ is

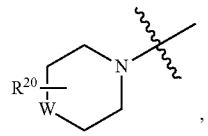

wherein $R^{20}$ is as defined above; W represents a bond or is selected from $C(R^{21})_2$, O, or $NR^{21}$; and $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamido, preferably H or lower alkyl.

In certain preferred embodiments, $L_1$ is absent and Ar—$R^4$ has a structure

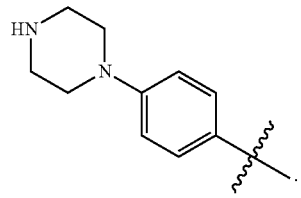 [SMILES: *c1ccc(N2CCNCC2)cc1]

In certain embodiments as discussed above, substituents on $R^4$ are selected from substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, $L_1$ is absent and $R^4$ is directly attached to Ar. In embodiments wherein $R^4$ is a six-membered ring directly attached to Ar and bears an amino substituent at the 4-position of the ring relative to N.

In certain embodiments, $L_1$-$R^4$ comprises a basic nitrogen-containing group, e.g., either $L_1$ comprises nitrogen-containing heteroalkyl or an amine-substituted alkyl, or $R^4$ comprises a substituted or unsubstituted nitrogen-containing heterocyclyl or heteroaryl and/or is substituted with an amine substituent. In certain such embodiments, the $pK_a$ of the conjugate acid of the basic nitrogen-containing group is 6 or higher, or even 8 or higher.

In certain embodiments, $L_1$ has a structure

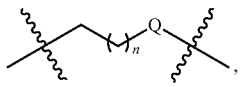

wherein n is an integer from 0 to 4, and $R^4$ is heterocyclyl. In certain such embodiments, E and F together form a ring, e.g., a benzo ring, while in other embodiments, E and F do not form a ring.

In certain embodiments, $L_1$ is absent and $R^4$ is heterocyclyl, especially a nitrogen-containing heterocyclyl. In certain such embodiments, E and F together form a ring, e.g., a benzo ring, while in other embodiments, E and F do not form a ring. In certain embodiments, $L_1$ is absent and $R^4$ is piperidine, piperazine, pyrrolidine, or morpholine.

In certain of the embodiments disclosed above, if $L_1$ is alkyl or heteroalkyl and $R^4$ is heterocyclyl, especially a nitrogen-containing heterocyclyl, then E and F together form a ring, e.g., a benzo ring. In certain of the embodiments disclosed above, if $L_1$ has a structure

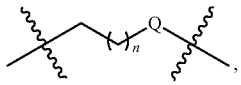

wherein n is an integer from 0 to 4 (especially from 1-2) and Q is S or O, then E and F together form a ring, e.g., a benzo ring.

In certain embodiments, either E and F are both $CR^5$ and both occurrences of $R^5$ taken together with E and F form a ring, e.g., a benzo ring, or $L_1$ is absent. In certain such embodiments, $R^4$ is selected from substituted or unsubstituted alkenyl, alkynyl, cycloalkyl, heterocyclyl, aryl, heteroaryl, acyl, carboxyl, ester, acyloxy, amino, acylamino, carbamate, amido, amidino, sulfonyl, sulfoxido, sulfamoyl, and sulfonamido. In certain embodiments, either E and F are both $CR^5$ and both occurrences of $R^5$ taken together with E and F form a ring, e.g., a benzo ring, or $R^4$ is selected from substituted or unsubstituted cycloalkyl, aryl, heteroaryl, acyl, carboxyl, ester, acyloxy, amino, acylamino, carbamate, amido, amidino, sulfonyl, sulfoxido, sulfamoyl, and sulfonamido.

In certain of the embodiments disclosed above, if $L_1$ is absent, $R^4$ is cycloalkyl or heterocyclyl (e.g., a nitrogen-containing heterocycle, such as piperidine, piperazine, pyrrolidine, morpholine, etc.).

In certain of the embodiments disclosed above, if $L_1$ is heteroalkyl and $R^4$ is heterocyclyl (especially a nitrogen-containing heterocycle), then Y is $CR^{15}$, wherein $R^{15}$ is as defined above. In certain of the embodiments disclosed above, if $L_1$ is heteroalkyl and $R^4$ is piperidine, then Y is $CR^{15}$, wherein $R^{15}$ is as defined above. In certain embodiments wherein Y is $CR^{15}$, $R^{15}$ is selected from H, lower alkyl, heteroalkyl, and ester (e.g., lower alkyl ester, such as methyl ester).

In certain of the embodiments disclosed above, if $L_1$ is heteroalkyl and $R^4$ is heterocyclyl (especially nitrogen-containing heterocyclyl), then X is $CR^{15}$, wherein $R^{15}$ is as defined above. In certain of the embodiments disclosed above, if $L_1$ is heteroalkyl and $R^4$ is piperidine, then X is $CR^{15}$, wherein $R^{15}$ is as defined above. In certain embodiments wherein X is $R^{15}$, $R^{15}$ is selected from H, lower alkyl, and heteroalkyl.

In certain of the embodiments disclosed above, if $L_1$ is heteroalkyl and $R^4$ is heterocyclyl (especially nitrogen-containing heterocyclyl), then Z is $CR^3$, wherein $R^3$ is as defined above. In certain of the embodiments disclosed above, if $L_1$ is heteroalkyl and $R^4$ is piperidine, then Z is $CR^3$, wherein $R^3$ is as defined above. In certain embodiments wherein Z is $CR^3$, $R^3$ is selected from H, lower alkyl, and heteroalkyl.

In certain of the embodiments disclosed above, if $L_1$ is heteroalkyl and $R^4$ is heterocyclyl (especially a nitrogen-containing heterocycle, such as piperidine), $R^{13}$ represents 2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido.

In certain of the embodiments disclosed above, if $L_1$ is heteroalkyl and $R^4$ is heterocyclyl (especially a nitrogen-containing heterocycle, such as piperidine), Ar represents substituted or unsubstituted heteroaryl (e.g., pyrrole, furan, thiophene, imidazole, oxazole, thiazole, pyrazole, pyridine, pyrazine, pyridazine, quinoline, and pyrimidine). In certain such embodiments, Ar is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.

In certain of the embodiments disclosed above, if $L_1$ is heteroalkyl and $R^4$ is heterocyclyl (e.g., piperidine, piperazine, pyrrolidine, morpholine, lactones, lactams, and the like), $R^4$ is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.

In certain of the embodiments disclosed above, compounds have one or more of the following features:
either Y is N or Ar comprises a nitrogen atom in the ring;
$L_1$ is absent;
E and F together form a ring;
$R^4$ is cycloalkyl, aryl, or heteroaryl;
X is $CR^{15}$;
Y is $CR^{15}$;
Z is $CR^3$;
$R^{13}$ represents 1-2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido;
Ar represents substituted or unsubstituted heteroaryl (e.g., pyrrole, furan, thiophene, imidazole, oxazole, thiazole, pyrazole, pyridine, pyrazine, pyridazine, quinoline, and pyrimidine);

Ar is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido; and $R^4$ is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.

In one aspect, the invention provides compounds that inhibit BMP-induced phosphorylation of SMAD1/5/8 including compounds represented by general formula II:

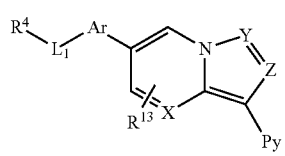

Formula II wherein
- X is selected from $CR^{15}$ and N;
- Y is selected from $CR^{15}$ and N;
- Z is selected from $CR^3$ and N;
- Ar is selected from substituted or unsubstituted aryl and heteroaryl, e.g., a six-membered ring, such as phenyl;
- $L_1$ is absent or selected from substituted or unsubstituted alkyl and heteroalkyl;
- Py is substituted or unsubstituted 4-pyridinyl or 4-quinolinyl, e.g., optionally substituted with substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, halogen, acyl, carboxyl, ester, amino, acylamino, carbamate, amido, amidino, cyano, sulfonyl, sulfoxido, sulfamoyl, or sulfonamido; and
- $R^3$ represents a substituent, e.g., selected from H and substituted or unsubstituted alkyl, heteroalkyl, cycloalkyl, halogen, hydroxyl, alkoxyl, alkylthio, acyloxy, acylamino, carbamate, cyano, sulfonyl, sulfoxido, sulfamoyl, or sulfonamido, e.g., lower alkyl;
- $R^4$ is selected from substituted or unsubstituted alkyl, alkenyl, alkynyl, heteroalkyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido, e.g., substituted or unsubstituted alkenyl, alkynyl, cycloalkyl, heterocyclyl, aryl, heteroaryl, acyl, carboxyl, ester, acyloxy, amino, acylamino, carbamate, amido, amidino, sulfonyl, sulfoxido, sulfamoyl, or sulfonamido, preferably substituted or unsubstituted heterocyclyl or heteroaryl;
- $R^5$, independently for each occurrence, represents a substituent, e.g., selected from H and substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano), or two occurrences of $R^3$ taken together with the atoms to which they are attached form a substituted or unsubstituted 5- or 6-membered cycloalkyl, heterocycloalkyl, aryl, or heteroaryl ring, preferably an aryl or heteroaryl ring, e.g., a substituted or unsubstituted benzo ring;
- $R^{13}$ is absent or represents 1-2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido, preferably substituted or unsubstituted alkyl, heteroalkyl, halogen, hydroxyl, alkoxyl, alkylthio, acyloxy, acylamino, carbamate, or cyano;
- $R^{15}$, independently for each occurrence, represents a substituent, e.g., selected from H and substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido, preferably H or substituted or unsubstituted alkyl, heteroalkyl, halogen, hydroxyl, alkoxyl, alkylthio, acyloxy, acylamino, carbamate, or cyano;
- $R^{16}$, independently for each occurrence, represents a substituent, e.g., selected from H and substituted or unsubstituted alkyl, alkenyl, alkynyl, heteroalkyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido, preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, or cyano, or a pharmaceutically acceptable salt, ester, or prodrug thereof.

In certain embodiments, either Y is N or Ar comprises a nitrogen atom in the ring.

In certain embodiments, Py is substituted by substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, Ar represents substituted or unsubstituted heteroaryl e.g., pyrrole, furan, thiophene, imidazole, oxazole, thiazole, pyrazole, pyridine, pyrazine, pyridazine, quinoline, and pyrimidine. In certain embodiments, Ar represents substituted or unsubstituted aryl, such as phenyl. In certain embodiments, Ar is a 6-membered ring, such as a phenyl ring, e.g., in which $L_1$ is disposed on the para-position of Ar relative to the bicyclic core.

In certain embodiments as discussed above, substituents on Ar are selected from substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, $L_a$ represents a linker $M_k$, wherein k is an integer from 1-8, preferably from 2-4, and each M represents a unit selected from $C(R^{18})_2$, $NR^{19}$, S, $SO_2$, or O, preferably selected so that no two heteroatoms occur in adjacent positions, more preferably with at least two carbon atoms between any nitrogen atom and another heteroatom; wherein $R^{18}$, independently for each occurrence, is selected from H and substituted or unsubstituted alkyl, heteroalkyl, cycloalkyl, heterocyclyl, cycloalkylalkyl, heterocyclylalkyl, hydroxyl, alkoxyl, alkylthio, acyloxy, amino, acylamino, carbamate, amido, amidino, cyano, sulfonyl, sulfoxido, sulfamoyl, or sulfonamido, preferably H or lower alkyl; and $R^{19}$ is selected from H and substituted or unsubstituted alkyl, cycloalkyl, heterocyclyl, heterocyclylalkyl, oxide, amino, acylamino, carbamate, amido, amidino, sulfonyl, sulfamoyl, or sulfonamido, preferably H or lower alkyl.

In certain embodiments, $L_1$ is absent. In certain embodiments, $L_1$ is selected from substituted or unsubstituted alkyl (e.g., $C_1$-$C_8$ chains, preferably $C_2$-$C_4$ chains) and heteroalkyl. In certain such embodiments, $L_1$ has a structure

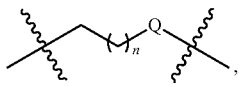

wherein n is an integer from 0 to 4, and Q is selected from $CR^{10}R^{11}$, $NR^{12}$, O, S, S(O), and $SO_2$; $R^{10}$ and $R^{11}$, independently for each occurrence, are selected from H and substituted or unsubstituted alkyl, heteroalkyl, cycloalkyl, heterocyclyl, cycloalkylalkyl, heterocyclylalkyl, hydroxyl, alkoxyl, alkylthio, acyloxy, amino, acylamino, carbamate, amido, amidino, cyano, sulfonyl, sulfoxido, sulfamoyl, or sulfonamido, preferably H or lower alkyl; and $R^{12}$ is selected from H and substituted or unsubstituted alkyl, cycloalkyl, heterocyclyl, heterocyclylalkyl, oxide, amino, acylamino, carbamate, amido, amidino, sulfonyl, sulfamoyl, or sulfonamido, preferably H or lower alkyl. In certain embodiments, $L_1$ has a structure

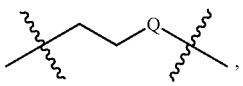

wherein Q is $CH_2$, NH, S, $SO_2$, or O, preferably O.

In certain embodiments, $R^4$ is

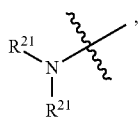

wherein $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamido, preferably H or lower alkyl.

In certain embodiments, $R^4$ is heterocyclyl, e.g., comprising one or two heteroatoms, such as N, S or O (e.g., piperidine, piperazine, pyrrolidine, morpholine, lactone, or lactam). In certain such embodiments, $R^4$ is heterocyclyl comprising one nitrogen atom, e.g., piperidine or pyrrolidine, such as

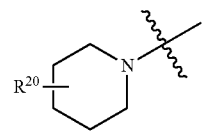

wherein $R^{20}$ is absent or represents from 1-4 substituents on the ring to which it is attached, e.g., selected from substituted or unsubstituted alkyl, heteroaryl, aralkyl, cycloalkyl, heterocyclyl, aryl, heteroaryl, heteroaralkyl, cycloalkylalkyl, heterocyclylalkyl, acyl, hydroxyl, alkoxyl, alkylthio, acyloxy, sulfonyl, sulfoxido, sulfamoyl, and sulfonamido, preferably H or lower alkyl. In certain embodiments, $R^4$ is heterocyclyl comprising two nitrogen atoms, e.g., piperazine. In certain embodiments, $R^4$ is heterocyclyl comprising a nitrogen and an oxygen atom, e.g., morpholine.

In certain embodiments, $R^4$ is a heterocyclyl or heteroaryl that includes an amine within the atoms of the ring, e.g., pyridyl, imidazolyl, pyrrolyl, piperidyl, pyrrolidyl, piperazyl, oxazolyl, isoxazolyl, thiazolyl, etc., and/or bears an amino substituent. In certain embodiments, $R^4$ is

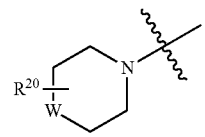

wherein $R^{20}$ is as defined above; W represents a bond or is selected from $C(R^{21})_2$, O, or $NR^{21}$; and $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamido, preferably H or lower alkyl.

In certain embodiments as discussed above, substituents on $R^4$ are selected from substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, $L_1$ is absent and $R^4$ is directly attached to Ar. In embodiments wherein $R^4$ is a six-membered ring directly attached to Ar and bears an amino substituent at the 4-position of the ring relative to N, the N and amine substituents may be disposed trans on the ring.

In certain embodiments, $L_1$-$R^4$ comprises a basic nitrogen-containing group, e.g., either $L_1$ comprises nitrogen-containing heteroalkyl or an amine-substituted alkyl, or $R^4$ comprises a substituted or unsubstituted nitrogen-containing heterocyclyl or heteroaryl and/or is substituted with an amine substituent. In certain such embodiments, the $pK_a$ of the conjugate acid of the basic nitrogen-containing group is 6 or higher, or even 8 or higher.

In certain embodiments, $L_1$ has a structure

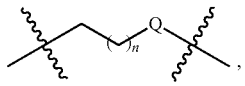

wherein n is an integer from 0 to 4, and $R^4$ is heterocyclyl. In certain such embodiments, Py is 4-quinolinyl, while in other embodiments, Py is 4-pyridinyl.

In certain embodiments, $L_1$ is absent and $R^4$ is heterocyclyl, especially a nitrogen-containing heterocyclyl. In certain such embodiments, Py is 4-quinolinyl, while in other embodiments, Py is 4-pyridinyl. In certain embodiments, $L_1$ is absent and $R^4$ is piperidine, piperazine, pyrrolidine, or morpholine.

In certain of the embodiments disclosed above, if $L_1$ is alkyl or heteroalkyl and $R^4$ is heterocyclyl, especially a nitrogen-containing heterocyclyl, then Py is 4-quinolinyl. In certain of the embodiments disclosed above, if $L_1$ has a structure

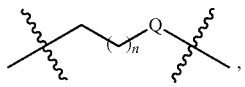

wherein n is an integer from 0 to 4 (especially from 1-2) and Q is S or O, then Py is 4-quinolinyl.

In certain embodiments, either Py is 4-quinolinyl, or $L_1$ is absent. In certain such embodiments, $R^4$ is selected from substituted or unsubstituted alkenyl, alkynyl, cycloalkyl, heterocyclyl, aryl, heteroaryl, acyl, carboxyl, ester, acyloxy, amino, acylamino, carbamate, amido, amidino, sulfonyl, sulfoxido, sulfamoyl, and sulfonamido. In certain embodiments, either Py is 4-quinolinyl, or $R^4$ is selected from substituted or unsubstituted cycloalkyl, aryl, heteroaryl, acyl, carboxyl, ester, acyloxy, amino, acylamino, carbamate, amido, amidino, sulfonyl, sulfoxido, sulfamoyl, and sulfonamido.

In certain of the embodiments disclosed above, if $L_1$ is absent, $R^4$ is cycloalkyl or heterocyclyl (e.g., a nitrogen-containing heterocycle, such as piperidine, piperazine, pyrrolidine, morpholine, etc.).

In certain of the embodiments disclosed above, if $L_1$ is heteroalkyl and $R^4$ is heterocyclyl (especially a nitrogen-containing heterocycle), then Y is $CR^{15}$, wherein $R^{15}$ is as defined above. In certain of the embodiments disclosed above, if $L_1$ is heteroalkyl and $R^4$ is piperidine, then Y is $CR^{15}$, wherein $R^{15}$ is as defined above. In certain embodiments wherein Y is $CR^{15}$, $R^{15}$, is selected from H, lower alkyl, heteroalkyl, and ester (e.g., lower alkyl ester, such as methyl ester).

In certain of the embodiments disclosed above, if $L_1$ is heteroalkyl and $R^4$ is heterocyclyl (especially nitrogen-containing heterocyclyl), then X is $CR^{15}$, wherein $R^{15}$ is as defined above. In certain of the embodiments disclosed above, if $L_1$ is heteroalkyl and $R^4$ is piperidine, then X is $CR^{15}$, wherein $R^{15}$ is as defined above. In certain embodiments wherein X is $R^{15}$, $R^{15}$ is selected from H, lower alkyl, and heteroalkyl.

In certain of the embodiments disclosed above, if $L_1$ is heteroalkyl and $R^4$ is heterocyclyl (especially nitrogen-containing heterocyclyl), Z is $CR^3$, wherein $R^3$ is as defined above. In certain of the embodiments disclosed above, if $L_1$ is heteroalkyl and $R^4$ is piperidine, then Z is $CR^3$, wherein $R^3$ is as defined above. In certain embodiments wherein Z is $CR^3$, $R^3$ is selected from H, lower alkyl, and heteroalkyl.

In certain of the embodiments disclosed above, if $L_1$ is heteroalkyl and $R^4$ is heterocyclyl (especially a nitrogen-containing heterocycle, such as piperidine), $R^{13}$ represents 2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido.

In certain of the embodiments disclosed above, if $L_1$ is heteroalkyl and $R^4$ is heterocyclyl (especially a nitrogen-containing heterocycle, such as piperidine), Ar represents substituted or unsubstituted heteroaryl (e.g., pyrrole, furan, thiophene, imidazole, oxazole, thiazole, pyrazole, pyridine, pyrazine, pyridazine, quinoline, and pyrimidine). In certain such embodiments, Ar is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.

In certain of the embodiments disclosed above, if $L_1$ is heteroalkyl and $R^4$ is heterocyclyl (e.g., piperidine, piperazine, pyrrolidine, morpholine, lactones, lactams, and the like), $R^4$ is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.

In certain of the embodiments disclosed above, compounds have one or more of the following features:
either Y is N or Ar comprises a nitrogen atom in the ring;
$L_1$ is absent;
Py is 4-quinolinyl;
$R^4$ is cycloalkyl, aryl, or heteroaryl;
X is $CR^{15}$;
Y is $CR^{15}$;
Z is $CR^3$;
$R^{13}$ represents 1-2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido;
Ar represents substituted or unsubstituted heteroaryl (e.g., pyrrole, furan, thiophene, imidazole, oxazole, thiazole, pyrazole, pyridine, pyrazine, pyridazine, quinoline, and pyrimidine);
Ar is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido; and
$R^4$ is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.
Exemplary compounds of Formula I and Formula II include:
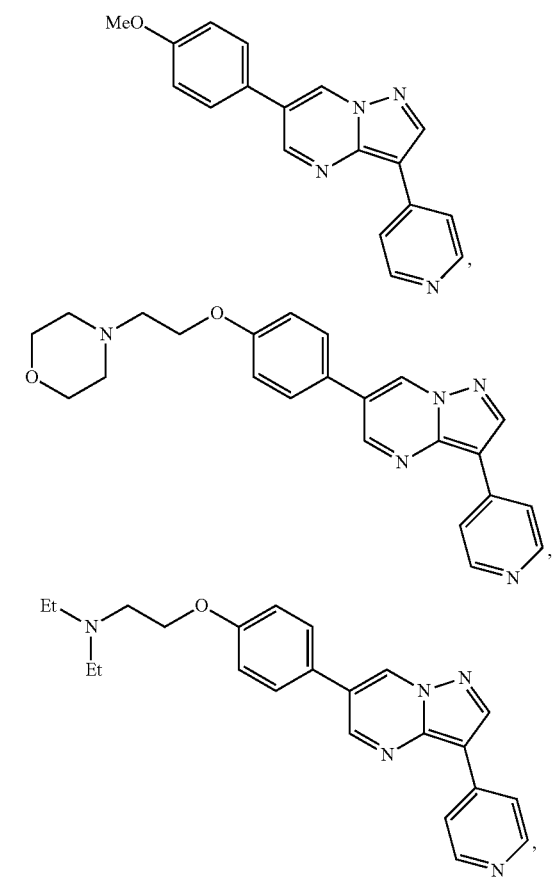
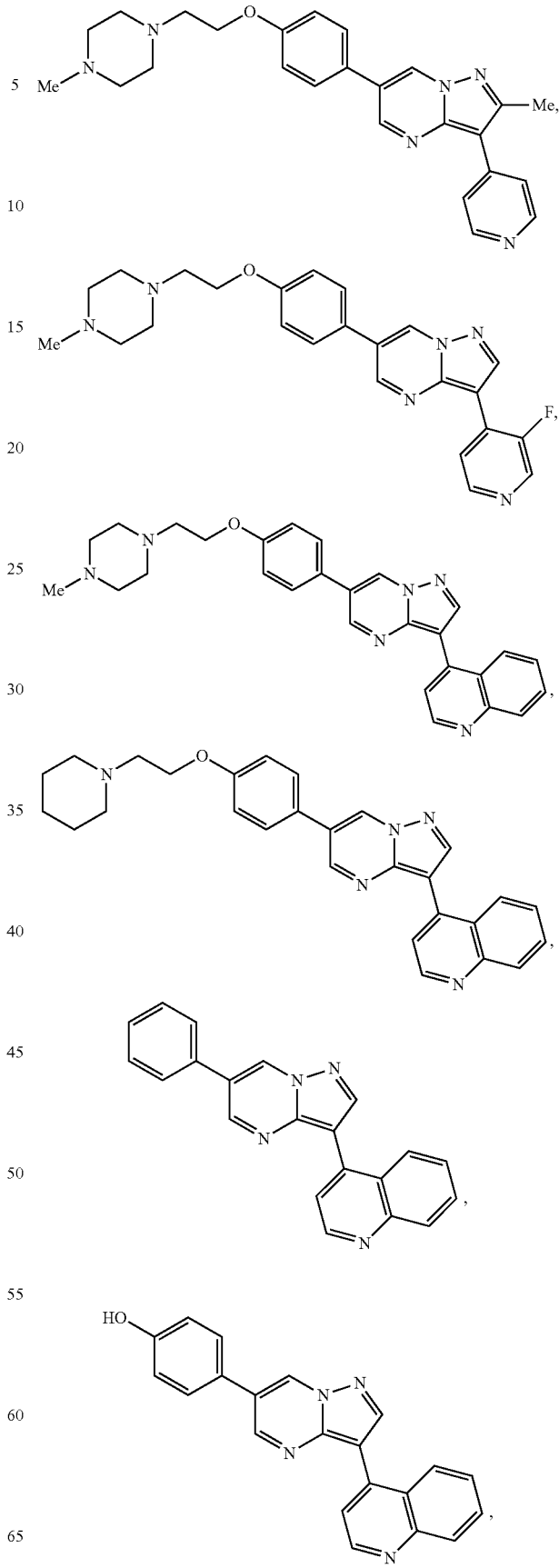

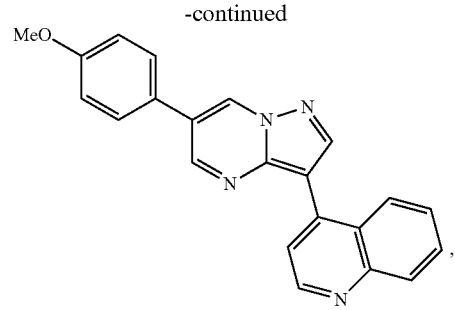
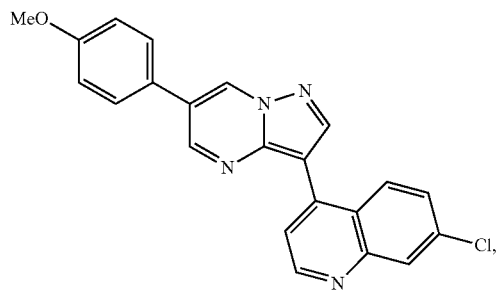
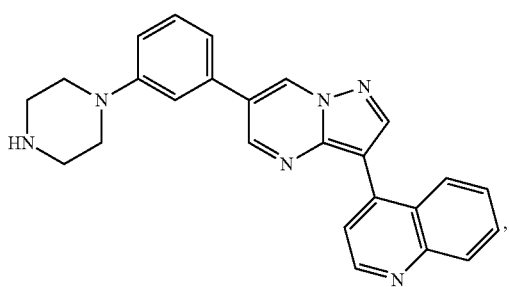
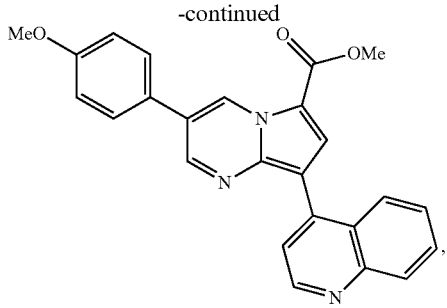
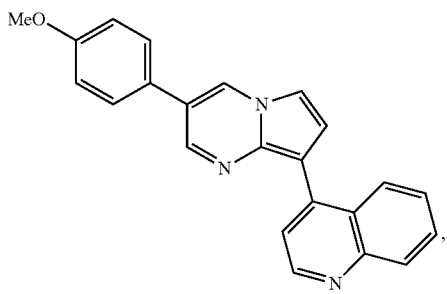
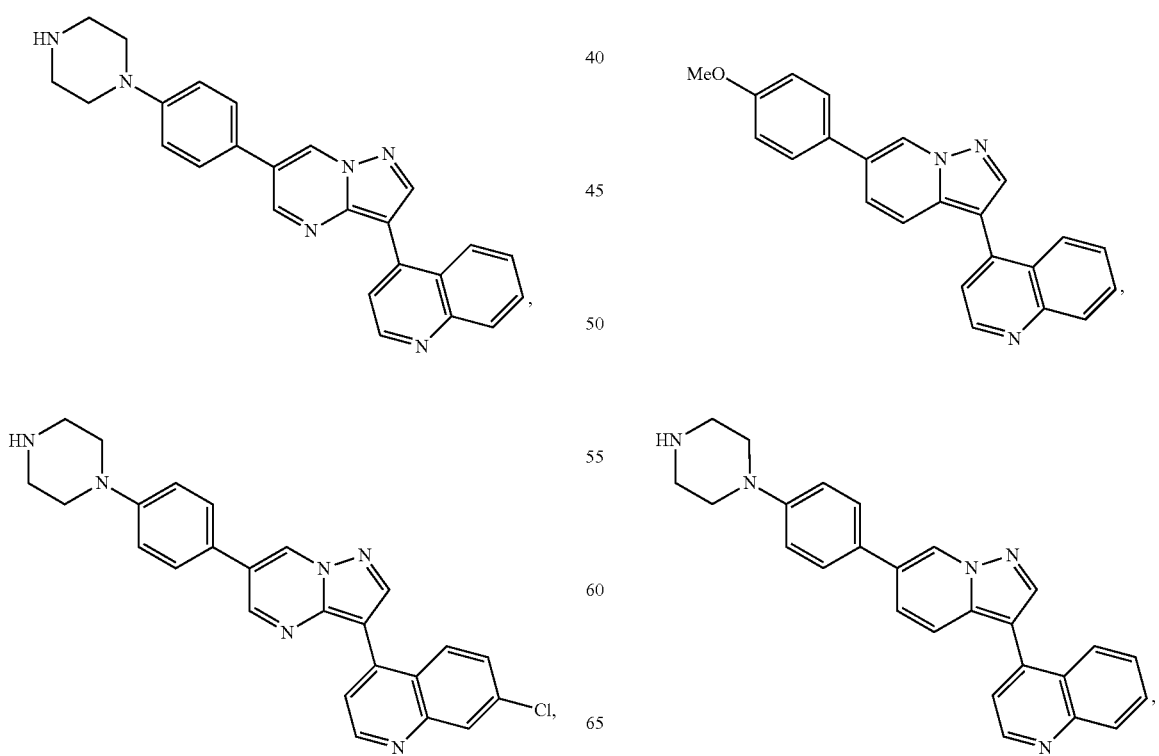

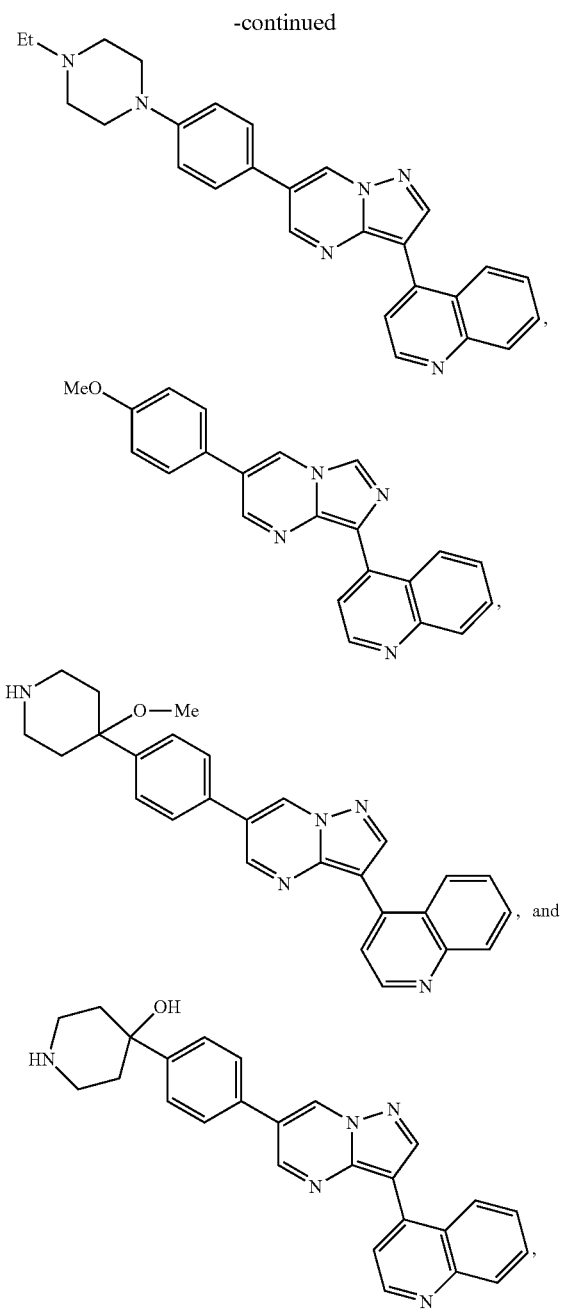

and salts (including pharmaceutically acceptable salts) of the foregoing.

In one aspect, the invention provides a pharmaceutical composition comprising a compound as disclosed herein and a pharmaceutically acceptable excipient or solvent. In certain embodiments, a pharmaceutical composition may comprise a prodrug of a compound as disclosed herein.

In another aspect, the invention provides a method of inhibiting BMP-induced phosphorylation of SMAD1/5/8, comprising contacting a cell with a compound as disclosed herein. In certain embodiments, the method treats or prevents a disease or condition in a subject that would benefit by inhibition of Bone Morphogenetic Protein (BMP) signaling. In certain embodiments, the disease or condition is selected from pulmonary hypertension, hereditary hemorrhagic telangectasia syndrome, cardiac valvular malformations, cardiac structural malformations, fibrodysplasia ossificans progressiva, juvenile familial polyposis syndrome, parathyroid disease, cancer (e.g., breast carcinoma, prostate carcinoma, renal cell carcinoma, bone metastasis, lung metastasis, osteosarcoma, and multiple myeloma), anemia, vascular calcification, atherosclerosis, valve calcification, renal osteodystrophy, inflammatory disorders (e.g., ankylosing spondylitis), infections with viruses, bacteria, fungi, tuberculosis, and parasites.

In another aspect, the invention provides a method of inducing expansion or differentiation of a cell, comprising contacting the cell with a compound as disclosed herein. In certain embodiments, the cell is selected from an embryonic stem cell and an adult stem cell. In certain embodiments, the cell is in vitro.

In certain embodiments, a method of the invention may comprise contacting a cell with a prodrug of a compound as disclosed herein.

DETAILED DESCRIPTION OF THE INVENTION

Figure 1:
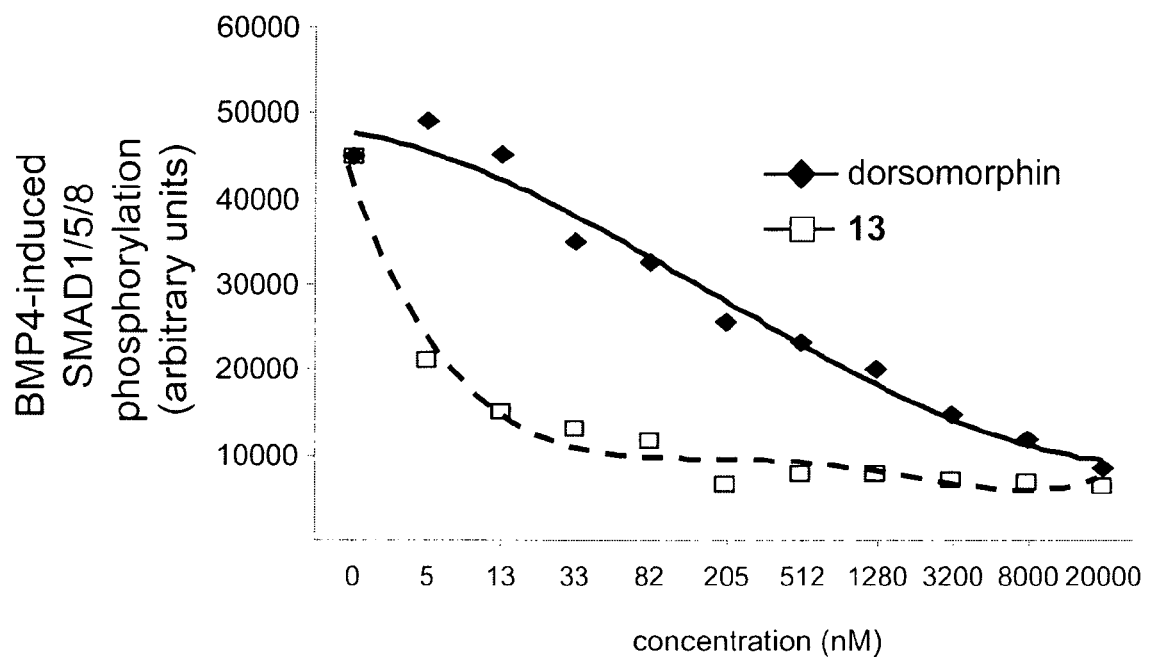
FIG. 1 shows a plot of BMP4-induced SMAD1/5/8 phosphorylation measured by cellular ELISA comparing the effect of dorsomorphin and compound 13.

The invention provides for compounds that inhibit the BMP signaling pathway, as well as methods to treat or prevent a disease or condition in a subject that would benefit by inhibition of BMP signaling.

I. Compounds

Compounds of the invention include compounds of Formula I and Formula II as disclosed above. Such compounds are suitable for the compositions and methods disclosed herein. In other embodiments, the following compounds and their salts (including pharmaceutically acceptable salts) are compounds of the invention and are suitable for the compositions and methods disclosed herein:

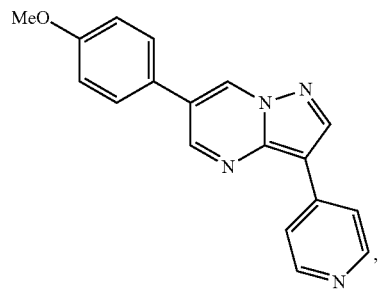

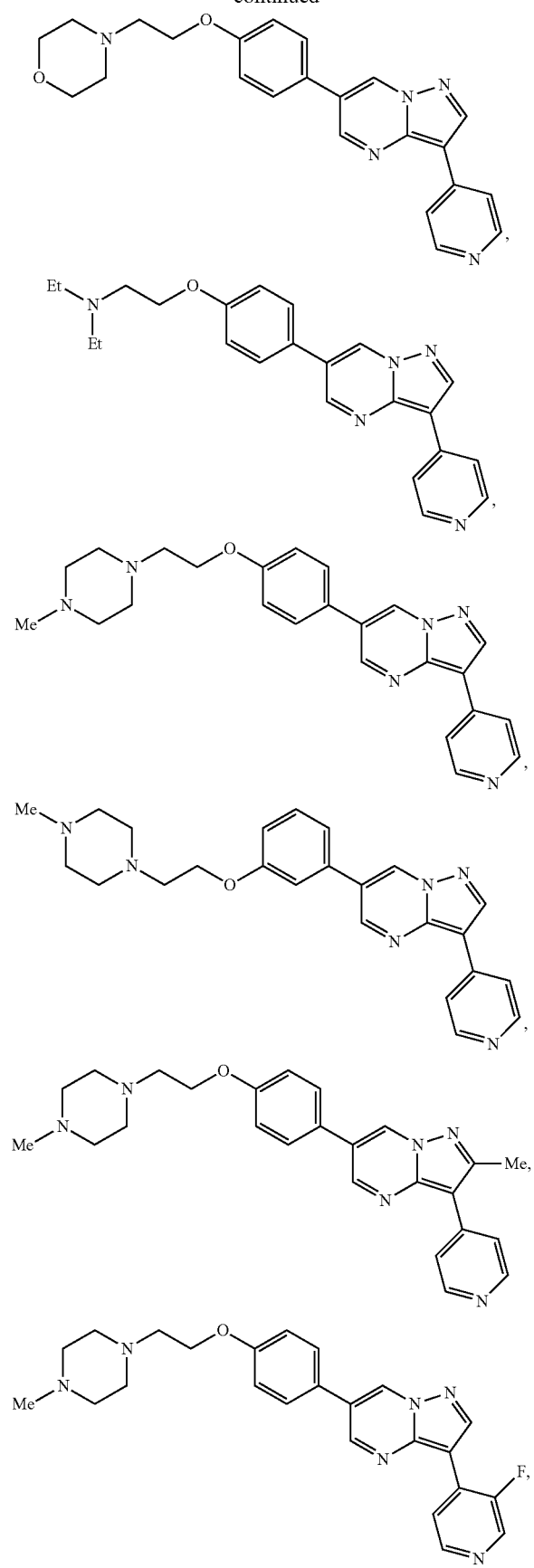

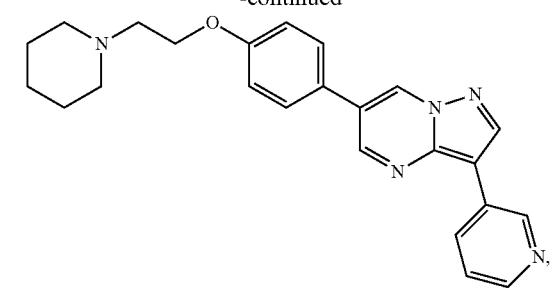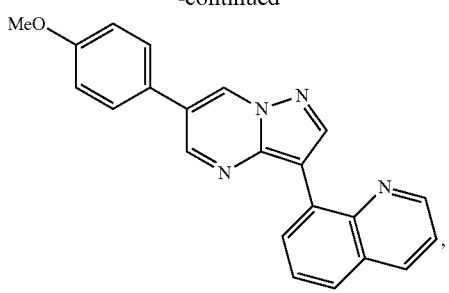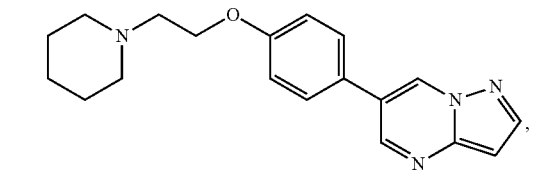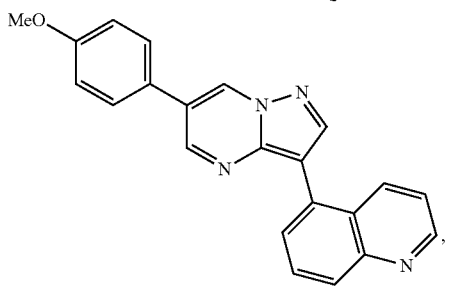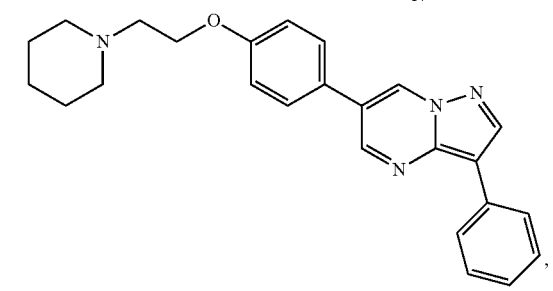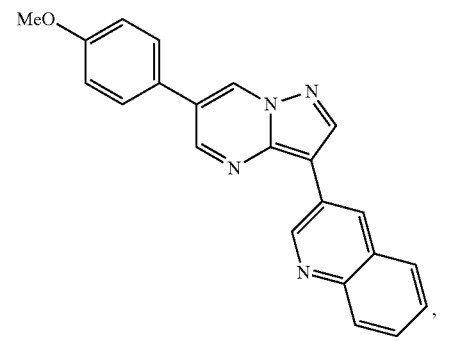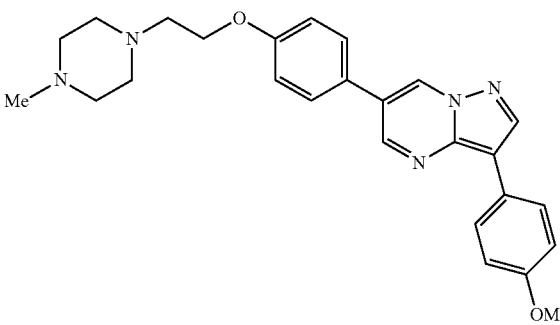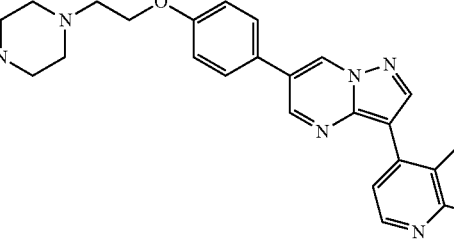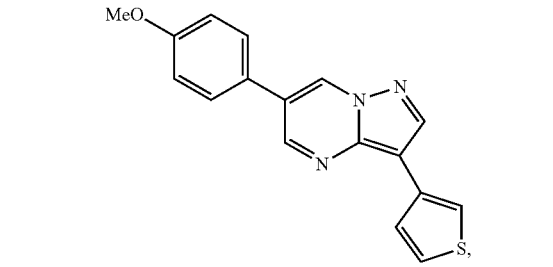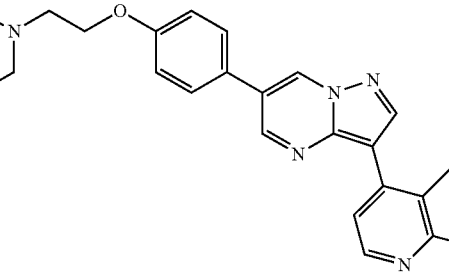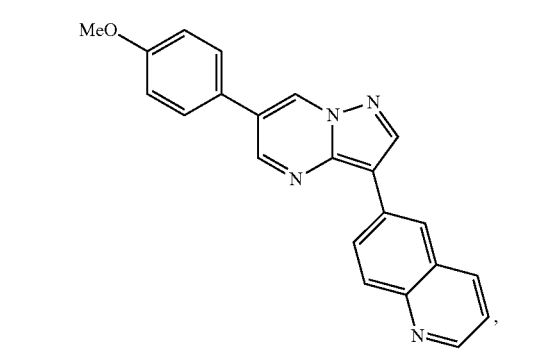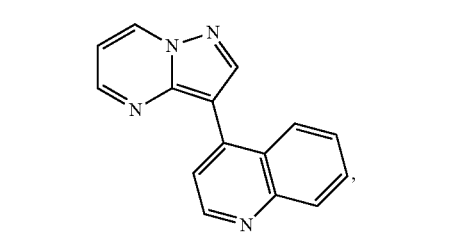

25
-continued
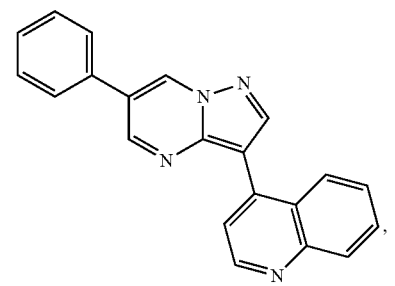
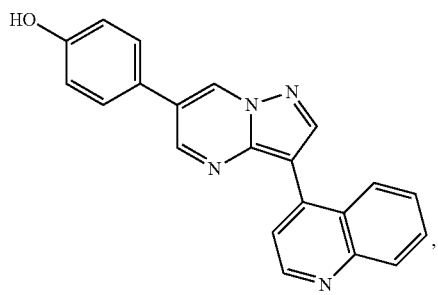
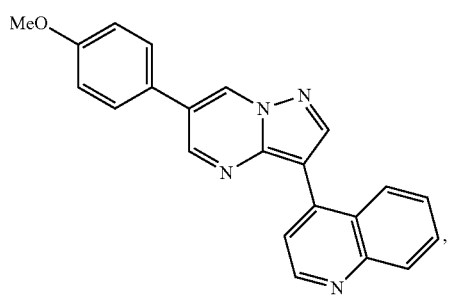
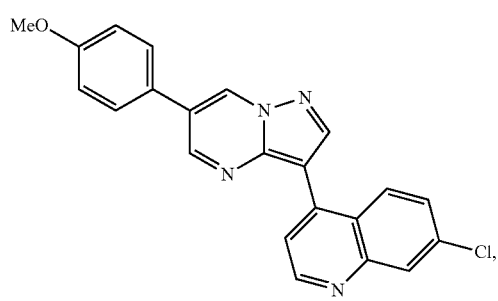
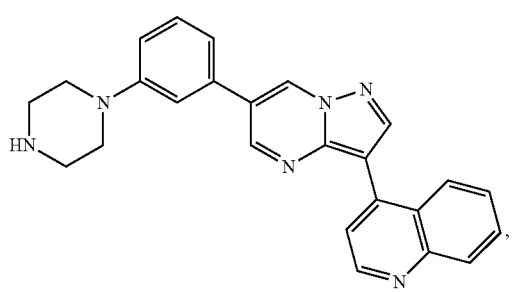
26
-continued
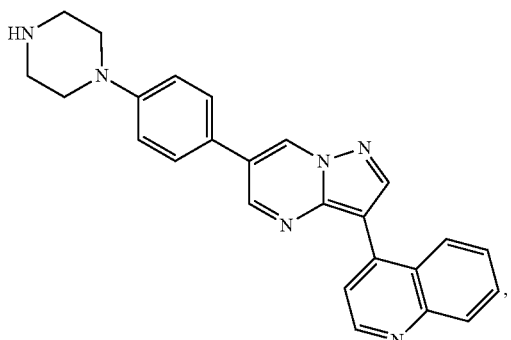
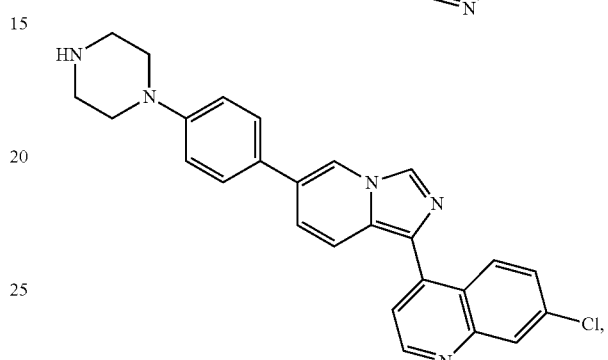
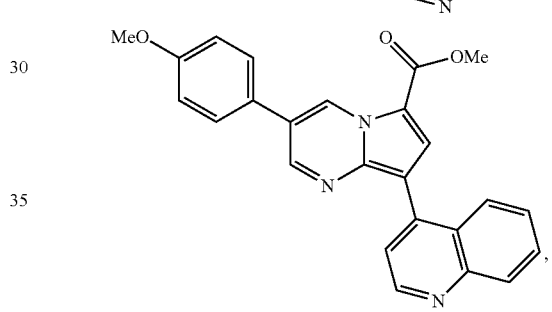
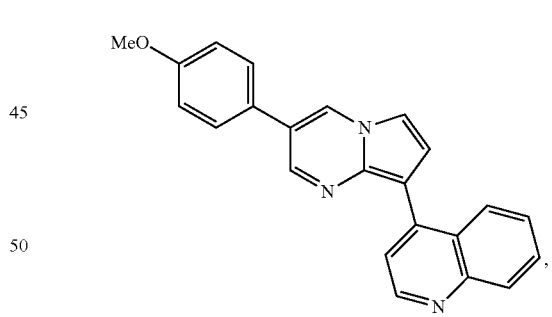
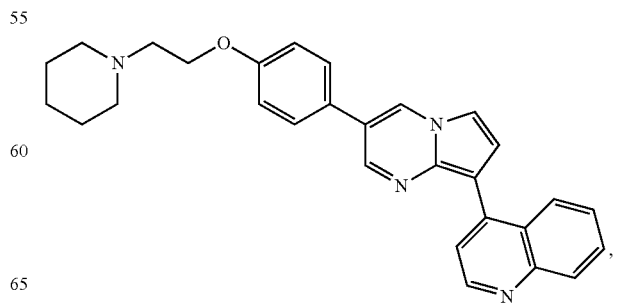

-continued

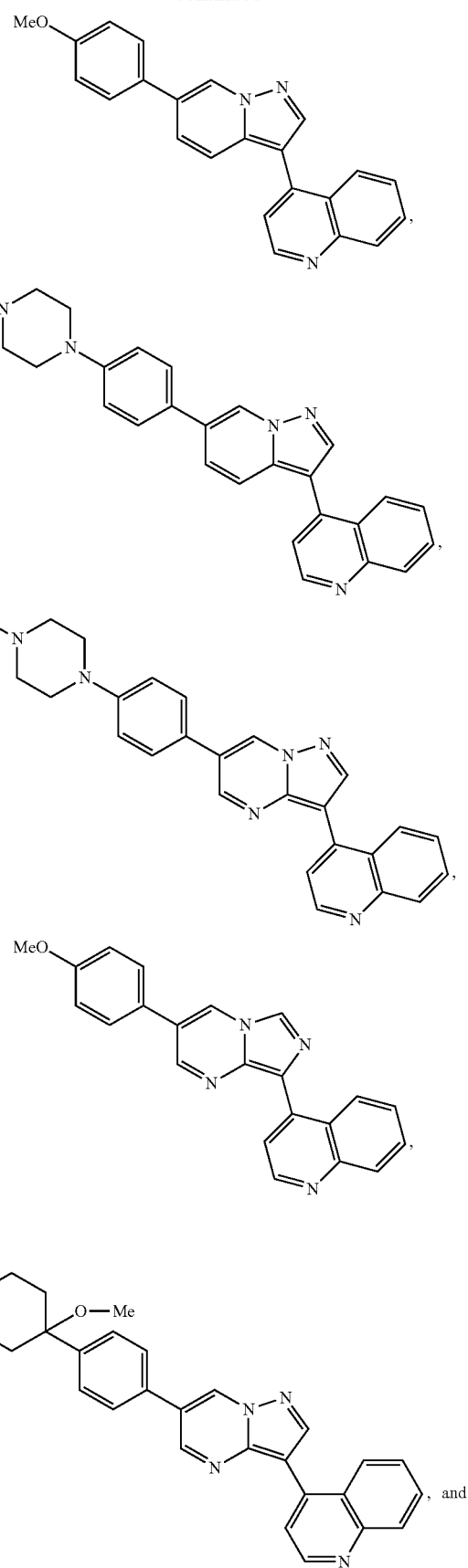

II. Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—, preferably alkylC(O)NH—.

The term "acyloxy" is art-recognized and refers to a group represented by the general formula hydrocarbylC(O)O—, preferably alkylC(O)O—.

The term "aliphatic", as used herein, includes straight, chained, branched or cyclic hydrocarbons which are completely saturated or contain one or more units of unsaturation. Aliphatic groups may be substituted or unsubstituted.

The term "alkoxy" refers to an oxygen having an alkyl group attached thereto. Representative alkoxy groups include methoxy, ethoxy, propoxy, tert-butoxy and the like.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated. In preferred embodiments, a straight chain or branched chain alkenyl has 1-12 carbons in its backbone, preferably 1-8 carbons in its backbone, and more preferably 1-6 carbons in its backbone. Exemplary alkenyl groups include allyl, propenyl, butenyl, 2-methyl-2-butenyl, and the like.

The term "alkyl" refers to the radical of saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g. methyl, ethyl, n-propyl, i-propyl, n-butyl and n-pentyl.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone.

Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS-.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated. In preferred embodiments, an alkynyl has 1-12 carbons in its backbone, preferably 1-8 carbons in its backbone, and more preferably 1-6 carbons in its backbone. Exemplary alkynyl groups include propynyl, butynyl, 3-methylpent-1-ynyl, and the like.

The term "amide", as used herein, refers to a group

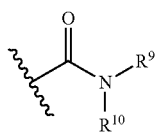

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

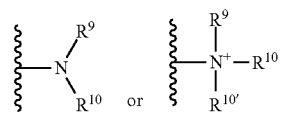

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with one or more aryl groups.

The term "aryl", as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, and the like.

The term "carbamate" is art-recognized and refers to a group

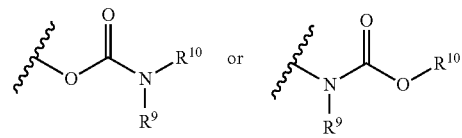

wherein $R^9$ and $R^{10}$ independently represent hydrogen or a hydrocarbyl group, such as an alkyl group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —$OCO_2$—$R^9$, wherein $R^9$ represents a hydrocarbyl group, such as an alkyl group.

The term "carboxy", as used herein, refers to a group represented by the formula —$CO_2H$.

The term "cycloalkyl", as used herein, refers to the radical of a saturated aliphatic ring. In preferred embodiments, cycloalkyls have from 3-10 carbon atoms in their ring structure, and more preferably from 5-7 carbon atoms in the ring structure. Suitable cycloalkyls include cycloheptyl, cyclohexyl, cyclopentyl, cyclobutyl and cyclopropyl.

The term "ester", as used herein, refers to a group —C(O)$OR^9$ wherein $R^9$ represents a hydrocarbyl group, such as an alkyl group or an aralkyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen", as used herein, means halogen and includes chloro, fluoro, bromo, and iodo.

The term "heteroalkyl", as used herein, refers to a saturated or unsaturated chain of carbon atoms including at least one heteroatom (e.g., O, S, or NR$^{50}$, such as where R$^{50}$ is H or lower alkyl), wherein no two heteroatoms are adjacent.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom (e.g., O, N, or S), preferably one to four or one to 3 heteroatoms, more preferably one or two heteroatoms. When two or more heteroatoms are present in a heteroaryl ring, they may be the same or different. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Preferred polycyclic ring systems have two cyclic rings in which both of the rings are aromatic. Heteroaryl groups include, for example, pyrrole, furan, thiophene, imidazole, oxazole, thiazole, pyrazole, pyridine, pyrazine, pyridazine, quinoline, and pyrimidine, and the like.

The term "heteroatom", as used herein, means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. Examples of straight chain or branched chain lower alkyl include methyl, ethyl, isopropyl, propyl, butyl, tertiary-butyl, and the like. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitation aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Preferred polycycles have 2-3 rings. Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulthydryl, an alkylthio, a sulfate, a sulfonate, a sulfamoyl, a sulfonamido, a sulfonyl, a heterocyclyl, an aralkyl, or an aromatic or heteroaromatic moiety.

Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt or ester thereof.

The term "sulfonamide" is art-recognized and refers to the group represented by the general formulae

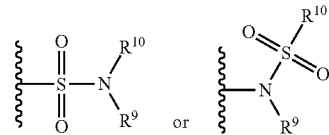

wherein R$^9$ and R$^{10}$ independently represents hydrogen or hydrocarbyl, such as alkyl.

The term "sulfoxide" is art-recognized and refers to the group —S(O)—R$^9$, wherein R$^9$ represents a hydrocarbyl, such as alkyl, aryl, or heteroaryl.

The term "sulfonate" is art-recognized and refers to the group —SO$_3$H, or a pharmaceutically acceptable salt or ester thereof.

The term "sulfone" is art-recognized and refers to the group —S(O)$_2$—R$^9$, wherein R$^9$ represents a hydrocarbyl, such as alkyl, aryl, or heteroaryl.

The term "thioester", as used herein, refers to a group —C(O)SR$^9$ or —SC(O)R$^9$ wherein R$^9$ represents a hydrocarbyl, such as alkyl.

The term "thioether", as used herein, is equivalent to an ether, wherein the oxygen is replaced with a sulfur.

The term "urea" is art-recognized and may be represented by the general formula

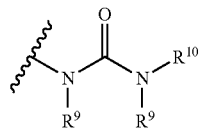

wherein $R^9$ and $R^{10}$ independently represent hydrogen or a hydrocarbyl, such as alkyl.

At various places in the present specification substituents of compounds of the invention are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, propyl, isopropyl, n-butyl, sec-butyl, isobutyl, etc.

For a number qualified by the term "about", a variance of 2%, 5%, 10% or even 20% is within the ambit of the qualified number As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "prodrug" is intended to encompass compounds which, under physiologic conditions, are converted into the therapeutically active agents of the present invention (e.g., a compound of Formula I or Formula II). A common method for making a prodrug is to include one or more selected moieties which are hydrolyzed under physiologic conditions to reveal the desired molecule. In other embodiments, the prodrug is converted by an enzymatic activity of the host animal. For example, esters (e.g., esters of alcohols or carboxylic acids) are preferred prodrugs of the present invention. In various embodiments disclosed herein (e.g., the various compounds, compositions, and methods), some or all of the compounds of formula A, compounds of any one of Formula I or Formula II, all or a portion of a compound of Formula I or Formula II in a formulation represented above can be replaced with a suitable prodrug, e.g., wherein a hydroxyl or carboxylic acid present in the parent compound is presented as an ester.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

III. Pharmaceutical Compositions

Compounds of the present invention may be used in a pharmaceutical composition, e.g., combined with a pharmaceutically acceptable carrier, for administration to a patient. Such a composition may also contain diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. Such additional factors and/or agents may be included in the pharmaceutical composition to produce a synergistic effect with compounds of the invention, or to minimize side effects caused by the compound of the invention.

The pharmaceutical compositions of the invention may be in the form of a liposome or micelles in which compounds of the present invention are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The terms "pharmaceutically effective amount" or "therapeutically effective amount", as used herein, means the total amount of each active component of the pharmaceutical composition or method that is sufficient to show a meaningful patient benefit, e.g., treatment, healing, prevention, inhibition or amelioration of a physiological response or condition, such as an inflammatory condition or pain, or an increase in rate of treatment, healing, prevention, inhibition or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

Each of the methods of treatment or use of the present invention, as described herein, comprises administering to a mammal in need of such treatment or use a pharmaceutically or therapeutically effective amount of a compound of the present invention, or a pharmaceutically acceptable salt or ester form thereof. Compounds of the present invention may be administered in accordance with the method of the invention either alone or in combination with other therapies.

Administration of compounds of the present invention used in the pharmaceutical composition or to practice the method of the present invention can be carried out in a variety of conventional ways, such as oral ingestion, inhalation, or cutaneous, subcutaneous, or intravenous, intramuscular, and intraperitoneal injection.

When a therapeutically effective amount of a compound(s) of the present invention is administered orally, compounds of the present invention may be in the form of a tablet, capsule, powder, solution or elixir. When administered in tablet form, the pharmaceutical composition of the invention may additionally contain a solid carrier such as a gelatin or an adjuvant. The tablet, capsule, and powder may contain from about 5 to 95% compound of the present invention, and preferably from about 10% to 90% compound of the present invention. When administered in liquid form, a liquid carrier such as water, petroleum, oils of animal or plant origin such as peanut oil, mineral oils, phospholipids, tweens, triglycerides, including medium chain triglycerides, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition typically contains from about 0.5 to 90% by weight of compound of the present invention, and preferably from about 1 to 50% compound of the present invention.

When a therapeutically effective amount of a compound(s) of the present invention is administered by intravenous, cutaneous or subcutaneous injection, compounds of the present invention may be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to compounds of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of compound(s) of the present invention in the pharmaceutical composition of the present invention will depend upon the nature and severity of the condition being treated, and on the nature of prior treatments the patient has undergone. Ultimately, the practitioner will decide the amount of compound of the present invention with which to treat each individual patient. Initially, the practitioner may administer low doses of compound of the present invention and observe the patient's response. Larger doses of compounds of the present invention may be administered until the optimal therapeutic effect is obtained for the patient, and at that point the dosage is not increased further. It is contemplated that the various pharmaceutical compositions used to practice the method of the present invention should contain about 0.1 µg to about 100 mg (preferably about 0.1 mg to about 50 mg, more preferably about 1 mg to about 2 mg) of compound of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the compounds of the present invention will be in the range of 12 to 24 hours of continuous intravenous administration. Ultimately the practitioner will decide on the appropriate duration of intravenous therapy using the pharmaceutical composition of the present invention.

IV. Use With Polymers

The compounds as disclosed herein may be conjugated to a polymer matrix, e.g., for controlled delivery of the compound. The compound may be conjugated via a covalent bond or non-covalent association. In certain embodiments wherein the compound is covalently linked to the polymer matrix, the linkage may comprise a moiety that is cleavable under biological conditions (e.g., ester, amide, carbonate, carbamate, imide, etc.). In certain embodiments, the conjugated compound may be a pharmaceutically acceptable salt, ester, or prodrug of a compound disclosed herein. A compound as disclosed herein may be associated with any type of polymer matrix known in the art for the delivery of therapeutic agents.

V. Synthetic Preparation

The compounds disclosed herein can be prepared in a variety of ways known to one skilled in the art of organic synthesis, and in analogy with the exemplary compounds whose synthesis is described herein. The starting materials used in preparing these compounds may be commercially available or prepared by known methods. Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis,* 44th. Ed., Wiley & Sons, 2006, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

VI. Uses

BMPs and TGF-beta signaling pathways are essential to normal organogenesis and pattern formation, as well as the normal and pathological remodeling of mature tissues. Defects in the BMP signaling pathway are implicated in a number of congenital and acquired disease processes, including Hereditary Hemorrhagic Telangectasia syndrome, Primary Pulmonary Hypertension, Juvenile Familial Polyposis, as well as sporadic renal cell and prostate carcinomas. It has been suggested that in certain disease states associated with defective signaling components, attenuated BMP signaling might be a cause, while our findings have suggested that in some contexts excess BMP signaling might be pathogenic (Waite et al. *Nat. Rev. Genet.* 4:763-773, 2005; Yu et. *J. Biol. Chem.* 280:24443-24450, 2003). The ability to modulate BMP signaling experimentally would provide a means for investigating therapy, and for determining the root causes of these conditions.

A. Treatment of Anemia, Including Iron Deficiency and Anemia of Chronic Disease

For a review, see Weiss et al. *N. Engl. J. Med.* 352:1011-1023, 2005. Anemia of inflammation (also called anemia of chronic disease) can be seen in patients with chronic infections, autoimmune diseases (such as systemic lupus erythematosis and rheumatoid arthritis, and Castleman's disease), inflammatory bowel disease, cancers (including multiple myeloma), and renal failure. Anemia of inflammation is often caused by maladaptive expression of the peptide hormone hepcidin. Hepcidin causes degradation of ferroportin, a critical protein that enables transport of iron from intracellular stores in macrophages and from intestinal epithelial cells. Many patients with renal failure have a combination of erythropoietin deficiency and excess hepcidin expression. BMP signaling induces expression of hepcidin and inhibiting hepcidin expression with BMP antagonists increases iron levels. Compounds as described herein can be used to treat anemia due to chronic disease or inflammation and associated hyperhepcidinemic states.

The inflammatory cytokine IL-6 is thought to be the principal cause of elevated hepcidin expression in inflammatory states, based upon the elevation of IL-6 in anemia of inflammation of diverse etiologies, the effects of chronic IL-6 administration in vivo, and the protection against anemia in rodents deficient in IL-6 (Weiss et al. *N. Engl. J. Med.* 352: 1011-1023, 2005). It has been shown that stimulating hepatoma cell lines with IL-6 induces hepcidin expression, while treatment with a BMP antagonist abrogates IL-6-induced hepcidin expression (Yu et al. *Nat. Chem. Biol.* 4:33-41, 2008). Moreover, we have found that BMP antagonists can inhibit hepcidin expression induced by injection of pathogenic bacteria in vivo (see Example 8). It has also been shown that systemic iron administration in mice and zebrafish rapidly activates BMP-responsive-SMADs and hepcidin expression in the liver, and that BMP antagonism effectively blocks these responses (Yu et al. *Nat. Chem. Biol.* 4:33-41, 2008). The functional importance of BMP signaling in iron regulation is supported by our finding that BMP antagonists can inhibit hepcidin expression and raise serum iron levels in vivo (see Example 7). Taken together these data suggest that iron- and inflammation-mediated regulation of hepcidin and circulating iron levels require BMP signaling. Compounds as described herein may be used to alter iron availability in diverse circumstances for therapeutic benefit.

Compounds as described herein may be used in anemic states to (i) augment the efficacy of dietary iron or oral iron supplementation (which is safer than intravenous administration of iron) to increase serum iron concentrations; (ii) augment build up of hemoglobin in the blood in anticipation of surgery or to enable blood donation for self in anticipation of surgery; and (iii) enhance the efficacy of erythropoietin and its relatives, thereby enabling lower doses of erythropoietin to be administered for anemia while minimizing known toxicities and side effects of erythropoietin (i.e., hypertension, cardiovascular events, and tumor growth).

B. Treatment of Fibrodysplasia Ossificans Progressiva (FOP)

FOP is caused by the presence of a constitutively-active mutant form of ALK2 in affected individuals (Shore et al. *Nat. Genet.* 38:525-527, 2006). A specific inhibitor of BMP signaling such as a compound as described herein can be used to prevent excessive bone formation in response to trauma, musculoskeletal stress or inflammation. Such a compound could also be used to aid in regression of pathologic bone. The BMP inhibitor could be administered systemically or locally to concentrate or limit effects to areas of trauma or inflammation.

A BMP inhibitor as described herein may be used as chronic therapy to suppress spontaneous bone formation in individuals who are highly susceptible. Transient therapy may be used to prevent abnormal bone formation in FOP individuals who develop osteomas or pathologic bone most frequently in association with trauma by administration before, during, or even after the traumatic incident. Transient therapy with BMP inhibitors as described herein could be used before, during or immediately after necessary or emergent medical or surgical procedures (and even important immunizations and tooth extractions) in individuals with FOP, to prevent pathologic calcification. Combination therapy with other bone inhibiting agents, immune modulatory or anti-inflammatory drugs (such as NSA/Ds, steroids, cyclosporine, cyclophosphamide, azathioprine, methotrexate, rituximab, etanercept, or similar drugs) may increase the effectiveness of BMP antagonists in inhibiting heterotopic bone formation in this disorder.

A mouse model of FOP has been developed in which expression of a constitutively-active mutant form of ALK2 is induced by injecting the popliteal fossa of a genetically-modified mouse with an adenovirus directing expression of Cre recombinase. This model reproduces the ectopic calcification and disability seen in FOP patients. Twice daily administration of compound 13 (3 mg/kg ip) prevented the ectopic calcification and disability (see Example 10).

C. Treatment of Cancers

Excessive BMP signaling, which could arise due to over-expression of BMPs, or, paradoxically, as a result of loss of BMP type II receptor expression, may contribute to the oncogenesis, growth or metastasis of certain solid tumors, including breast, prostate carcinomas, bone, lung, and renal cell carcinomas (Yu et al. *J. Biol. Chem.* 280:24443-24450, 2008; Waite et al. *Nat. Rev. Genet.* 4:763-773, 2003; Alarmo et al. *Genes, Chromosomes Cancer* 45:411-419, 2006; Kim et al. *Cancer Res.* 60:2840-2844, 2000; Kim et al. *Clin. Cancer Res.* 9:6046-6051, 2003; Kim et al. *Oncogene* 23:7651-7659, 2004). If increased BMP activity associated with BMP overexpression or BMP type II receptor deficiency contributes to the pathogenesis of disease, then inhibiting BMP signaling activity using compounds as described herein at the level of BMP type I receptors (downstream of both ligands and type II receptor) could be an effective means of normalizing BMP signaling activity and potentially inhibiting tumor growth or metastasis.

Compounds as described herein can be used to slow or arrest the growth or metastasis of such tumor cells (as well as other tumor constituent cell types) for clinical benefit, either as adjunctive or primary chemotherapy. Also, BMP inhibitors as described herein may be used to interfere with the bone metastatic properties of certain types of cancers (e.g., adenocarcinoma, such as prostate and breast carcinomas). In addition, compounds as described herein can be used to inhibit osteoblastic activity in tumors that either form bone or are bone-derived, such as osteosarcomas (as adjunctive or primary chemotherapy). Further, compounds as described herein can be used to inhibit osteoclastic activity (also regulated by BMPs through the action of its target gene RANKL), which is pathologically increased in conditions such as multiple myeloma and other bone-targeted tumors. Application of BMP inhibitors in these conditions may reduce the presence of osteolytic lesions and bone fractures due to tumor involvement.

D. Immune Modulation Via BMP Antagonists

BMPs have been reported to attenuate the inflammatory or immune response (Choi et al. *Nat. Immunol.* 7:1057-1065, 2006; Kersten et al. *BMC Immunol.* 6:9, 2005), which can impair an individual's ability to fight infections (i.e., viral, bacterial, fungal, parasitic, or tuberculosis). Inhibitors of BMP signaling as described herein may thus augment the inflammatory or immune response enabling individuals to clear infections more rapidly.

Lymphocytes and other immune cells express BMP receptors on their cell surfaces, and there is growing evidence that BMPs regulate the development and maturation of various humoral and cellular immunologic compartments, and regulate humoral and cellular immune responses in mature organisms. The effects of BMP signals on immune cells are likely to be context-specific, as is commonly known for the effects of numerous cytokines of immunologic importance, and thus whether they augment or diminish the development or function of particular lymphocyte populations must be empirically determined. BMP antagonism using compounds as described herein may be an effective strategy for intentionally biasing the development of cellular, innate, or humoral immune compartments for therapy, or a strategy for the therapeutic deviation of immune responses in mature immune systems. These strategies may target inborn disorders of cellular, innate, or humoral immunity, or target disorders in which immune responses are inappropriately weak (e.g., as an adjuvant to promote successful antigen sensitization when immunization is difficult or ineffective by other means), or target disorders in which immune responses are excessive or inappropriate (e.g., autoimmunity and autosensitization). BMP antagonists as described herein may also be effective in some contexts for the intentional induction of immune tolerance (i.e., in allotransplantation or autoimmunity).

E. Treatment of Pathologic Bone Formation

Compounds as described herein can be used to ameliorate pathologic bone formation/bone fusion in inflammatory disorders, such as ankylosing spondylitis or other "seronegative" spondyloarthropathies, in which autoimmunity and inflammation in such disorders appear to stimulate bone formation. One application of the compounds would be to prevent excess bone formation after joint surgery, particularly in patients with ankylosing spondylitis or rheumatoid arthritis. Compounds as described herein can also be used to prevent calcinosis (dystrophic soft-tissue calcification) in diseases such as systemic lupus erythematosus, scleroderma, or dermatomyositis.

Blunt traumatic injury to muscles can cause abnormal bone formation within muscle in certain individuals, resulting in a disorder called myositis ossificans traumatica (Cushner et al. *Orthop. Rev.* 21:1319-1326, 1992.). Head trauma and burn injury can also induce heterotopic bone formation markedly impairing patient rehabilitation and recovery. Treatment with a BMP inhibitor as described herein, optionally in addition to anti-inflammatory medications usually prescribed for such a condition (eg. non-steroidal anti-inflammatory drugs such as indomethacin or ibuprofen) may help to prevent the formation of pathologic bone in predisposed individuals, or to help lessen or regress lesions in individuals recently or remotely affected. Very rarely other muscles have been described to develop ossification in the presence of injury or trauma, including heart muscle, and similar treatment with a BMP inhibitor as described herein could be helpful in those circumstances.

F. Treatment of Ectopic or Maladaptive Bone Formation

BMP signals and their transcriptional targets are implicated in intimal and medial vascular remodeling and calcification in Monckeberg's vascular calcification disease and in atheromatous vascular disease (Bostrom et al. *J. Clin. Invest.* 91:1800-1809, 1993; Tyson et al. *Arterioscler. Thromb. Vasc. Biol.* 23:489-494, 2003). BMPs and BMP-induced osteodifferentation are also implicated in cardiac valvular calcification. Native cardiac valves can calcify particularly when they are already abnormal. A classic example is bicuspid aortic valve—these valves typically become calcified leading to stenosis. Patients with calcific aortic valve stenosis often require cardiac surgery for valve replacement. Abnormal calcification can adversely affect the function of prosthetic vascular grafts or cardiac valves. For example, prosthetic heart valves become calcified leading to narrowing and often leakage.

Compounds as described herein can be used to inhibit vascular or valvular calcific disease alone or in combination with atheromatous disease, renal disease, renal osteodystrophy or parathyroid disease.

Compounds as described herein can be used to inhibit calcification of prosthetic vascular or valvular materials by systemic or local administration or direct incorporation into prosthesis materials or other implants (e.g., in admixture with a polymer that coats or constitutes all or part of the implant or prosthesis).

In some instances, it is desired to delay fracture healing following a bone fracture, or to purposely inhibit fracture healing in certain locations to prevent impairment of function by maladaptive bone formation. For example, if a fracture occurs and for medical or practical reasons surgery cannot be performed immediately, fracture healing may be temporarily "suspended" by use of a BMP inhibitor as described herein, until definitive surgery or manipulation can be performed. This could prevent the need for subsequent intentional re-fracture in order to ensure correct apposition of bone fragments, for example. It is expected that upon stopping a BMP inhibitor normal fracture healing processes would ensue if the period of treatment is relatively short. In other cases, any amount of novel bone growth might impair function, such as when fracture affects a joint directly. In these cases, global or local inhibition of BMP activity (by systemic or local delivery of a BMP antagonist as described herein via diffusion from a local implant or matrix) may be used to inhibit fracture healing or prevent fracture calluses at the critical areas.

G. Treatment of Skin Diseases

Expansion of cultured keratinocytes—In vitro, BMPs inhibit keratinocyte proliferation and promote differentiation (reviewed in Botchkarev et al. *Differentiation* 72:512-526, 2004). In patients in need of skin grafting (eg. after burns), skin grafts are made from cultured keratinocytes. The keratinocytes may be derived from other animals (xenografts), but these are only temporary as they will be rejected by the immune system. Keratinocytes can be derived from the patient themselves and can be grown into sheets of cells in the laboratory (cultured epithelial autografts). The patient will not reject keratinocytes derived from his/her own body. Addition of BMP antagonists as described herein to keratinocyte cultures can be used to facilitate keratinocyte proliferation enabling patients to receive grafts sooner.

Improved epithelialization—BMP6 is highly expressed in skin injury, and high levels of BMP6 are detected in chronic human wounds of different etiologies (Kaiser et al. *J. Invest. Dermatol.* 111:1145-1152, 1998). In mice overexpressing BMP6 in their skin, reepithelialization and healing skin wounds were significantly delayed (Kaiser et al. *J. Invest. Dermatol.* 111:1145-1152, 1998). Improved epithelialization can reduce scar formation. Topical or systemic administration of BMP antagonists as described herein can be used to augment epithelialization of skin wounds, for example, in the treatment of pressure ulcers (bed sores) or non-healing or poorly-healing skin ulcers (e.g., in patients with peripheral vascular disease, diabetes mellitus, venous incompetence). Compounds would also be expected to decrease scar formation.

Promotion of hair growth—Growth of hair follicles on the scalp is cyclic with three phases: anagen (the growth phase), catagen (the involutional phase), and telogen (resting phase). Recent evidence suggests that BMP signals delay the transition from telogen to anagen (Plikus et al. *Nature* 451:340-344, 2008). Inhibition of BMP signaling using compounds as described herein can shorten the telogen phase and increase the number of follicles in the anagen phase. Compounds as described herein can be used to treat circumstances wherein hair follicles are insufficient or when hairs are being lost more frequently than they are grown. These circumstances include androgenetic alopecia (male pattern balding), alopecia greata, and telogen effluvium.

Treatment of psoriasis—Psoriasis is an inflammatory skin disorder which sometimes occurs following skin trauma and the ensuing repair and inflammation (Koebner phenomenon). BMPs may participate in repair and inflammatory mechanisms that cause psoriasis, since over-expression of BMP6 in the skin of mice leads to skin lesions similar to those seen in patients with psoriasis (Blessing et al. *J. Cell. Biol.* 135:227-239, 1996). Compounds as described herein may be administered topically or systemically to treat established psoriasis or prevent its development after skin injury.

Treatment of corneal scarring—BMP6 expression is associated with conjunctival scarring (Andreev et al. *Exp. Eye Res.* 83:1162-1170, 2006). Compounds as described herein can be used to prevent or treat corneal scarring and the resulting blindness.

H. Treatment of Systemic Hypertension

Infusion of BMP4 induces systemic hypertension in mice (Miriyala et al. *Circulation* 113:2818-2825, 2006). Vascular smooth muscle cells express a variety of BMP ligands. BMPs increase the expression of voltage gated potassium channels and thereby increase constriction of vascular smooth muscle (Fantozzi et al. *Am. J. Physiol. Lung Cell. Mol. Physiol.* 291:L993-1004, 2006). Compounds as described herein that inhibit BMP signaling can be used to reduce blood pressure. Sustained reduction of blood pressure in patients with hypertension would be expected to prevent myocardial infarction, congestive heart failure, cerebrovascular accidents, and renal failure. BMP inhibitors as described herein can be used to target the hypertension in specific vascular beds, such as in pulmonary hypertension via local delivery (e.g., via aerosol).

I. Treatment of Pulmonary Hypertension

BMP signaling contributes to the pathogenesis of pulmonary hypertension. For example, mice with decreased BMP4 levels are protected from the pulmonary hypertension and pulmonary vascular remodeling induced by breathing low oxygen concentrations for prolonged periods (Frank et al. *Circ. Res.* 97:496-504, 2005). Moreover, mutations in the gene encoding the type II BMP receptor (BMPRII) are frequently found in patients with sporadic and familial pulmonary arterial hypertension. It might be anticipated that decreased BMP signaling might cause pulmonary hypertension. However, Yu and colleagues (Yu et al. *J. Biol. Chem.* 280:24443-24450, 2008) reported that BMPRII deficiency paradoxically increases BMP signaling by subsets of BMP ligands, and thus increased BMP signaling using compounds as described herein may actually contribute to the development of pulmonary hypertension.

Compounds as described herein can used to prevent the development of pulmonary arterial hypertension in patients at risk for the disease (e.g., patients with BMPRII mutations) or to treat patients with idiopathic or acquired pulmonary arterial hypertension. Decreased pulmonary hypertension in individuals treated with the compounds described herein would be expected to decrease shortness of breath, right ventricular hypertrophy, and right ventricular failure.

J. Treatment of Ventricular Hypertrophy

BMP-10 levels are increased in the hypertrophied ventricles of rats with hypertension, and this BMP ligand induces hypertrophy in cultured neonatal rat ventricular myocytes (Nakano et al. *Am. J. Physiol. Heart. Circ. Physiol.* 293: H3396-3403, 2007). Inhibition of BMP-10 signaling with compounds as described herein can to prevent/treat ventricular hypertrophy. Ventricular hypertrophy can lead to congestive heart failure due to diastolic dysfunction. Compounds described herein would be expected to prevent/treat congestive heart failure.

K. Treatment of Neurologic Disorders

Treatment of spinal cord injury and neuropathy—BMPs are potent inhibitors of axonal regeneration in the adult spinal cord after spinal cord injury (Matsuura et al. *J. Neurochem.* 2008). Expression of BMPs is reported to be elevated in oligodendrocytes and astrocytes around the injury site following spinal cord contusion. Intrathecal administration of noggin, a BMP inhibitor, led to enhanced locomotor activity and significant regrowth of the corticospinal tract after spinal cord contusion.

RGMa inhibits axonal growth and recovery after spinal cord injury, as well as synapse re-formation, effects which are blocked by an antibody directed against RGMa (Hata et al. *J. Cell. Biol.* 173:47-58, 2006; Kyoto et al. *Brain Res.* 1186:74-86, 2007). RGMa enhances BMP signaling (Babitt et al. *J. Biol. Chem.* 280:29820-29827, 2005) suggesting that BMP signaling may be responsible for preventing axonal growth and recovery.

Based on these considerations, compounds as described herein would be expected to increase axonal growth and recovery after spinal cord injury. Compounds as described herein would be expected to prevent/treat neuropathies associated with a wide spectrum of disorders including diabetes mellitus. Compounds as described herein would be expected to treat both the pain and motor dysfunction associated with neuropathies.

Treatment of neurologic disorders associated with central nervous system inflammation—BMP4 and 5 have been detected in multiple sclerosis and Creutzfeldt-Jakob disease lesions (Deininger et al. *Acta Neuropathol.* 90:76-79, 1995). BMPs have also been detected in mice with experimental autoimmune encephalomyelitis, an animal model of multiple sclerosis (Ara et al. *J. Neurosci. Res.* 86:125-135, 2008). Compounds as described herein may be used to prevent or treat multiple sclerosis as well as other neurologic disorders associated with central nervous system inflammation, or maladaptive injury repair processes mediated by BMP signals.

Treatment of dementias—Inhibitors of BMP signaling can promote neurogenesis in mouse neural precursor cells (Koike et al. *J. Biol. Chem.* 282:15843-15850, 2007). Compounds as described herein can be used to augment neurogenesis in a variety of neurologic disorders associated with accelerated loss of neurons including cerebrovascular accidents and Alzheimer's Disease, as well as other dementias.

Altering memory and learning—BMP signaling has an important role in the development and maintenance of neurons involved in memory and cognitive behavior. For example, mice deficient in the BMP antagonist, chordin, have enhanced spatial learning but less exploratory activity in a novel environment (Sun et al. *J. Neurosci.* 27:7740-7750, 2007). Compounds as described herein can be used to alter or prevent memory or learning, for example, inducing amnesia for anesthesia or in other situations likely to cause distress, or to prevent Post-Traumatic Stress Disorder.

L. Treatment of Atherosclerosis

Abundant evidence suggests that BMP ligands are pro-inflammatory and pro-atherogenic in the blood vessel wall (Chang et al. *Circulation* 116:1258-1266, 2007). Knocking-down expression of BMP4 decreased inflammatory signals, whereas knocking-down BMP antagonists (egfollistatin or noggin) increased inflammatory signals. Compounds as described herein can be used to reduce vascular inflammation associated with atherosclerosis, autoimmune disease, and other vasculitides. By decreasing atherosclerosis, it would be anticipated that compounds as described herein would decrease acute coronary syndromes (angina pectoris and heart attack), transient ischemic attacks, stroke, peripheral vascular disease, and other vascular ischemic events. Moreover, in so far as atherosclerosis contributes to the pathogenesis of aneurysm formation, compounds as described herein can be used to slow the progression of aneurysm formation decreasing the frequency of aneurismal structure and the requirement for vascular surgery.

As BMPs and many of the BMP-induced gene products that affect matrix remodeling are overexpressed in early atherosclerotic lesions, BMP signals may promote plaque formation and progression (Bostrom et al. J Clin Invest. 91:

1800-1809. 1993; Dhore et al. Arterioscler Thromb Vasc Biol. 21: 1998-2003. 2001). BMP signaling activity in the atheromatous plaque may thus represent a form of maladaptive injury-repair, or may contribute to inflammation. Over time, BMP signals may also induce resident or nascent vascular cell populations to differentiate into osteoblast-like cells, leading to intimal and medial calcification of vessels (Hruska et al. Circ Res. 97: 105-112. 2005). Calcific vascular disease, or arteriosclerosis, is associated with decreased vascular distensibility, and increased risk of cardiovascular events and mortality, and is particularly problematic when associated with underlying atherosclerotic disease (Bostrom et al. Crit Rev Eukaryot Gene Expr. 10: 151-158. 2000). Both atherosclerotic and calcific lesions may be amenable to regression, however, if signals which contribute to their progression can be intercepted (Sano et al. Circulation. 103: 2955-2960. 2001). In certain aspects, compound 13 or another inhibitor of BMP type I receptor activity may be used to limit the progression of atheromatous plaques and vascular calcification in vivo.

M. Propagation, Engraftment and Differentiation of Progenitor Cells Including Embryonic and Adult Stem Cells In Vitro and In Vivo BMP signals are crucial for regulating the differentiation and regeneration of precursor and stem cell populations, in some contexts and tissues preventing (while in other contexts directing) differentiation towards a lineage. Compounds as described herein can be used to (i) maintain a pluripotential state in stem cell or multipotent cell populations in vivo or in vitro; (ii) expand stem cell or multipotent cell populations in vivo or in vitro; (iii) direct differentiation of stem cell or multipotent cell populations in vivo or in vitro; (iv) manipulate or direct the differentiation of stem cell or multipotent cell populations in vivo or in vitro, either alone or in combination or in sequence with other treatments; and (v) modulate the de-differentiation of differentiated cell populations into multipotent or progenitor populations.

Numerous stem cell and precursor lineages require BMP signals in order to determine whether they will expand, differentiate towards specific tissue lineages, home in and integrate with particular tissue types, or undergo programmed cell death. Frequently BMP signals interact with signals provided by growth factors (bFGF, PDGF, VEGF, HBEGF, PIGF, and others), Sonic Hedgehog (SHH), notch, and Wnt signaling pathways to effect these changes (Okita et al. *Curr. Stem Cell Res. Ther.* 1:103-111, 2006). Compounds as described herein can be used to direct the differentiation of stem cells (e.g., embryonic stem cells) or tissue progenitor cells towards specific lineages for therapeutic application (Park et al. *Development* 131:2749-2762, 2004; Pashmforoush et al. *Cell* 117:373-386, 2004). Alternatively for certain cell populations, BMP inhibitors as described herein may be effective in preventing differentiation and promoting expansion, in order to produce sufficient numbers of cells to be effective for a clinical application. The exact combination of BMP antagonist and growth factor or signaling molecule may be highly specific to each cell and tissue type.

For example, certain embryonic stem cell lines require co-culture with leukemia inhibitory factor (LIF) to inhibit differentiation and maintain the pluripotency of certain cultured embryonic stem cell lines (Okita et al. *Curr. Stem Cell Res. Ther.* 1:103-111, 2006). Use of a BMP inhibitor as described herein may be used to maintain pluripotency in the absence of LIF. Other ES cell lines require coculture with a specific feeder cell layer in order to maintain pluripotency. Use of a BMP inhibitor as described herein, alone or in combination with other agents, may be effective in maintaining pluripotency when concerns of contamination with a feeder cell layer, or its DNA or protein components would complicate or prevent use of cells for human therapy.

In another example, in some circumstances antagonizing BMP signals with a protein such as noggin shortly before cessation of LIF in culture is able to induce differentiation into a cardiomyocyte lineage (Yuasa et al. *Nat. Biotechnol.* 23:607-611, 2005). Use of a pharmacologic BMP antagonist as described herein may achieve similar if not more potent effects. Such differentiated cells could be introduced into diseased myocardium therapeutically. Alternatively, such treatment may actually be more effective on engrafted precursor cells which have already homed in to diseased myocardium. Systemic therapy with a protein antagonist of BMP such as noggin would be prohibitively expensive and entail complicated dosing. Delivery of a BMP antagonist as described herein, systemically or locally, could bias the differentiation of such precursor cells into functioning cardiomyocytes in situ.

N. Application of Compounds with Varying Degrees of Selectivity: Compounds Which Inhibit BMP Signaling Via Particular BMP Type I Receptors, or Compounds Which also Affect signaling Via TGF-β, Activin, AMP Kinase, or VEGF Receptors ALK-specific antagonists—Dorsomorphin inhibits the activity of the BMP type I receptors, ALK2, ALK3, and ALK6. Dorsomorphin inhibits ALK2 and ALK3 to a greater extent than it does ALK6 (Yu et al. *Nat. Chem. Biol.* 4:33-41, 2008). Several of the compounds described herein will have relative greater selectivity for particular BMP type I receptors. The pathogenesis of certain diseases might be attributed to the dysfunctional signaling of one particular receptor. For example, fibrodysplasia ossificans progressiva is a disease caused by aberrant (constitutively active) ALK2 function (Yu et al. *Nat. Chem. Biol.* 4:33-41, 2008). In such instances, compounds as described herein which specifically antagonize the function a subset of the BMP type I receptors may have the advantage of reduced toxicity or side effects, or greater effectiveness, or both.

Some compounds as described herein may have a high degree of selectivity for BMP vs. TGF-β, Activin, AMP kinase, and VEGF receptor signaling. Other compounds may be less specific and may target other pathways in addition to BMP signaling. In the treatment of tumors, for example, agents which inhibit BMP signaling as well as one or more of the above pathways can have beneficial effects (e.g. decrease tumor size), when molecular phenotyping of specific patients' tumors reveals dysregulation of multiple pathways.

O. Applications of Compounds in Species Other than Human

Compounds as described herein can be used to treat subjects (e.g., humans, domestic pets, livestock, or other animals) by use of dosages and administration regimens that are determined to be appropriate by those of skill in the art, and these parameters may vary depending on, for example, the type and extent of the disorder treated, the overall health status of the subject, the therapeutic index of the compound, and the route of administration. Standard clinical trials can be used to optimize the dose and dosing frequency for any particular pharmaceutical composition of the invention. Exemplary routes of administration that can be used include oral, parenteral, intravenous, intra-arterial, subcutaneous, intramuscular, topical, intracranial, intraorbital, ophthalmic, intraventricular, intracapsular, intraspinal, intracisternal, intraperitoneal, intranasal, aerosol, or administration by suppository. Methods for making formulations that can be used in the invention are well known in the art and can be found, for example, in Remington: The Science and Practice of Pharmacy (20th edition, Ed., A. R. Gennaro), Lippincott Williams & Wilkins, 2000.

P. Combination Therapies

In certain instances BMP antagonists as described herein may be used in combination with other current or future drug therapies, because the effects of inhibiting BMP alone may be less optimal by itself, and/or may be synergistic or more highly effective in combination with therapies acting on distinct pathways which interact functionally with BMP signaling, or on the BMP pathway itself. Some examples of combination therapies could include the following.

Coadministration of erythropoietin (Epogen) and BMP antagonists as described herein may be especially effective for certain types of anemia of inflammation, as described above, particularly in diseases such as end-stage renal disease in which chronic inflammation and erythropoietin insufficiency both act to promote anemia.

Tyrosine kinase receptor inhibitors, such as SU-5416, and BMP antagonists as described herein may have synergistic effects at inhibiting angiogenesis, particularly for anti-angiogenic therapy against tumors. BMP signals (BMP-4) are thought to be critical for the commitment of stem or precursor cells to a hematopoietic/endothelial common progenitor, and may promote the proliferation, survival, and migration of mature endothelial cells necessary for angiogenesis (Park et al. *Development* 131:2749-2762, 2004). Thus antagonism of BMP signals using compounds as described herein may provide additional inhibition of angiogenesis at the level of endothelial precursors and cells. Similarly, co-treatment with BMP antagonists as described herein and other tyrosine kinase receptor inhibitors such as imatinib (Gleevec) could be used to inhibit vascular remodeling and angiogenesis of certain tumors.

The combination of a sonic hedgehog agonist and a BMP antagonist as described herein may be particularly useful for promoting hair growth, as SHH activity is known to stimulate the transition of follicles out of telogen (resting) phase (Paladini et al. *J. Invest. Dermatol.* 125:638-646, 2005), while inhibiting the BMP pathway shortens the telogen phase (Plikus et al. *Nature* 451:340-344, 2008). The use of both would be expected to cause relatively increased time in the anagen or growth phase.

Combined use of Notch modulators (e.g., gamma-secretase inhibitors) and BMP antagonists as described herein may be more effective than either agent alone in applications designed to inhibit vascular remodeling or bone differentiation, because increasing evidence suggests both pathways function cooperatively to effect cell differentiation, and vascular cell migration (Kluppel et al. *Bioessays* 27:115-118, 2005). These therapies may be synergistic in the treatment of tumors in which one or both pathways is deranged (Katoh, *Stem Cell Rev.* 3:30-38, 2007).

Combined use of an Indian Hedgehog (IHH) antagonist and a BMP antagonist as described herein may inhibit pathologic bone formation. IHH is responsible for the commitment of bone precursors to chondrocyte or cartilage forming cells. Endochondral bone formation involves coordinated activity of both chondrogenesis (promoted by BMP signals and IHH signals) and their subsequent calcification by mineralization programs initiated by BMP signals (Seki et al. *J. Biol. Chem.* 279:18544-18549, 2004; Minina et al. *Development* 128: 4523-4534, 2001). Coadministration of an IHH antagonist with a BMP antagonist as described herein, therefore, may be more effective in inhibiting pathological bone growth due to hyperactive BMP signaling (such as in FOP), or in any of the inflammatory or traumatic disorders of pathologic bone formation described above.

Strong experimental evidence exists for an effect of both Smo antagonism and BMP antagonism for treating glioblastoma. Compounds as described herein may be used in combination with Smo antagonists to treat glioblastoma.

Q. Inhibition of BMP Signaling in Insects

Some of the compounds as described herein may have activity against, and perhaps even selectivity for the BMP receptors of arthropods versus those of chordates. Inhibiting BMP signaling in arthropod larvae or eggs is likely to cause severe developmental abnormalities and perhaps compromise their ability to reproduce, e.g., via the same dorsalization that is observed in zebrafish and *drosophila* when this pathway is inhibited. If BMP antagonists as described herein have very strong selectivity for arthropod BMP receptors versus those of humans, they may be used as insecticides or pest control agents that are demonstrably less toxic or more environmentally sound than current strategies.

In addition to being administered to patients in therapeutic methods, compounds as described herein can also be used to treat cells and tissues, as well as structural materials to be implanted into patients (see above), ex vivo. For example, the compounds can be used to treat explanted tissues that may be used, for example, in transplantation.

The invention now being generally described, it will be more readily understood by reference to the following examples which are included merely for purposes of illustration of certain aspects and embodiments of the present invention, and are not intended to limit the invention.

EXEMPLIFICATION

Example 1

Preparation of Substituted Pyrazolo[1,5-a]Pyrimidine Derivatives

The synthesis of substituted pyrazolo[1,5-a]pyrimidine derivatives was carried out according to Scheme 1.

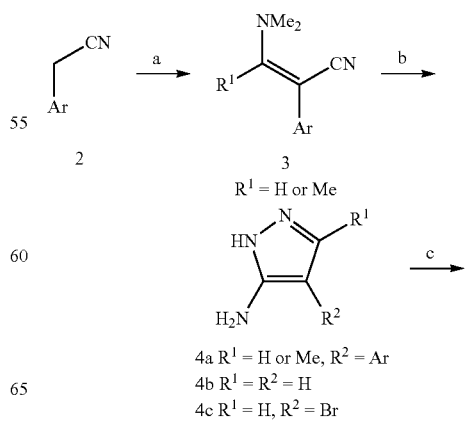

Scheme 1.* General synthesis of substituted pyrazolo[1,5-a]pyrimidine derivatives.

4a R¹ = H or Me, R² = Ar
4b R¹ = R² = H
4c R¹ = H, R² = Br

47

-continued

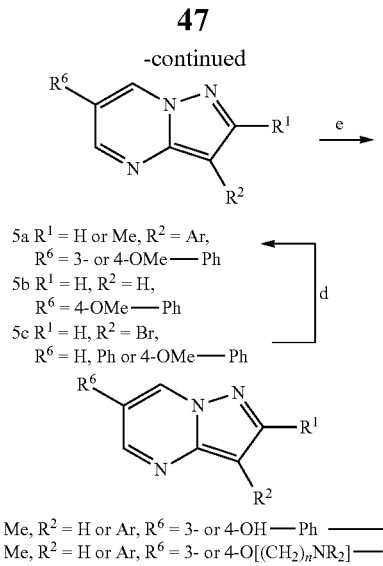

5a R¹ = H or Me, R² = Ar,
R⁶ = 3- or 4-OMe——Ph

5b R¹ = H, R² = H,
R⁶ = 4-OMe——Ph

5c R¹ = H, R² = Br,
R⁶ = H, Ph or 4-OMe——Ph

6 R¹ = H or Me, R² = H or Ar, R⁶ = 3- or 4-OH——Ph
7 R¹ = H or Me, R² = H or Ar, R⁶ = 3- or 4-O[(CH₂)$_n$NR₂]——Ph

*Reagents and conditions: (a) (MeO)₂CHNMe₂ or (MeO)₂CMeNMe₂, Et₃N (for pyridine and quinoline acetonitriles), DMF 110° C., 4-6 h, 100%; (b) NH₂NH₂·HBr, EtOH/H₂O, 110° C., 6 h, 45-80%; (c) ArCH(CHO)₂, AcOH, EtOH, 110° C., 6 h (or MW 170° C., 5 min); (d) ArB(OH)₂, Pd₂(dba)₃, 2-dicyclohexylphosphino-2′,4′,6′triisopropylbiphenyl, K₃PO₄, n-BuOH, MW 150° C., 8 min, 84-90%; (e) HBr/HOAc, MW, 130° C., 8 min, 65-86%; (f) R₂N(CH₂)$_n$Cl·HCl, Cs₂CO₃, NaI (cat), DMF, 60° C., 3 h, (or MW, 140° C., 6 min), 30-75% or Cl(CH₂)$_n$Cl, K₂CO₃, DMF, MW, 140° C., 6 min, then R₂NH, NaI (cat), DMF, MW, 150° C., 10 min, 30-60%.

Arylacetonitriles 2 were allowed to react with dimethylformamide dimethylacetal (DMF-DMA) or dimethyacetamide dimethylacetal (DMA-DMA) to give 3. In the case of pyridine or quinoline acetonitriles, an equivalent of triethylamine was also added. Cyclization of 3 in the presence of hydrazine gave 2-amino-1H-pyrazoles 4a-c. Subsequent condensation with various 2-arylmalondialdehydes in acetic acid and ethanol either under conventional or microwave (MW) heating yielded pyrazolo[1,5-a]pyrimidine derivatives 5a-c. In the case of 5c, palladium-mediated coupling cross-coupling with arylboronic acids gave 5a. This reaction was useful for derivatives where the corresponding arylacetonitriles were not readily available. Dealkylation of the 3- or 4-methoxy groups on the pendent phenyl rings was accomplished with HBr in acetic acid with microwave heating to give 6. Finally, alkylation in one step with R₂N(CH₂)$_n$Cl or in two steps with Cl(CH₂)$_n$Cl followed by an amine gave 7.

Synthesis of 6-(4-Methoxyphenyl)-3-pyridin-4-yl-pyrazolo[1,5-a]pyrimidine (38) and 6-[4-(2-morpholin-4-ylethoxy)phenyl]-3-pyridin-4-yl-pyrazolo[1,5-a]pyrimidine (39) via Scheme 1

To a solution of 4-pyridylacetonitrile hydrochloride (155 mg, 1 mmol) in DMF (0.5 mL) was added dimethylformamide dimethylacetal (2 mL) and triethylamine (0.15 mL, 1.1 eq). The mixture was heated at 110° C. for 9 hours and then concentrated to give 3-dimethylamino-2-pyridin-4-ylacrylonitrile (3, Ar=4-Py) as dark brown crystals and used for the next step without further purification.

Hydrazine hydrobromide (452 mg) was added to 3 (Ar=4-Py, 1 mmol) in mixture of EtOH (2 mL) and H₂O (0.3 mL). The mixture was heated at 110° C. for 5 h. The reaction mixture was diluted with H₂O (0.5 mL) and then Na₂CO₃ was added to until the mixture was basic. The mixture was extracted with EtOAc/EtOH (3:1, 3×2 mL). The organic layer was dried over anhydrous MgSO₄, filtered and concentrated to get 143 mg (89% yield) of 4-pyridin-4-yl-1H-pyrazol-3-ylamine (4a, Ar=4-Py) as a red solid.

48

A solution of 4a (Ar=4-Py) (143 mg, 0.89 mmol) and 2-(4-methoxyphenyl)malondialdehyde (159 mg, 0.89 mmol) in EtOH (1.5 mL) and acetic acid (1.0 mL) was heated at 110° C. for 6 h. Upon cooling the reaction mixture, 38 was obtained as light tan crystals (106 mg, 40%). ¹H NMR (DMSO-d₆) δ 9.72 (d, J=2.2 Hz, 1H), 9.31 (d, J=2.2 Hz, 1H), 9.29 (s, 1H), 8.86 (d, J=6.6 Hz, 2H), 8.73 (d, J=6.6 Hz, 2H), 7.90 (d, J=8.8 Hz, 2H), 7.15 (d, J=8.8 Hz, 2H), 3.85 (s, 3H); HRMS m/z 303.1240 (calc for C₁₈H₁₅N₄O, MH⁺, 303.1241).

A mixture of 38 (197 mg, 0.65 mmol) in acetic acid containing HBr (45% w/w, 2 mL) was heated in a reaction microwave at 130° C. for 10 min. The reaction mixture was triturated with EtOAc and then filtrated to give 6 (R₁=4-Py, R₂=4-OH-Ph, 212 mg, 88%) as a yellow solid.

A mixture of 6 (R₁=4-Py, R₂=4-OH-Ph, 100 mg, 0.35 mmol), 4-(2-chloroethyl)morpholine hydrogen chloride (116 mg, 0.525 mmol), Cs₂CO₃ (570 mg, 1.75 mmol) and a catalytic amount of NaI in DMF (2 mL) was heated at 60° C. for 24 h. The reaction mixture was concentrated and the resulting residue was purified by column chromatography using initially dichloromethane/MeOH as eluent and then dichloromethane/MeOH/Et₃N to give 70 mg, (50% yield) of 39 as yellow solid.

¹H NMR (DMSO-d6) δ 9.73 (d, J=2.2 Hz, 1H), 9.31 (d, J=2.2 Hz, 1H), 9.27 (s, 1H), 8.85 (d, J=6.8 Hz, 2H), 8.69 (d, J=6.8 Hz, 2H), 7.95 (d, J=8.8 Hz, 2H), 7.23 (d, J=8.8 Hz, 2H), 4.47 (t, J=4.6 Hz, 2H), 3.8-3.9 (m, 4H), 3.5-3.6 (m, 6H); HRMS m/z 402.1925 (calc for C₂₃H₂₄N₅O₂, MH⁺, 402.1919).

Synthesis of 6-{4-[2-(4-methylpiperazin-1-yl)ethoxy]phenyl}-3-pyridin-4-yl-pyrazolo[1,5-a]pyrimidine (41) via Scheme 1

A reaction microwave vessel was charged with 6 (R₁=4-Py, R₂=4-OH-Ph, 100 mg, 0.35 mmol), dichloroethane (0.2 mL), K₂CO₃ (240 mg) and DMF (2 mL). The mixture was heated in the microwave reactor at 140° C. for 5 min and then the reaction mixture was filtered. The filtrate was concentrated and then introduced into a reaction microwave vessel along with N-methylpiperazine (0.03 mL), a catalytic amount of NaI and DMF (1 mL). The mixture was heated in the microwave reactor at 150° C. for 15 min and then concentrated. The resulting residue was purified by column chromatography initially using dichloromethane/MeOH as eluent and then dichloromethane/MeOH/Et₃N to give 50 mg (34% yield) of 41 as yellow crystals.

¹H NMR (DMSO-d₆) δ 9.55 (d, J=2.2 Hz, 1H), 9.15 (d, J=2.2 Hz, 1H), 8.99 (s, 1H), 8.61 (dd, J=4.6, 1.6 Hz, 2H), 8.18 (dd, J=4.6, 1.6 Hz, 2H), 7.85 (d, J=8.8 Hz, 2H), 7.13 (d, J=8.8 Hz, 2H), 4.17 (t, J=5.8 Hz, 2H), 2.74 (t, J=5.8 Hz, 2H), 2.28-2.52 (m, 8H), 2.22 (s, 3H); HRMS m/z 415.2241 (calc for C₂₄H₂₇N₆O, MH⁺, 415.2243).

Example 2

Preparation of Other Substituted Pyrazolo[1,5-a]Pyrimidine Derivatives

Two other synthetic routes were subsequently developed for the synthesis of pyrazolo[1,5-a]pyrimidine derivative 13 and other analogs that contained an amine on the 3- or 4-position of the pendent phenyl ring. The first route, depicted in Scheme 2, began in a similar manner as previously described starting with 8, except that 2-(4-bromophenyl)malondialdehyde was used to give 11. Next, a palladium-mediated cross coupling with N-Cbz-piperazine yielded 12. Deprotection hydrogen (1 atm) in the presence of 5% Pd/C gave 13.

Scheme 2.* Synthesis of 13.

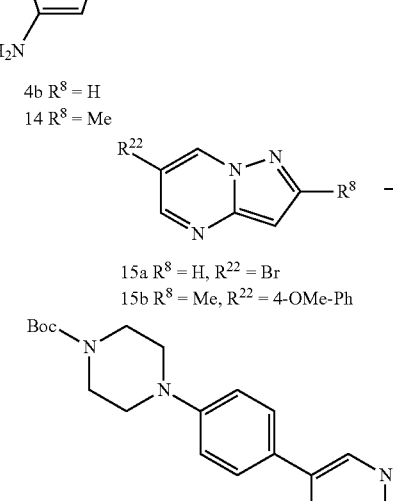

*Reagents and conditions: (a) (MeO)₂CHNMe₂, 110° C., 16 h, 100%; (b) NH₂NH₂·HBr, EtOH/H₂O, 110° C., 4 h, 80%; (c) 4-BrPhCH(CHO)₂, AcOH, EtOH, MW, 170° C., 5 min, 54%; (d) N-Cbz-piperazine, Pd₂(dba)₃, (2-biphenylyl)di-tert-butylphosphine, KO-t-Bu, DME, 100° C., 20 h, 20-30%; (e) H₂ (1 atm), 5% Pd/C (57% H₂O), MeOH/CH₂Cl₂, rt, 4 h, 86%.

Synthesis of 4-[6-(4-Piperazin-1-ylphenyl)pyrazolo[1,5-a]pyrimidin-3-yl]quinoline (13) via Scheme 2

4-Quinolin-4-yl-1H-pyrazol-3-ylamine (10, 210 mg, 1.0 mmol), prepared utilizing Scheme 1, and 2-(4-bromophenyl)malondialdehyde (230 mg, 1.0 mmol) in a mixture of EtOH (1.5 mL) and acetic acid (1 mL) was heated in a microwave reactor at 170° C. for 5 min. The reaction mixture was allowed to cool and then 11 (220 mg, 54% yield) was obtained by filtration as yellow crystals.

N-Cbz-piperazine, (0.15 mL), 11 (100 mg, 0.25 mmol), Pd₂(dba)₃ (10 mg), (2-biphenylyl)di-tert-butylphosphine (6 mg), and KO-t-Bu (42 mg) in dichloroethane (2 mL) was heated at 100° C. under a nitrogen atmosphere for 20 h. The reaction was purified by column chromatography using CH₂Cl₂/EtOAc to give 12 (20 mg, 15%). Next, 5% Pd/C and 12 (20 mg, 0.37 mmol) in a mixture of MeOH (3 mL) and CH₂Cl₂ (2 mL) was de-gassed and then replaced under an atmosphere of hydrogen at rt for 4 h. The reaction mixture was filtered and concentrated to give 13 (13 mg, 86%). ¹H NMR (DMSO-d₆) δ 9.75 (d, J=2.2 Hz, 1H), 9.40 (br.s, 1H), 9.29 (d, J=5.9 Hz, 1H), 9.28 (d, J=2.2 Hz, 1H), 9.07 (s, 1H), 8.70 (d, J=8.4 Hz, 1H), 8.51 (d, J=5.9 Hz, 1H), 8.47 (d, J=8.4 Hz, 1H), 8.21 (t, J=7.6 Hz, 1H), 7.99 (t, J=7.6 Hz, 1H), 7.88 (d, J=8.8 Hz, 2H), 7.19 (d, J=8.8 Hz, 2H), 3.51-3.58 (m, 4H), 3.20-3.30 (m, 4H).

Example 3

Alternative Preparation of Other Substituted Pyrazolo[1,5-a]Pyrimidine Derivatives The second alternate route to 13, depicted in Scheme 3, began with 2-amino-1H-pyrazole, 4b, which was allowed to react with 2-bromomalondialdehyde to give 6-bromopyrazolo[1,5-a]pyrimidine, 15a. A palladium-mediated cross coupling with 4-4-(tert-butoxycarbonyl)-piperazin-1-ylphenylboronic acid pinacol ester yielded 16. Next, a regioselective bromination of the C-3 carbon with N-bromosuccinimide (NBS) in dichloromethane at room temperature gave 17a in 79% yield. Palladium-mediated cross coupling of this aryl bromide with quinoline-4-boronic acid produced 18a in a moderate 46% yield. Finally, deprotection with 4 N HCl in dioxane and methanol gave 13 as the hydrochloride salt. This method was also used to prepare several other derivatives, including 18c that contains a C-2 substituent.

Scheme 3.* Alternative sysnthesis of 13.

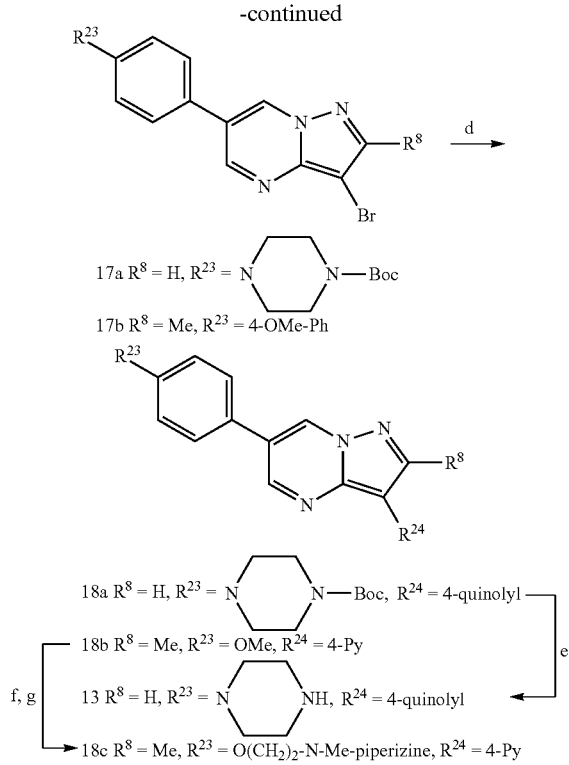

*Reagents and conditions: (a) BrCH(CHO)₂ (or 4-OMePhCH(CHO)₂ for 15b) AcOH, EtOH, 80° C., 7 h, 49%; (b) B(O[C(CH₃)₂]₂O)-4-Ph-N-Boc-piperazine, Pd(PPh₃)₄, K₂CO₃, dioxane/H₂O, MW, 150° C., 8 min, 90% (or 110° C., 3 h, 86%); (c) NBS, CH₂Cl₂, rt, 5 h, 79%; (d) quinoline-4-boronic acid, Pd₂(dba)₃, 2-dicyclohexylphosphino-2′,4′,6′-triisopropylbiphenyl, K₃PO₄, n-BuOH, MW, 150° C., 15 min, 46%; (e) 4 N HCl in 1,4-dioxane, MeOH, rt, 24 h, 95%; (f) HBr/HOAc, MW, 130° C., 8 min, 81%; (g) Cl(CH₂)₂Cl, K₂CO₃, DMF, MW, 140° C., 6 min, then N-Me-piperizine, NaI (cat), DMF, MW 150° C., 10 min, 57%.

Synthesis of 4-[6-(4-Piperazin-1-ylphenyl)pyrazolo[1,5-a]pyrimidin-3-yl]quinoline hydrochloride salt (13.HCl)

A mixture of 2-bromomalondialdehyde (1.5 g, 10 mmol) and 1H-pyrazol-3-ylamine (4b, 0.83 g, 10 mmol) in a mixture of EtOH (15 mL) and acetic acid (5 mL) was heated at 80° C. for 1.5 h. The reaction mixture was concentrated and the resulting residue purified by column chromatography using hexane/EtOAc (5:1) to give 15a (1.15 g, 58% yield) as light yellow crystals.

The mixture of 15a (0.87 g, 4.39 mmol), 4-[4-(tert-butoxycarbonyl)piperazin-1-yl]phenylboronic acid pinacol ester (1.7 g, 4.39 mmol), Pd(Ph₃P)₄ (0.5 g, 0.439 mmol), K₂CO₃ (1.82 g, 13.17), 1,4-dioxane (15 mL) and H₂O (5 mL) was heated at 110° C. under a nitrogen atmosphere for 5 h in a sealed vial. The reaction mixture was concentrated and the residue was purified by column chromatography using CH₂Cl₂/EtOAc to give 16 (1.4 g, 86% yield). ¹H NMR (CDCl₃) δ 8.82 (dd, J=2.2, 0.7 Hz, 1H), 8.77 (d, J=2.2 Hz, 1H), 8.16 (d, J=2.2 Hz, 1H), 7.54 (d, J=8.8 Hz, 2H), 7.08 (d, J=8.8 Hz, 2H), 6.75 (dd, J=2.2, 0.7 Hz, 1H), 3.63-3.67 (m, 4H), 3.25-3.28 (m, 4H), 1.53 (s, 9H).

To a solution of 16 (1.95 g, 1.2 mmol) in CH₂Cl₂ (20 mL) at 0° C. was drop-wise added NBS (225 mg, 1.05 eq) in CH₂Cl₂ (10 mL). The resulting mixture was then stirred at 0° C. for 5 h and then washed with H₂O (6 mL×2). The organic layer was dried over anhydrous Na₂SO₄, filtered, and concentrated to 17a (1.36 g, 79% yield) as off-white crystals. ¹H NMR (CDCl₃) δ 8.72 (d, J=2.2 Hz, 1H), 8.66 (d, J=2.2 Hz, 1H), 8.05 (s, 1H), 7.43 (d, J=8.8 Hz, 2H), 6.98 (d, J=8.8 Hz, 2H), 3.52-3.58 (m, 4H), 3.15-3.20 (m, 4H), 1.43 (s, 9H).

A microwave reaction vial was charged with 17a (240 mg, 0.52 mmol), 4-quinoline boronic acid (135 mg, 0.78 mmol), Pd₂(dba)₃ (18 mg), 2-dicyclohexylphosphino-2′,4′,6′-triisopropylbiphenyl (18 mg), K₃PO₄ (240 mg), and n-BuOH (4 mL). The mixture was de-gassed, placed under an atmosphere of nitrogen and heated in a microwave reactor at 150° C. for 15 min. The reaction mixture was filtered and washed with CH₇Cl₂. The filtrate was concentrated and the resulting residue purified by column chromatography to give 18a (141 mg, 46% yield) as light yellow crystals. ¹H NMR (CDCl₃) δ 9.17 (d, J=4.5 Hz, 1H), 9.07 (d, J=2.2 Hz, 1H), 9.02 (d, J=2.2 Hz, 1H), 8.68 (s, 1H), 8.30-8.36 (m, 2H), 7.95 (dd, J=7.0, 1.3 Hz, 1H), 7.92 (d, J=4.5 Hz, 1H), 7.68-7.76 (m, 3H), 7.24 (d, J=8.8 Hz, 2H), 3.74-3.82 (m, 4H), 3.40-3.48 (m, 4H), 1.66 (s, 9H).

A mixture of 18a (640 mg, 1.26 mmol) in MeOH (10 mL) and HCl in 1,4-dioxane (4M, 6.3 mL) was stirred at rt for 24 h before being concentrated to dryness. The residue was washed with a small amount of MeOH to give 13.HCl (550 mg, 98% yield) as a yellow solid. NMR (DMSO-d₆) δ 9.75 (d, J=2.2 Hz, 1H), 9.40 (br.s, 1H), 9.29 (d, J=5.9 Hz, 1H), 9.28 (d, J=2.2 Hz, 1H), 9.07 (s, 1H), 8.70 (d, J=8.4 Hz, 1H), 8.51 (d, J=5.9 Hz, 1H), 8.47 (d, J=8.4 Hz, 1H), 8.21 (t, J=7.6 Hz, 1H), 7.99 (t, J=7.6 Hz, 1H), 7.88 (d, J=8.8 Hz, 2H), 7.19 (d, J=8.8 Hz, 2H), 3.51-3.58 (m, 4H), 3.20-3.30 (m, 4H); HRMS m/z 407.1979 (calc for C₂₅H₂₃N₆, MH⁺, 407.1979).

Example 4

Preparation of Pyrrolo[1,2-a]Pyrimidine Derivatives

The synthesis of pyrrolo[1,2-a]pyrimidine derivatives is illustrated in Scheme 4.

Scheme 4*. Synthesis of pyrrolo[1,2-a]pyrimidine derivatives.

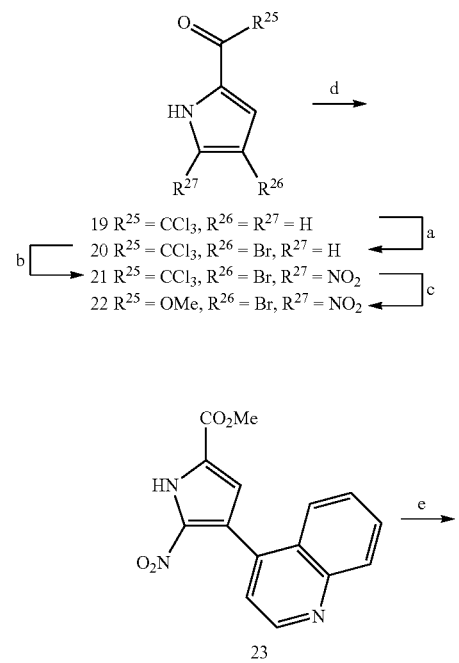

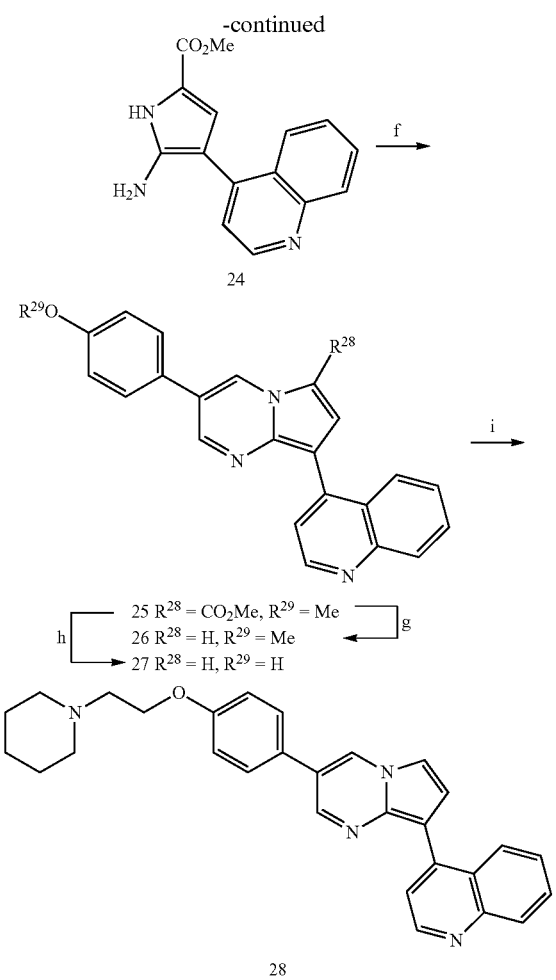

*Reagents and conditions: (a) Br₂, ChCl₃, 0° C., 57%; (b) HNO₃ (70%), Ac₂O, -40° C. to rt, 40%; (c) NaOMe, MeOH, rt, 99%; (d) quinoline-4-boronic acid, Pd(PPh₃)₄, Na₂CO₃, 1,4-dioxane, reflux 16 h, 60%; (e) H₂ (1 atm), 10% Pd/C, MeOH, rt, 0.5 h; (f) 4-MeOPhCH(CHO)₂, AcOH, EtOH, reflux, 16 h, 73%; (g) 40% aqueous H₂SO₄, 110° C., 2 h, 91%; (h) 40% aqueous H₂SO₄, 110° C., 2 d, 71%; (i) piperidyl-N-CH₂CH₂Cl•HCl, 60% NaH, DMF, rt, 24 h, 80%.

Regioselective bromination of 2-trichloromethylketopyrrole, 19, was achieved in the presence of bromine to give 20 (see *J. Chem. Soc., Perkin Trans.* 1, 1443-1447, 1997). Regioselective nitration with concentrated nitric acid gave 21 (see *Helv. Chim. Acta* 85:4485-4517, 2002). This compound was allowed to react with sodium methoxide in methanol to give methyl ester 22. Palladium-mediated cross coupling of this pyrrole bromide with quinoline-4-boronic acid produced 23 (see *Bioorg. Med. Chem. Lett.* 12:2767-2770, 2002). Reduction of the nitro group hydrogen (1 atm) in the presence of 10% Pd/C gave 24, which was used immediately in the next reaction without purification. Condensation with 2-(4-methoxyphenyl)malondialdehyde in acetic acid and ethanol yielded pyrrolo[1,2-a]pyrimidine derivative 25. Heating this material at 110° C. in aqueous sulfuric acid for 2 h gave 26 via ester hydrolysis and subsequent decarboxylation (see *J. Med. Chem.* 44:2691-2694, 2001). Prolonged heating of 25 for 2 d resulted in ether hydrolysis producing 27. Finally, alkylation of the phenol gave 28.

Synthesis of 4-Bromo-2-trichloroacetylpyrrole (20) via Scheme 4

Bromine (2.12 g, 10 mmol) was added dropwise to a stirred solution of 2-trichloroacetylpyrrole (19, 1.71 g, 10.7 mmol) in CHCl₃ (15 mL) at 0° C. The mixture was then stirred at 0° C. for 20 min and at rt for 5 min before quenched with water. The organic layer was washed with sat. NaHCO₃ and water, dried (MgSO₄) and concentrated. The residue was purified by chromatography on silica gel using hexane/ethyl acetate (90:10 to 75:25) to give 20 as a white solid (1.65 g, 57%). ¹H NMR (CDCl₃, 500 MHz) δ 9.21 (br. s, 1H), 7.35 (dd, J=1.5, 2.5 Hz, 1H), 7.15 (dd, J=1.5, 2.5 Hz, 1H); mp 135-137° C. (lit.,[16] 136-138° C.).

Synthesis of 4-Bromo-5-nitro-2-trichloroacetylpyrrole (21) via Scheme 4

A solution of 4-bromo-2-trichloroacetylpyrrole (20, 873 mg, 3.0 mmol) in Ac₂O (7 mL) was cooled to -40° C. and treated dropwise with 70% nitric acid (0.24 mL, 3.0 mmol). The mixture was allowed to warm up to rt over 2 h before quenched with ice-water, and then extracted with ethyl acetate. The organic layer was washed with sat. NaHCO₃ and water, dried (Na₂SO₄) and concentrated. The residue was purified by column chromatography on silica gel using CH₂Cl₂/MeOH (95:5) to give 21 as a pale yellow solid (404 mg, 40%). ¹H NMR (CDCl₃, 500 MHz) δ 7.38 (s, 1H); mp 125-126° C.

Synthesis of Methyl 4-bromo-5-nitro-1H-pyrrole-2-carboxylate (22) via Scheme 4

4-Bromo-5-nitro-2-trichloroacetylpyrrole (21, 80 mg, 0.24 mmol) was added to 0.5 M MeONa in MeOH (1 mL) at rt. The reaction mixture was stirred at rt for 2 h, then quenched with H₂SO₄ at 0° C., followed by addition of ice-water, and extracted with ethyl acetate. The organic layer was washed with water, dried (Na₂SO₄) and concentrated to give 22 as a yellow solid (60 mg, 99%). ¹H NMR (DMSO-d₆, 500 MHz) δ 6.66 (s, 1H), 3.67 (s, 3H); mp >255° C.

Synthesis of Methyl 5-nitro-4-quinolin-4-yl-1H-pyrrole-2-carboxylate (23) via Scheme 4

A mixture of methyl 4-bromo-5-nitro-1H-pyrrole-2-carboxylate (22, 124 mg, 0.5 mmol), quinoline-4-boronic acid (174 mg, 1.0 mmol), Pd (PPh₃)₄ (116 mg, 0.1 mmol), 2.0 M Na₂CO₃ (0.5 mL), and 1,4-dioxane (6 mL) was stirred overnight at 101° C., then cooled to rt, diluted with water, and extracted with ethyl acetate. The organic phase was washed with water, dried (Na₂SO₄) and concentrated. The residue was purified by column chromatography on silica gel using CH₂Cl₂/MeOH (95:5) to give 23 as a yellow solid (90 mg, 60%). ¹H NMR (DMSO-d₆, 500 MHz) δ 14.5 (br.s, 1H), 8.95 (d, J=4.5 Hz, 1H), 8.10 (d, J=3.5 Hz, 1H), 7.79 (m, 1H), 7.68 (d, J=3.5 Hz, 1H), 7.56 (m, 1H), 7.53 (d, J=4.5 Hz, 1H), 7.07 (s, 1H), 3.89 (s, 3H); mp 204-205° C.

Synthesis of Methyl 3-(4-methoxyphenyl)-8-quinolin-4-yl-pyrrolo[1,2a]pyrimidine-6-carboxylate (25) via Scheme 4

A mixture of methyl 5-nitro-4-quinolin-4-yl-1H-pyrrole-2-carboxylate (23, 90 mg, 0.3 mmol), Pd/C (5%, 45 mg), and MeOH (15 mL) was stirred under argon for 5 min, then under hydrogen for 40 min before removal of the catalyst by filtration through celite. To the orange color filtrate was added 2-(4-methoxyphenyl)malondialdehyde (54 mg, 0.3 mmol) followed by AcOH (2 mL). The resulting reaction mixture was stirred overnight at 82° C., then cooled to rt, quenched with sat. NaHCO$_3$, and extracted with ethyl acetate and CH$_2$Cl$_2$. The combined organic layers were dried over Na$_2$SO$_4$, filtered, and concentrated. The residue was purified by column chromatography on silica gel using CH$_2$Cl$_2$/MeOH (90:10) to give 25 as a yellow solid (90 mg, 73%). $^1$H NMR (DMSO-d$_6$, 500 MHz) δ 9.80 (d, J=3.0 Hz, 1H), 8.97 (d, J=5.0 Hz, 1H), 8.87 (d, J=3.0 Hz, 1H), 8.10 (m, 1H), 8.04 (s, 1H), 7.80 (m, 1H), 7.75 (d, J=5.0 Hz, 1H), 7.75 (d, J=8.5 Hz, 2H), 7.61 (m, 1H), 7.15 (d, J=8.5 Hz, 2H), 3.94 (s, 3H), 3.84 (s, 3H); mp 230-231° C.

Synthesis of 4-[3-(4-Methoxyphenyl)pyrrolo[1,2-a]pyrimidin-8-yl]quinoline (26) via Scheme 4

Conc. H$_2$SO$_4$ (1 mL) was added slowly to 1.5 mL of H$_2$O at 0° C. and the resulting solution was added to 25 (10 mg, 0.025 mmol). The mixture was heated to 110° C. and stirred for 4 h before cooled down to rt, then quenched slowly with saturated NaHCO$_3$, and extracted with ethyl acetate/MeOH (95:5). The combined organic layers were concentrated and the residue was purified by column chromatography on silica gel using CH$_2$Cl$_2$/MeOH (95:5) as eluant to give 26 as a brown solid (8 mg, 91%). $^1$H NMR (CDCl$_3$, 400 MHz) δ 8.98 (d, J=4.4 Hz, 1H), 8.48 (d, J=2.0 Hz, 1H), 8.40 (d, J=2.8 Hz, 1H), 8.27 (d, J=8.4 Hz, 1H), 8.19 (d, J=8.4 Hz, 1H), 7.77-7.74 (m, 2H), 7.72-7.52 (m, 3H), 7.45 (d, J=3.2 Hz, 1H), 7.34 (d, J=2.8 Hz, 1H), 7.07 (d, J=8.4 Hz, 2H), 3.90 (s, 3H); mp 144-145° C.

Synthesis of 4-(8-Quinolin-4-yl-pyrrolo[1,2-a]pyrimidin-3-yl)-phenol (27) via Scheme 4

Conc. H$_2$SO$_4$ (2 mL) was added slowly to 3 mL of H$_2$O at 0° C. and the resulting solution was added to 25 (41 mg, 0.1 mmol). The mixture was heated to 110° C. and stirred for 2 days before cooled down to rt, then quenched slowly with sat. NaHCO$_3$, and extracted with ethyl acetate/MeOH (95:5). The combined organic layers were concentrated and the residue was purified by column chromatography on silica gel using CH$_2$Cl$_2$/MeOH (95:5) as eluant to give 27 as a yellow solid (24 mg, 71%). $^1$H NMR (DMSO-d$_6$, 400 MHz) δ 9.75 (br.s, 1H), 9.05 (d, J=2.4 Hz, 1H), 8.89 (d, J=4.8 Hz, 1H), 8.53 (d, J=2.4 Hz, 1H), 8.22 (d, J=8.0 Hz, 1H), 8.05 (d, J=8.0 Hz, 1H), 7.77-7.71 (m, 3H), 7.59-7.55 (m, 3H), 7.36 (d, J=2.8 Hz, 1H), 6.90 (d, J=8.8 Hz, 2H); mp >255° C.

Synthesis of 4-{3-[4-(2-Piperidin-1-ylethoxy)phenyl]pyrrolo[1,2-a]pyrimidin-8-yl}quinoline (28) via Scheme 4

To a solution of 27 (20 mg, 0.06 mmol) under an argon atmosphere in 3 mL of DMF was added NaH (60%, 8 mg, 0.2 mmol) followed by N-(2-chloroethyl)piperidine hydrochloride (18 mg, 0.1 mmol). The mixture was stirred at rt for 1 clay, then quenched with H$_2$O, and extracted with ethyl acetate. The organic layer was separated and concentrated. The residue was purified by column chromatography on silica gel using CH$_7$Cl$_2$/MeOH (88:12) to give 28 as a brown oil (15 mg, 80%) and 7 mg of recovered starting material. $^1$H NMR (CDCl$_3$, 500 MHz) δ 8.97 (d, J=4.5 Hz, 1H), 8.46 (d, J=2.0 Hz, 1H), 8.38 (d, J=2.5 Hz, 1H), 8.25 (d, J=8.5 Hz, 1H), 8.19 (d, J=8.0 Hz, 1H), 7.77-7.71 (m, 2H), 7.54-7.50 (m, 3H), 7.43 (d, J=3.0 Hz, 1H), 7.32 (d, J=3.0 Hz, 1H), 7.04 (d, J=9.0 Hz, 2H), 4.27 (t, J=5.5 Hz, 2H), 3.00 (m, 2H), 2.74 (m, 4H), 1.73 (m, 4H), 1.52 (m, 2H).

Example 5

Preparation of Pyrazolo[1,5-a]Pyridine Derivatives

The synthesis of pyrazolo[1,5-a]pyridine derivatives is outlined in Scheme 5.

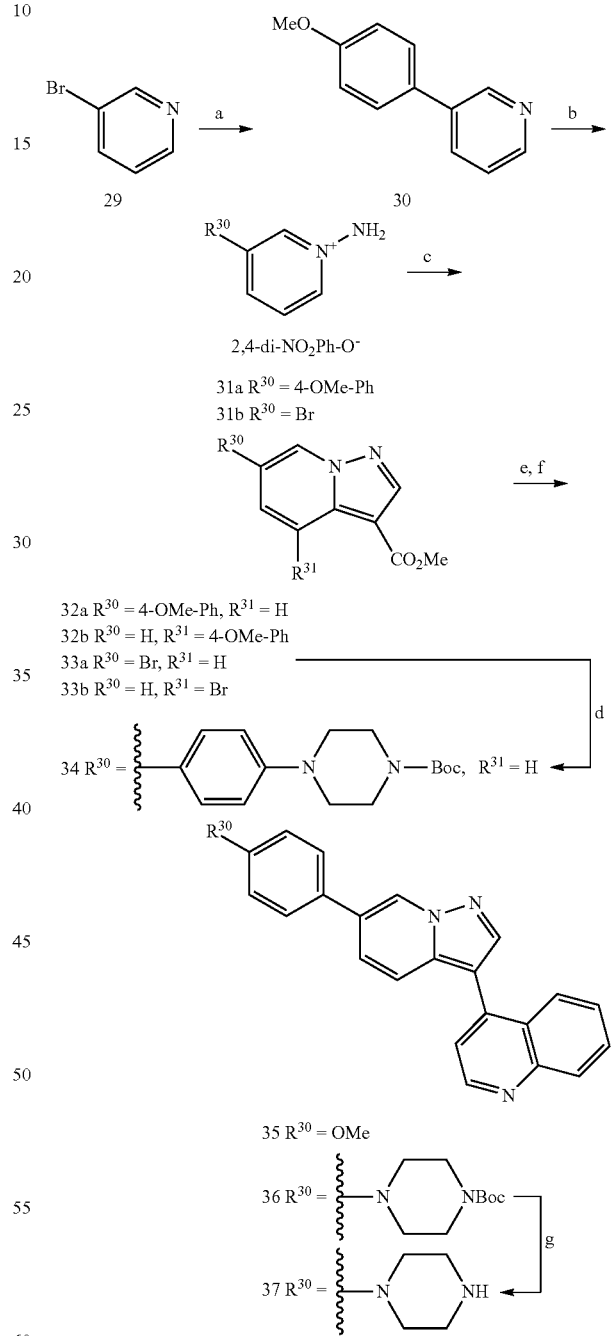

Scheme 5.* Synthesis of pyrazolo[1,5-a]pyridine derivatives.

*Reagents and conditions: (a) 4-MeOPhB(OH)$_2$, Pd(PPh$_3$)$_4$, K$_3$PO$_4$, 1,4-dioxane, 100° C., 18 h, 58%; (b) 2,4-di-NO$_2$PhONH$_2$, CH$_3$CN, 40° C., 20 h; (c) HC≡CCO$_2$Me, K$_2$CO$_3$, DMF, rt, 33-37% over two steps (32a:32b and 33a:33b ~ 1:2); (d) B(O[C(CH$_3$)$_2$]$_2$O)-4-Ph-N-Boc-piperazine, Pd(PPh$_3$)$_4$, K$_2$CO$_3$, 1,4-dioxane/H$_2$O, 110° C., 5 h, 73%; (e) NaOH, EtOH/H$_2$O (6:1), Δ, 3 h; (f) 4-bromoquinoline, Pd(acac)$_2$, CuI, K$_2$CO$_3$, 1,10-phenanthroline, 4Å MS, NMP, 165° C., 24 h, 10-22% (over two steps); (g) 4 N HCl in 1,4-dioxane, MeOH, rt, 24 h.

A palladium-mediated cross coupling of this 3-bromopyridine, 29, with 4-methoxyphenylboronic acid produced 30 in 58% yield (see *Synlett,* 2005, 2057-2061). This pyridine derivative was converted to 1-aminopyridine salt 31a utilizing O-(2,4-dinitrophenyl)hydroxylamine. Cyclization of 31a upon treatment with methyl propiolate gave regioisomers 32a and 32b in a 1:2 ratio and a combined yield of 33% over two steps (see *J. Chem. Soc., Perkin Trans. 1* 406-409, 1975). In a similar manner, 29 was converted to 33a and 33b (1:2 ratio) in 37% yield, via intermediate 31b. Compound 33a was further converted to 34 via a palladium-mediated coupling. Then, 32a and 34 were hydrolyzed with aqueous sodium hydroxide and the resulting carboxylic acids were subjected to palladium- and copper-mediated decarboxylative couplings with 4-bromoquinoline in the presence of $Pd(acac)_2$ and CuI producing 35 and 36, respectively. Finally, exposure of 36 to 4 N HCl in 1,4-dioxane resulted in removal of the tert-butyl carbamate yielding 37 as the hydrochloride salt.

Synthesis of 3-(4-Methoxyphenyl)pyridine (30) via Scheme 5

A mixture of 3-bromopyridine, (29, 190 mg, 1.20 mmol), 4-methoxyphenylboronic acid (152 mg, 1.00 mmol), $Pd(PPh_3)_4$ (35.0 mg, 0.0300 mmol) and $K_3PO_4$ (430 mg, 2.00 mmol) in 1,4-dioxane (10 mL) was heated at 100° C. for 18 h. The solvent was removed under reduced pressure and ethyl acetate was added to the solid residue. The organic layer was washed sequentially with water, brine, and then dried over anhydrous $Na_2SO_4$. Concentration of the filtrate followed by chromatography [silica, hexanes/ethyl acetate (3:1)] gave 30 as a white solid (108 mg, 58% yield), mp 61-63° C. $^1$H NMR (500 MHz, $CDCl_3$) δ 3.86 (s, 3H), 7.01 (d, J=8.5 Hz, 2H), 7.33 (dd, J=5.0, 8.0 Hz, 1H), 7.52 (d, J=8.5 Hz, 2H), 7.81-7.83 (m, 1H), 8.54 (dd, J=2.0, 5.0 Hz, 1H), 8.81 (br s, 1H).

Synthesis of Methyl 6-(4-methoxyphenyl)pyrazolo [1,5-a]pyridine-3-carboxylate (32a) and methyl 4-(4-methoxyphenyl)pyrazolo[1,5-a]pyridine-3-carboxylate (32b) via Scheme 5

A mixture of 30 (545 mg, 3.00 mmol) and 2,4-di-$NO_2PhONH_2$ (645 mg, 3.25 mmol) in $CH_3CN$ (2 mL) was stirred at 40° C. for 20 h. The reaction mixture was concentrated and the resulting residue was triturated with $Et_2O$ (3×10 mL) to give 31a as a yellow solid, which was dried under vacuum and used in the next step without further purification. To a mixture of 31a in DMF (6 mL) at 0° C. were added $K_2CO_3$ (620 mg, 4.50 mmol) and methyl propiolate (378 mg, 4.50 mmol). The mixture was stirred vigorously at room temperature for 18 h and then the solvent was removed under reduced pressure to obtain a dark brown residue. The residue was dissolved in $CHCl_3$ and the insoluble material was removed by filtration. Concentration of the filtrate followed by chromatography [silica, hexanes/ethyl acetate (3:1)] gave 32a as a white solid (90 mg, 10% yield) and 32b as a pale yellow solid (200 mg, 23% yield). 32a: mp 162-164° C.; $^1$H NMR (500 MHz, $CDCl_3$) δ 3.87 (s, 3H), 3.93 (s, 3H), 7.02 (d, J=8.0 Hz, 2H), 7.53 (d, J=8.0 Hz, 2H), 7.65 (dd, J=2.0, 9.5 Hz, 1H), 8.18 (d, J=9.5 Hz, 1H), 8.40 (s, 1H), 8.67 (br s, 1H). 32b: $^1$H NMR (500 MHz, $CDCl_3$) δ 3.39 (s, 3H), 3.87 (s, 3H), 6.96 (d, J=8.5 Hz, 2H), 7.00 (t, J=7.0 Hz, 1H), 7.24 (d, J=7.0 Hz, 1H), 7.32 (d, J=8.5 Hz, 2H), 8.43 (s, 1H), 8.52 (d, J=7.0 Hz, 1H).

Synthesis of 4-[6-(4-Methoxyphenyl)pyrazolo[1,5-a] pyridin-3-yl]quinoline (35) via Scheme 5

To a stirred suspension of 32a (195 mg, 0.690 mmol) in EtOH (6 mL) was added a solution of NaOH (97.0 mg, 2.40 mmol) in $H_2O$ (1 mL) and the resulting suspension was heated at reflux for 3 h. The reaction mixture became a clear solution at elevated temperature. The solvent was completed evaporated under reduced pressure and the solid residue was acidified with 1 N HCl at 0° C. The corresponding acid precipitated as a white solid. This solid was collected by filtration, dried under vacuum overnight and used without further purification. A heterogeneous mixture of the crude acid, $K_2CO_3$ (55 mg, 0.40 mmol) and 4 Å molecular sieves (100 mg) in NMP (2 mL) under an argon atmosphere was heated at 50-60° C. for 30 min. Then 4-bromoquinoline (62 mg, 0.30 mmol), palladium acetylacetonate (2.0 mg, 0.0065 mmol), copper(I) iodide (4.0 mg, 0.021 mmol) and 1,10-phenantholine (6.0 mg, 0.033 mmol) were added to the reaction mixture sequentially at rt. The reaction mixture was then heated at 165° C. for 24 h. The solvent was concentrated and $CH_2Cl_2$ was added to the residue. The heterogeneous mixture was filtered and the filtrate was washed sequentially with water, brine, and then dried over anhydrous $Na_2SO_4$. Filtration and concentration followed by chromatography of the crude mixture on silica gel using hexane/ethyl acetate (1:1) gave 35 as a pale yellow solid (24 mg, 22% yield): mp 150-152° C.; $^1$H NMR (500 MHz, DMSO-$d_6$) δ 3.82 (s, 3H), 7.08 (d, J=9.0 Hz, 2H), 7.61-7.66 (m, 2H), 7.71-7.74 (m, 2H), 7.78 (d, J=9.0 Hz, 2H), 7.79-7.85 (m, 1H), 8.15 (d, J=9.5 Hz, 1H), 8.18 (d, J=9.5 Hz, 1H), 8.46 (s, 1H), 8.90 (d, J=9.5 Hz, 1H), 9.18 (s, 1H); HRMS m/z 352.1444 (calc for $C_{23}H_{18}N_3O$, $MH^+$, 352.1445).

Synthesis of Methyl 6-bromopyrazolo[1,5-a]pyridine-3-carboxylate (33a) and methyl 4-bromopyrazolo[1,5-a]pyridine-3-carboxylate (33b) via Scheme 5

Following the procedures described above, 33a and 33b were prepared from 29 in 11% and 26% yields, respectively. 33a: mp 116-118° C.; $^1$H NMR (500 MHz, $CDCl_3$) δ 3.92 (s, 3H), 7.48 (dd, J=1.5, 9.5 Hz, 1H), 8.07 (d, J=9.5 Hz, 1H), 8.36 (s, 1H), 8.68 (br s, 1H). 33b: $^1$H NMR (500 MHz, $CDCl_3$) δ 3.91 (s, 3H), 6.82 (t, J=7.0 Hz, 1H), 7.65 (d, J=7.0 Hz, 1H), 8.43 (s, 1H), 8.53 (d, J=7.0 Hz, 1H).

Synthesis of Methyl 6-(4-piperazin-1-ylphenyl)pyrazolo[1,5-a]pyridine-3-carboxylate (34) via Scheme 5

To a stirring solution of 33a (128 mg, 0.500 mmol) and tort-butyl 4-[4-(4,4,5,5-tetramethyl-1,3,2-dioxaborolan-2-yl)phenylpiperazinecarboxylate (233 mg, 0.600 mmol) in dioxane (5 mL) was added an aqueous solution of $K_2CO_3$ (104 mg, 0.750 mmol) (dissolved in minimum amount of water) followed by $Pd(PPh_3)_4$ (29.0 mg, 0.0250 mmol) and the homogeneous mixture was heated at 110° C. for 5 h. The solvent was removed under reduced pressure and excess $CH_2Cl_2$ was added to the solid residue. The organic layer was washed with water (3×10 mL), brine, and dried over $Na_2SO_4$. Concentration of the filtrate followed by chromatography [silica, hexanes/ethyl acetate (3:2)] gave 34 as a pale yellow solid (160 mg, 73% yield), mp 211-213° C.; $^1$H NMR (500 MHz, $CDCl_3$) δ 1.50 (s, 9H), 3.21-3.23 (m, 4H), 3.60-3.62 (m, 4H), 3.93 (s, 3H), 7.03 (d, J=9.0 Hz, 2H), 7.52 (d, J=9.0 Hz, 2H), 7.66 (dd, J=2.0, 9.0 Hz, 1H), 8.18 (d, J=9.0 Hz, 1H), 8.40 (s, 1H), 8.67 (s, 1H).

Synthesis of N-Boc-4-[6-(4-Piperazin-1-ylphenyl) pyrazolo[1,5-a]pyridin-3-yl]-quinoline (36) via Scheme 5

Following a procedure described above for 35, compound 36 was prepared from 34 in 10% yield: mp 198-200° C.; $^1$H NMR (500 MHz, CDCl$_3$) δ 1.52 (s, 9H), 3.22-3.24 (m, 4H), 3.61-3.63 (m, 4H), 7.03 (d, J=9.0 Hz, 2H), 7.44-7.50 (m, 2H), 7.53-7.56 (m, 3H), 7.65-7.69 (m, 1H), 7.75-7.79 (m, 1H), 8.10 (d, J=8.0 Hz, 1H), 8.21 (d, J=8.0 Hz, 1H), 8.25 (s, 1H), 8.75 (br s, 1H), 8.96 (d, J=9.5 Hz, 1H).

Synthesis of 4-[6-(4-Piperazin-1-ylphenyl)pyrazolo[1,5-a]pyridin-3-yl]-quinoline (37) via Scheme 5

A stirred suspension of 36 (37 mg, 0.073 mmol) in MeOH (2.5 mL) was treated with 4 N HCl in dioxane (0.25 mL, 0.60 mmol) dropwise at room temperature. A clear solution was developed after 10-15 min, which was then stirred at room temperature for 24 h. The solvent was concentrated under reduced pressure to obtain a yellow solid. The solid was dissolved in MeOH (3 mL) and the heterogeneous mixture was filtered off. Concentration of the filtrate followed by reverse-phase HPLC purification gave 37 as a yellow solid (4 mg, 12% yield): $^1$H NMR (500 MHz, CDCl$_3$) δ 3.22-3.40 (m, 8H), 7.12 (d, J=9.0 Hz, 2H), 7.63-7.67 (m, 2H), 7.70-7.73 (m, 2H), 7.76 (d, J=9.0 Hz, 2H), 7.83 (d, J=8.0 Hz, 1H), 8.10 (d, J=8.0 Hz, 1H), 8.12 (d, J=8.0 Hz, 1H), 8.46 (s, 1H), 8.96 (d, J=5.0 Hz, 1H), 9.16 (s, 1H); HRMS m/z 406.2026 (calc for C$_{26}$H$_{24}$N$_5$, MH$^+$, 406.2030).

Example 6

Preparation of 4-(6-(4-(4-methoxypiperidin-4-yl)phenyl)pyrazolo[1,5-a]pyrimidin-3-yl)quinoline (44)

The synthesis of 4-(6-(4-(4-methoxypiperidin-4-yl)phenyl)pyrazolo[1,5-a]pyrimidin-3-yl)quinoline (44) is outlined in Scheme 6.

Scheme 6. Synthesis of 4-(6-(4-(4-methoxypiperidin-4-yl)phenyl)pyrazolo[1,5-a]pyrimidin-3-yl)quinoline (44).

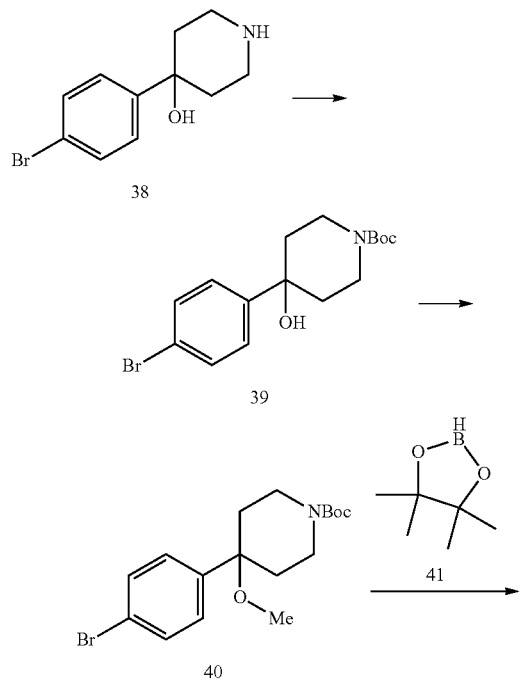

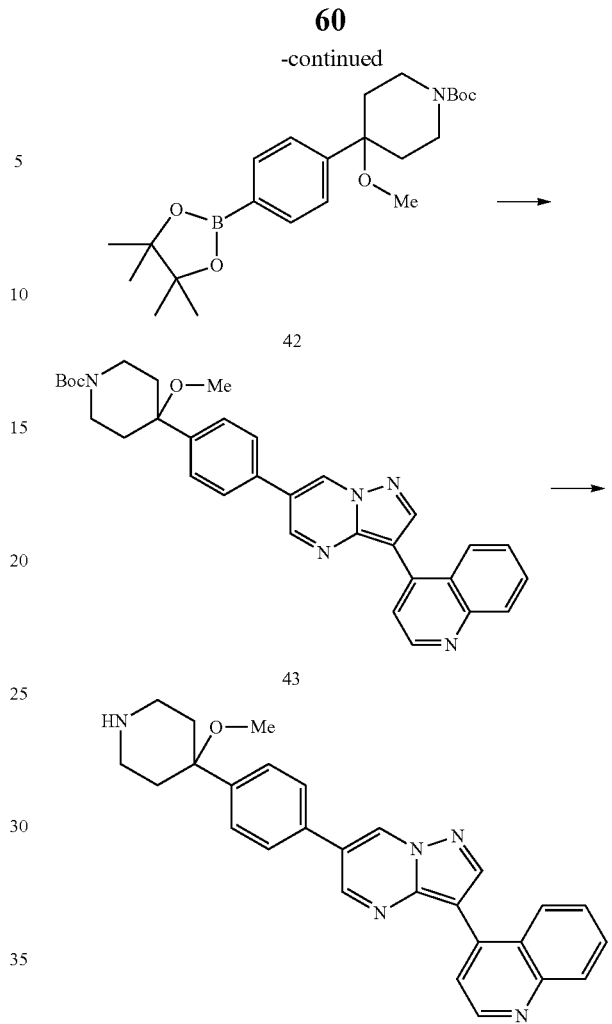

To a solution of 38 (500 mg) in CH$_2$Cl$_2$ (20 mL) was added (Boc)$_2$O (520 mg) and Et$_3$N (0.350 mLl). The reaction mixture was stirred at room temperature for 1.5 h. Additional 150 mg of (Boc)$_2$O and MeOH (2 mL) were added and the mixture was then stirred at rt for 3 h. The mixture was concentrated and the residue was purified by column chromatography to obtain 39. To a solution of 39 (500 mg, 1.4 mmol) in DMF (5 mL) was added NaH (60%, 112 mg, 2.8 mmol) at 0° C. The reaction mixture was stirred at rt for 15 min. MeI (0.174 mL, 2.8 mmol) was added and the mixture was then stirred at room temperature overnight. The mixture was quenched water, concentrated and then the residue was purified by column chromatography to obtain 40. A mixture of 40 (500 mg), 41 (0.300 mL), Pd(Ph$_3$P)$_4$ (30 mg), Et$_3$N (0.565 mL) in dioxane (5 mL) was degassed (3 times) and replaced under an atmosphere of nitrogen. The mixture was then heated at 160° C. for 10 min by microwave. The reaction mixture was then concentrated and purified with prep-HPLC to obtain 42 (260 mg). A mixture of 42 (260 mg), 4-(6-bromopyrazolo[1,5-a]pyrimidin-3-yl)quinoline (202 mg), Pd(Ph$_3$P)$_4$ (50 mg), K$_2$CO$_3$ (344 mg) in dioxane (3.2 mL), and H$_2$O (0.800 mL) was degassed (3 times) and placed under a nitrogen atmosphere. The mixture was heated at 150° C. for 8 min by microwave. The reaction mixture was then concentrated and purified with prep-HPLC to obtain 43 (55 mg). To 43 (50 mg) in MeOH/CH$_2$Cl$_2$ (1:1, 10 mL) was added HCl (4M in dioxane, 0.250 mL) at 0° C. and the mixture was stirred at room temperature overnight before being concentrated. Compound 44 was obtained as a yellow solid after washed the residue with MTBE/MeOH (10:1).

Example 7

Alternative synthesis of 4-[6-(4-Piperazin-1-ylphenyl)pyrazolo[1,5-a]pyridin-3-yl]-quinoline (37)

An alternative synthesis of 4-[6-(4-piperazin-1-ylphenyl)pyrazolo[1,5-a]pyridin-3-yl]-quinoline (37) is outlined in Scheme 7.

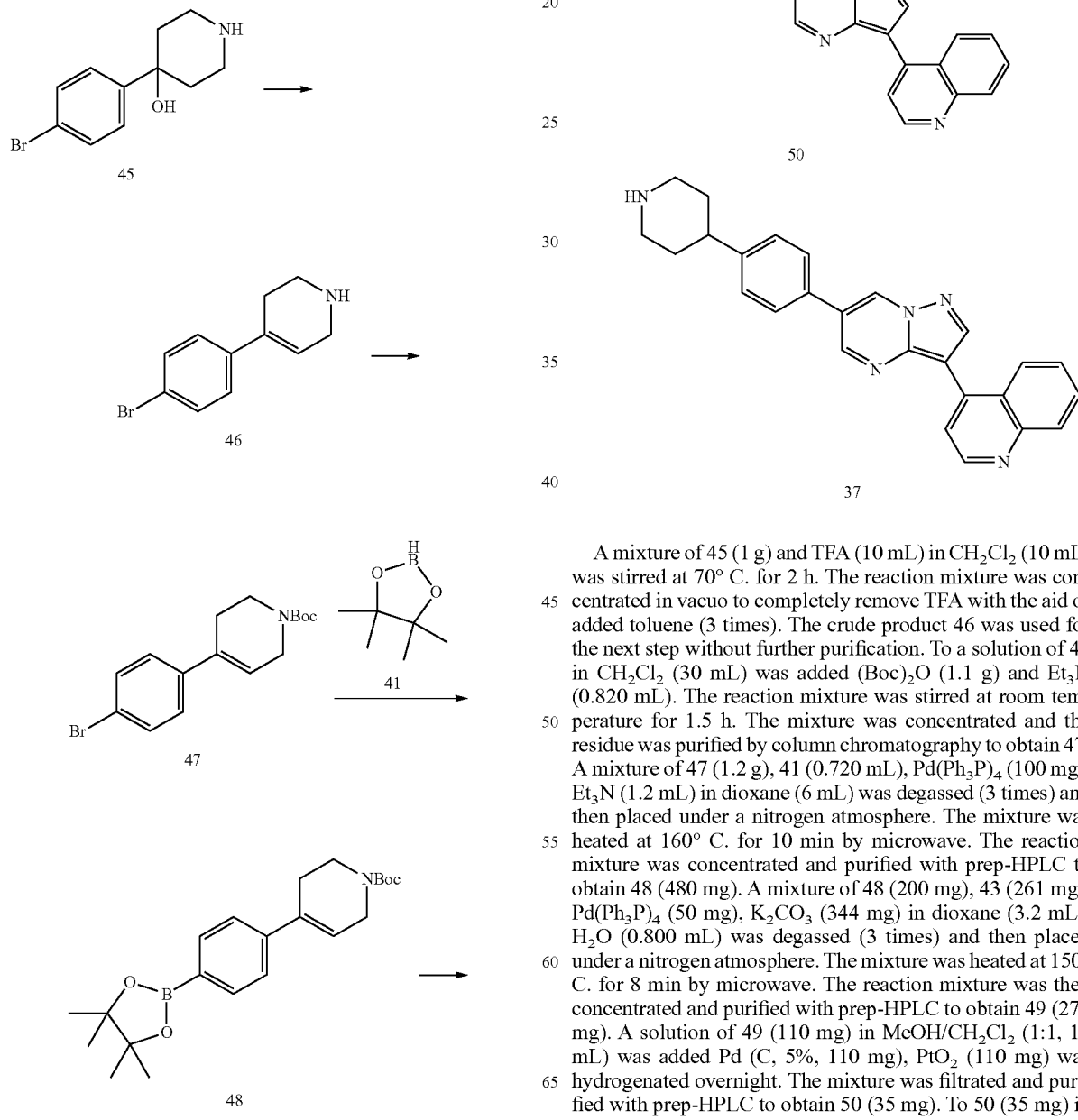

A mixture of 45 (1 g) and TFA (10 mL) in $CH_2Cl_2$ (10 mL) was stirred at 70° C. for 2 h. The reaction mixture was concentrated in vacuo to completely remove TFA with the aid of added toluene (3 times). The crude product 46 was used for the next step without further purification. To a solution of 46 in $CH_2Cl_2$ (30 mL) was added $(Boc)_2O$ (1.1 g) and $Et_3N$ (0.820 mL). The reaction mixture was stirred at room temperature for 1.5 h. The mixture was concentrated and the residue was purified by column chromatography to obtain 47. A mixture of 47 (1.2 g), 41 (0.720 mL), $Pd(Ph_3P)_4$ (100 mg), $Et_3N$ (1.2 mL) in dioxane (6 mL) was degassed (3 times) and then placed under a nitrogen atmosphere. The mixture was heated at 160° C. for 10 min by microwave. The reaction mixture was concentrated and purified with prep-HPLC to obtain 48 (480 mg). A mixture of 48 (200 mg), 43 (261 mg), $Pd(Ph_3P)_4$ (50 mg), $K_2CO_3$ (344 mg) in dioxane (3.2 mL), $H_2O$ (0.800 mL) was degassed (3 times) and then placed under a nitrogen atmosphere. The mixture was heated at 150° C. for 8 min by microwave. The reaction mixture was then concentrated and purified with prep-HPLC to obtain 49 (270 mg). A solution of 49 (110 mg) in $MeOH/CH_2Cl_2$ (1:1, 10 mL) was added Pd (C, 5%, 110 mg), $PtO_2$ (110 mg) was hydrogenated overnight. The mixture was filtrated and purified with prep-HPLC to obtain 50 (35 mg). To 50 (35 mg) in $MeOH/CH_2Cl_2$ (1:1, 5 mL) was added HCl (4 M in dioxane, 0.500 mL) at 0° C. and the mixture was stirred at room temperature overnight before concentrating. Compound 37 was obtained with prep-HPLC as a light yellow solid.

Example 8

Preparation of 4-(4-(3-(quinolin-4-yl)pyrazolo[1,5-a]pyrimidin-6-yl)phenyl)piperidin-4-ol (70)

The synthesis of 4-(4-(3-(quinolin-4-yl)pyrazolo[1,5-a]pyrimidin-6-yl)phenyl)piperidin-4-ol (70) is outlined in Scheme 8.

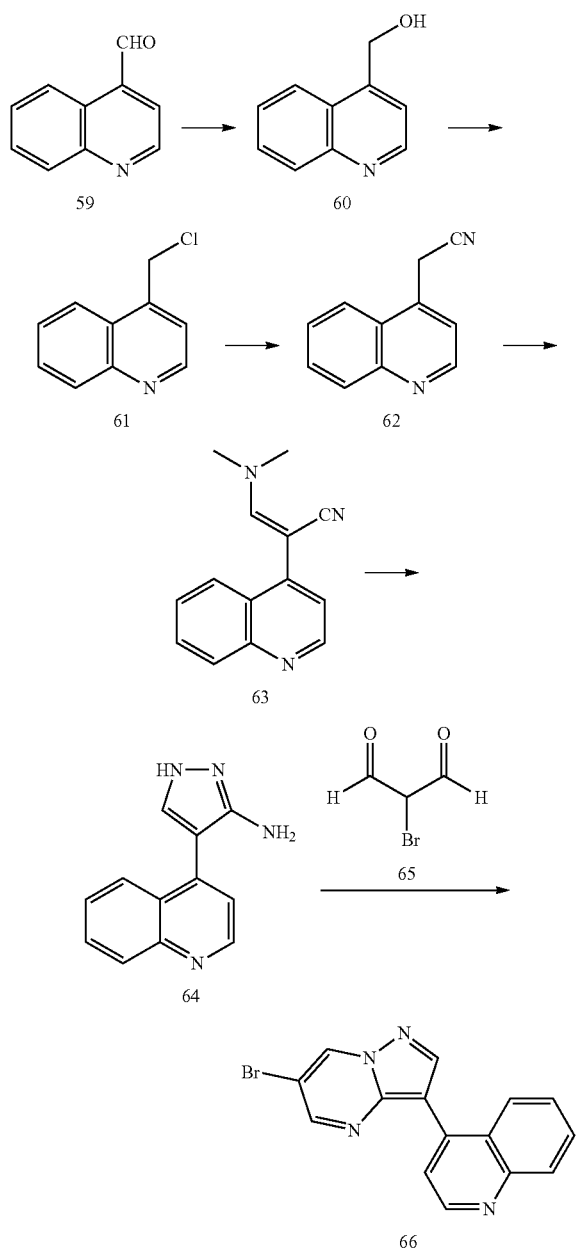

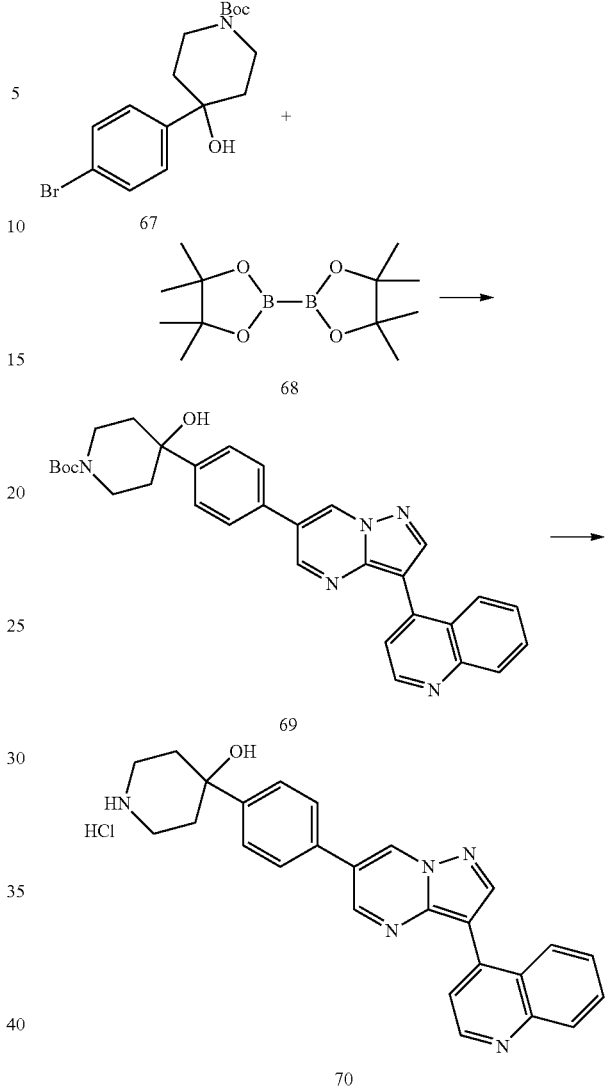

NaBH$_4$ (1.26 g, 33.4 mmol) was added to a solution of 59 (5.0 g, 31.8 mmol) in MeOH (60 ml) portion-wise at 0° C. over 20 min. The reaction mixture was stirred at room temperature for 1 h before being quenched with H$_2$O followed by extraction with ethyl acetate to give 60. SOCl$_2$ (4.2 mL, 57.2 mmol) was added drop-wise to a solution of 60 in CH$_2$Cl$_2$ (90 mL) at 0° C. over 20 min. The reaction mixture was then stirred at room temperature for 2 h before carefully quenched with saturated aqueous NaHCO$_3$ to bring the solution to a basic pH. The aqueous solution was extracted 3 times with CH$_2$Cl$_2$ and the combined organic layer was dried over Na$_2$SO$_4$. An off-white solid (61) was obtained after concentration. KCN (2.22 g, 34.1 mmol) was added to a solution of 61 in DMF (42 mL) at room temperature. The resulting mixture was stirred at 80° C. for 6 h. The solvent was evaporated in vacuo and the residue was dissolved in CH$_2$Cl$_2$ and washed with H$_2$O and brine, and dried over anhydrous Na$_2$SO$_4$. The material 62 (1.73 g, 32%) was obtained after column chromatography (Hex/EtOAc). A solution of 62 (800 mg, 4.76 mmol) in dimethylformamide-dimethyl acetal (5 mL) was heated at 120° C. for 6 h. The reaction mixture was then concentrated in vacuo to give dark-thick oil 63. To a solution 63 in EtOH (9 mL) and H$_2$O (1.2 mL) was added H$_2$NNH$_2$—

HBr (2 g, 17.7 mmol). The resulting mixture was heated at 110° C. for 5 h before concentrated to remove volatile solvent in vacuo. The residue was dissolved in EtOAc/EtOH (3:1, 20 mL) and then saturated aqueous $Na_2CO_3$ was added until the mixture was basic. The mixture was extracted with EtOAc/EtOH (3:1, 3×10 mL). The organic layer was dried over anhydrous $MgSO_4$, filtered and concentrated. The crude product was purified by chromatography to afford the S26 (850 mg, 85%) as an off-white solid. The mixture of 64 (800 mg, 3.81 mmol) and 65 (580 mg, 3.84 mmol) in EtOH (12 mL) and HOAc (250 mL) was heated at 50° C. for 5 h. The mixture was concentrated and purified on silica gel (Hex/EtOAc) to give 66 (480 mg, 38.7%) as off-white crystals. A flask charged with 67 (106 mg, 0.30 mmol), 68 (84 mg, 0.33 mmol), potassium acetate (88 mg, 0.9 mmol) and $PdCl_2$(dppf) (24 mg, 0.03 mmol) under a nitrogen atmosphere. DMF was added and the reaction was stirred at 80° C. for 4 h. After cooling the solution to room temperature, 66 (97 mg, 0.3 mmol), $PdCl_2$(dppf) (24 mg, 0.03 mmol) and 2 M $Na_2CO_3$ (1.0 mL) were added and the mixture was stirred at 80° C. under a nitrogen atmosphere overnight. The solution was allowed to cool to rt, the product was extracted with $CH_2Cl_2$ and washed with brine and dried over $MgSO_4$. Purification on silica gel using 5% MeOH in $CH_2Cl_2$ gave 69 (84 mg, 54%). HCl (4 M in dioxane, 500 µL) was added to 69 (42 mg, 0.08 mmol) in MeOH/$CH_7Cl_2$ (1:1, 14 mL) at 0° C. and the mixture was stirred at rt overnight before being concentrated and washed with $Et_2O$/MeOH (10:1) to give 70 (34 mg, 92%) as a yellow solid.

Example 9

Evaluation of BMP-Induced Phosphorylation of SMAD1/5/8

Evaluation of BMP4-induced phosphorylation of SMAD1/5/8 was performed using a sensitive cytoblot (cellular ELISA) technique in the presence of varying concentrations of compounds described herein. Murine pulmonary artery smooth muscle cells were isolated, explanted and cultured as previously described (see Takata et al. *Am. J. Physiol. Lung Cell Mol. Physiol.* 280:L272, 2001) and then grown to confluence in 96 well tissue culture plates. Cells were incubated in serum-free medium for 18 h, and then incubated with recombinant BMP2, BMP4, BMP6, BMP9, GDF5, TGF-β, or Activin A ligands (R&D Systems, Minneapolis, Minn.) at varying concentrations in duplicate for 20 minutes. Cells were fixed, and then blocked with 2% bovine serum albumin in phosphate buffered saline overnight. Cells were incubated with rabbit polyclonal anti-phospho-SMAD1/5/8 or anti-phospho-SMAD2 or anti-phospho-SMAD3 (1:1000, Cell Signaling Technologies), followed by HRP-conjugated anti-rabbit IgG, and then developed with ultra high sensitivity chemiluminescent substrate (BioFx, Maryland) and read on a Victor multilabel counter (Perkin Elmer).

A functional $IC_{50}$ was calculated for the inhibitory effects of various compounds on the phosphorylation of SMAD1/5/8. Specificity for BMP-mediated signaling was determined separately using a modification of the cellular ELISA technique assaying for the activation of SMAD2 or SMAD3 via TGF-β, or Activin A. A corresponding $IC_{50}$ was calculated for the effects of these compounds upon those signaling pathways. A comparison of dorsomorphin (DM) and compound 13 is shown in FIG. 1. Dorsomorphin exhibits a functional $IC_{50}$ of approximately 400 nM. compound 13 exhibits a functional $IC_{50}$ of approximately 5-10 nM. The approximate $IC_{50}$ for BMP-mediated SMAD1/5/8 activation for various compounds and derivatives is shown in Table 1.

TABLE 1

$IC_{50}$ determinations for inhibition of BMP-induced phosphorylation of SMAD1/5/8.

| $R^{40}$ | $R^{41}$ | $R^{42}$ | X | Y | $IC_{50}$ (µM) |
|---|---|---|---|---|---|
| 4-OMe—Ph | 4-Py | H | N | N | >1 |
| morpholine-ethoxy-phenyl | 4-Py | H | N | N | >1 |
| Et$_2$N-ethoxy-phenyl | 4-Py | H | N | N | <0.5 |
| 4-methylpiperazine-ethoxy-phenyl | 4-Py | H | N | N | <0.5 |

TABLE 1-continued
IC$_{50}$ determinations for inhibition of BMP-induced phosphorylation of SMAD1/5/8.
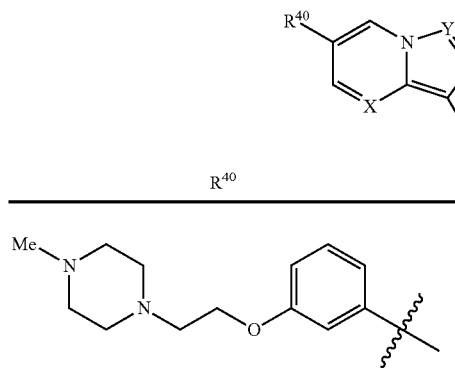
| R$^{40}$ | R$^{41}$ | R$^{42}$ | X | Y | IC$_{50}$ (μM) |
|---|---|---|---|---|---|
| 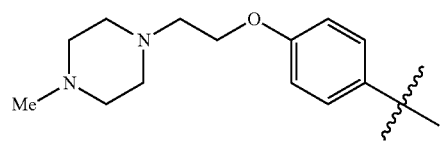 [SMILES: *c1ccc(OCCN2CCN(C)CC2)cc1] | 4-Py | H | N | N | >1 |
| 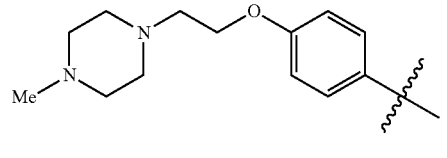 [SMILES: *c1ccc(OCCN2CCN(C)CC2)cc1] | 4-Py | Me | N | N | >10 |
| 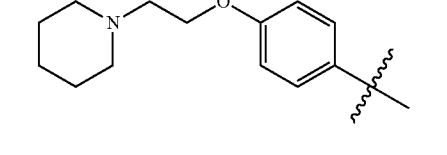 | 3-F-4-Py | H | N | N | >1 |
| 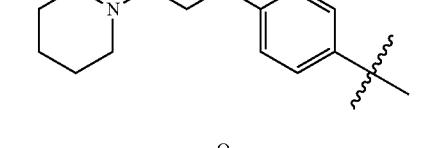 | 3-Py | H | N | N | >10 |
| 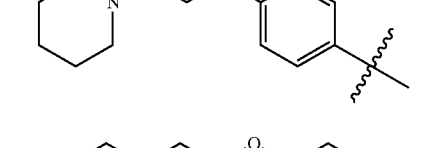 | H | H | N | N | >20 |
| 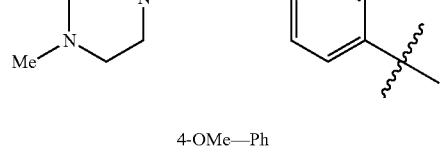 | Ph | H | N | N | >20 |
| 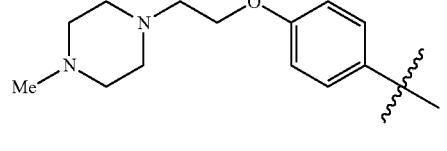 | 4-OMe—Ph | H | N | N | >20 |
| 4-OMe—Ph | 3-thienyl | H | N | N | >20 |
| 4-OMe—Ph | 6-quinolinyl | H | N | N | >20 |
| 4-OMe—Ph | 8-quinolinyl | H | N | N | >20 |
| 4-OMe—Ph | 5-quinolinyl | H | N | N | >1 |
| 4-OMe—Ph | 3-quinolinyl | H | N | N | >20 |
|  | 4-quinolinyl | H | N | N | <0.01 |

TABLE 1-continued

IC$_{50}$ determinations for inhibition of BMP-induced phosphorylation of SMAD1/5/8.

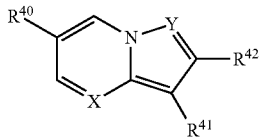

| R$^{40}$ | R$^{41}$ | R$^{42}$ | X | Y | IC$_{50}$ (μM) |
|---|---|---|---|---|---|
| 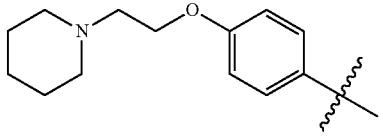 [SMILES: *c1ccc(OCCN2CCCCC2)cc1] | 4-quinolinyl | H | N | N | <0.1 |
| H | 4-quinolinyl | H | N | N | >1 |
| Ph | 4-quinolinyl | H | N | N | <1 |
| HO-4-Ph | 4-quinolinyl | H | N | N | <0.1 |
| 4-OMe—Ph | 4-quinolinyl | H | N | N | <0.1 |
| 4-OMe—Ph | 7-chloro-4-quinolinyl | H | N | N | <0.5 |
| 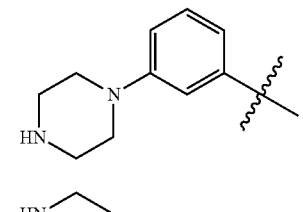 | 4-quinolinyl | H | N | N | >20 |
| 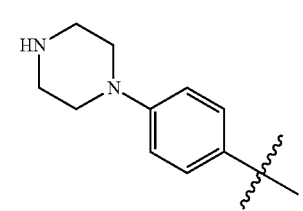 | 7-chloro-4-quinolinyl | H | N | N | <0.5 |
| 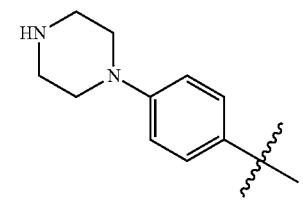 [SMILES: *c1ccc(N2CCNCC2)cc1] | 4-quinolinyl | H | N | N | <0.01 |
| 4-OMe—Ph | 4-quinolinyl | H | N | CCO$_2$Me | >20 |
| 4-OMe—Ph | 4-quinolinyl | H | N | CH | >20 |
| 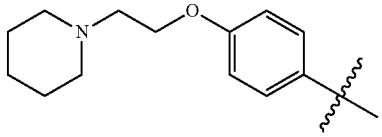 [SMILES: *c1ccc(OCCN2CCCCC2)cc1] | 4-quinolinyl | H | N | CH | >1.0 |
| 4-OMe—Ph | 4-quinolinyl | H | CH | N | <0.5 |
| 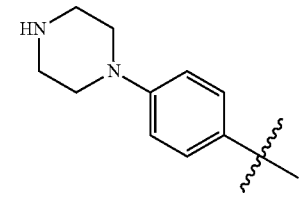 [SMILES: *c1ccc(N2CCNCC2)cc1] | 4-quinolinyl | H | CH | N | <0.01 |

Example 10

Figure 2:
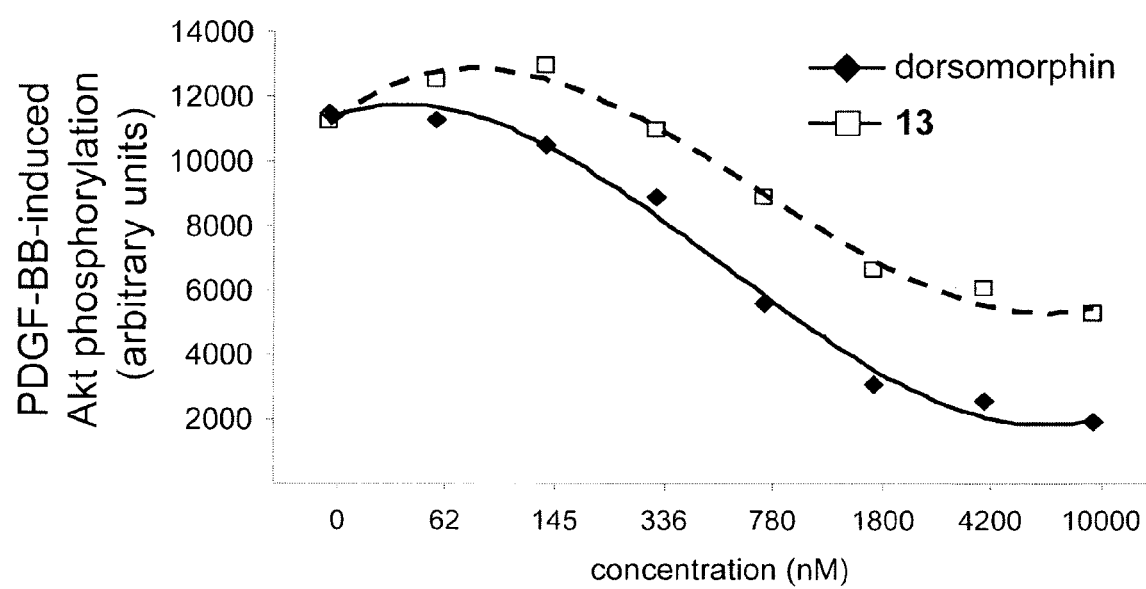
FIG. 2 shows a plot of BMP4-induced PDGF-BB-induced Akt phosphorylation measured by cellular ELISA comparing the effect of dorsomorphin and compound 13.

Evaluation of Selectivity for the Antagonism of BMP Receptor Versus Tyrosine Kinase Receptor Signaling Dorsomorphin is similar in structure to a number of compounds which are reported to inhibit tyrosine kinase recptors including KDR and PDGFR (Fraley et al. *Bioorg. & Med. Chem. Lett.* 12:2767, 2002). To test the relative effects of dorsomorphin and structurally-related compounds upon PDGFR-mediated signaling, PDGF-induced AKT phosphorylation was measured by cellular ELISA via the detection of phospho-AKT in PaSMCs treated with compounds for 10 min. followed by PDGF for 30 min. Dorsomorphin exhibits a functional $IC_{50}$ of approximately 500 nM, whereas compound 13 exhibits a functional $IC_{50}$ of approximately 2 µM (see FIG. 2). Thus, compound 13 improves upon the selectivity for BMP signaling versus PDGF signaling as compared to dorsomorphin. Similarly a five- to six-fold reduction in the antagonism of KDR-mediated signaling was found when comparing the activity of compound 13 versus dorsomorphin (not shown), consistent with increased selectivity for BMP signaling versus VEGF-mediated signaling.

Example 11

Evaluation of Hepatic Expression of Hepcidin

Figure 3:
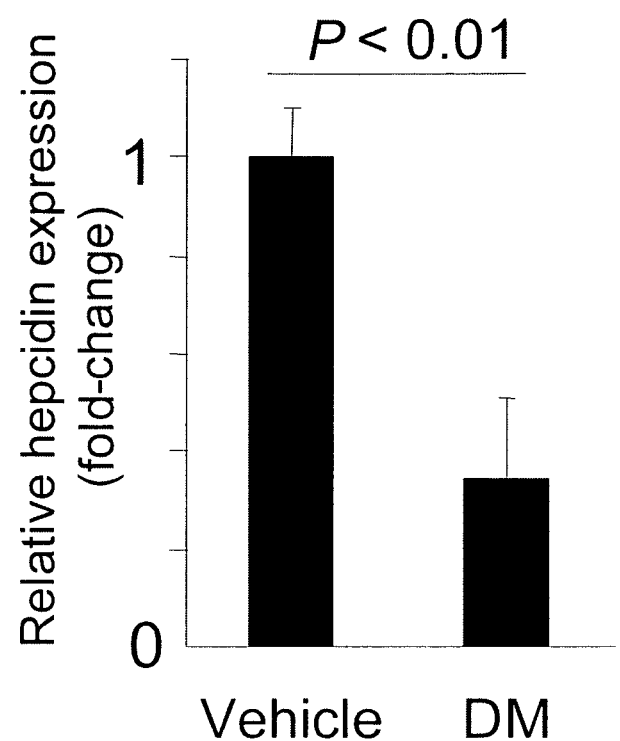
FIG. 3 shows the relative expression of hepcidin in C57BL/6 mice with and without dorsomorphin.
Figure 4:
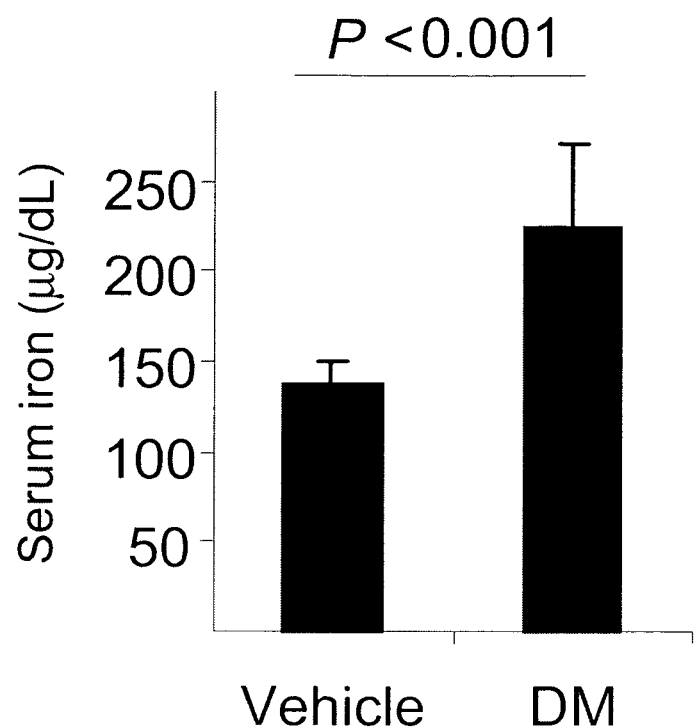
FIG. 4 shows levels of serum iron in C57BL/6 mice with and without dorsomorphin.

In C57BL/6 mice, 6 h after a single tail vein injection of dorsomorphin (10 mg/kg), liver hepcidin mRNA levels were measured by quantitative RT-PCR, and found to be one-third of those in controls (see FIG. 3; n=6 each group, P<0.01). In C57BL/6 mice, two IP injections of dorsomorphin (10 mg/kg) 12 h apart increased serum iron levels, measured by the Ferene S assay (ThermoFisher Scientific, Waltham, Mass.) measured 24 h after first injection by over 60%. (see FIG. 4; n=8 vehicle, n=7 dorsomorphin, P<0.001). Results are expressed as mean SD.

These results indicate that compounds of the invention may similarly decrease hepatic expression of hepcidin and increase levels of serum iron.

Example 12

Determination of Microsomal Stability in Pooled Mouse Liver Microsomes

Test compound (3 µM final concentration) along with 0.5 mg/mL microsome protein and 1 mM NADPH was incubated for 0, 5, 15, 30 and 60 min. Incubation of test compound and microsomes in the absence of NADPH served as a negative control. The samples were quenched with methanol and centrifuged for 20 min at 2500 rpm to precipitate proteins. Sample supernatants were analyzed (N=3) by LC/MS. The ln peak area ratio (compound peak area/internal standard peak area) was plotted against time and the slope of the line determined to give the elimination rate constant [k=(−1)(slope)]. The half life ($t_{1/2}$ in minutes) and the in vitro intrinsic clearance ($CL_{int}$ in µL/min/mg protein) values were calculated according to the following equations, where V=incubation volume in µL/mg protein:

$$t_{1/2} = \frac{0.693}{k}; \quad CL_{int} = \frac{V(0.693)}{t_{1/2}}.$$

Both dorsomorphin and the more potent compound 53 demonstrated low metabolic stability in mouse liver microsomes (dorsomorphin: half-life ($t_{1/2}$) of 10.4 min and intrinsic clearance ($CL_{int}$) of 133±6.6 µL/min/mg protein; 53: $t_{1/2}$ of 13.3 min and $CL_{int}$ of 104±3.4 µL/min/mg protein) (see Baranczewski et al. *Pharmacol. Rep.* 58:453, 2006). However, replacement of the ether on the pendent phenyl ring with piperazine resulted in a significant increase in mouse liver microsome stability. For example, 13 demonstrated a $t_{1/2}$ of 82 min and $CL_{int}$ of 16.9±5.6 µL/min/mg protein.

Example 13

Pharmacokinetic Analysis of Compound 13.HCl

Based on the potency and metabolic stability of 13.HCl, it was selected for in vivo pharmacokinetic analysis. The pharmacokinetics of 13.HCl was evaluated after a single bolus intraperitoneal administration (3 mg/kg) in male and female C57B16 mice on a commercial rodent diet and water ad libitum prior to the study. Compound plasma levels were determined by LC-MS/MS and the pharmacokinetic parameters were determined using WinNonlin software (Pharsight Co., Mountain View, Calif.). Dosing solutions (0.6 mg/mL) were prepared in a vehicle comprising 2% hydropropyl-β-cyclodextrin in phosphate-buffered saline (PBS). Each time point (pre-dose, 5, 10, 15, 30, 60, 120, 240, 480, 1440 min post-dose) was dosed as N=3/sex. Each blood sample was collected via cardiac puncture after euthanasia with $CO_2$ and placed in chilled tubes containing sodium heparin. Samples were centrifuged at 4° C. at 13,000 rpm for 5 min followed by extracted with acetonitrile and then analyzed.

The results of this study are shown in Table 2. The pharmacokinetics of 13 were similar in both male and female mice. The average maximal plasma concentrations were slightly higher in males (1.54 µM) than in females (1.29 µM) and were reached quickly (<5 min) following administration. The plasma half-life (1.6 h) and the average $AUC_\infty$ values (994 and 1030 ng·h/mL) were similar in male and female mice.

TABLE 2

Pharmacokinetic analysis of compound 13 in plasma following bolus intraperitoneal administration in mice (N = 3/sex).

| Sex | Dose mg/kg | $C_{max}$ µM | $t_{max}$ min | $t_{1/2}$ h | $AUC_\infty$ ng · h/mL |
|---|---|---|---|---|---|
| male | 3.0 | 1.54 | <5 | 1.6 | 994 |
| female | 3.0 | 1.29 | <5 | 1.6 | 1030 |

Example 14

Pharmacokinetic Analysis of Compounds 44.HCl and 37.HCl

The pharmacokinetics of 44.HCl and 37.HCl were evaluated after a single bolus intraperitoneal administration (3 mg/kg) in male C57B16 mice on a commercial rodent diet and water ad libitum prior to the study. Compound plasma levels were determined by LC-MS/MS and the pharmacokinetic parameters were determined using WinNonlin software (Pharsight Co., Mountain View, Calif.). Dosing solutions (0.6 mg/mL) were prepared in a vehicle comprising 2% hydropropyl-β-cyclodextrin in phosphate-buffered saline (PBS). Each time point (pre-dose, 5, 10, 15, 30, 60, 120, 240, 480, 1440 min post-dose) was dosed as N=3/sex. Each blood sample was collected via cardiac puncture after euthanasia with $CO_2$ and placed in chilled tubes containing sodium heparin. Samples were centrifuged at 4° C. at 13,000 rpm for 5 min followed by extracted with acetonitrile and then analyzed. The results of this study are shown in Table 3.

TABLE 3

Pharmacokinetic analysis of compounds 44•HCl and 37•HCl in plasma following bolus intraperitoneal administration in mice (N = 3).

| Compound | Dose mg/kg | $C_{max}$ μM | $t_{max}$ min | $t_{1/2}$ h | $AUC_\infty$ ng · h/mL |
|---|---|---|---|---|---|
| 44•HCl | 3.0 | 0.66 | <15 | 1.4 | 583 |
| 37•HCl | 3.0 | 0.29 | <15 | 2.2 | 207 |

Example 15

Pharmacokinetic Analysis after Oral Administration

The pharmacokinetics of compound 70 was evaluated after a single oral administration (3 mg/kg) in male C57B16 mice on a commercial rodent diet and water ad libitum prior to the study. Compound plasma levels were determined by LC-MS/MS and the pharmacokinetic parameters were determined using WinNonlin software (Pharsight Co., Mountain View, Calif.). Dosing solutions (0.6 mg/mL) were prepared in a vehicle comprising 2% hydropropyl-β-cyclodextrin in phosphate-buffered saline (PBS). Each time point (pre-dose, 15, 30, 60, 120, 240, 360, 480 and 1440 min post-dose) was dosed as N=3. Each blood sample was collected via cardiac puncture after euthanasia with $CO_2$ and placed in chilled tubes containing sodium heparin. Samples were centrifuged at 4° C. at 13,000 rpm for 5 min followed by extracted with acetonitrile and then analyzed. The results of this study are shown in Table 4.

TABLE 4

Pharmacokinetic analysis of compound 70 in plasma following oral administration in male mice (N = 3).

| Dose mg/kg | $C_{max}$ μM | $t_{max}$ min | $t_{1/2}$ h | $AUC_\infty$ ng · h/mL |
|---|---|---|---|---|
| 3.0 | 0.10 | 0.25 | 1.7 | 143 |

The pharmacokinetics of 13.HCl was evaluated after a single oral administration (3 mg/kg) in male C57B16 mice on a commercial rodent diet and water ad libitum prior to the study. Compound plasma levels were determined by LC-MS/MS and the pharmacokinetic parameters were determined using WinNonlin software (Pharsight Co., Mountain View, Calif.). Dosing solutions (0.6 mg/mL) were prepared in a vehicle comprising 2% hydropropyl-β-cyclodextrin in phosphate-buffered saline (PBS). Each time point (pre-dose, 15, 30, 60, 120, 240, 360, 480 and 1440 min post-dose) was dosed as N=3. Each blood sample was collected via cardiac puncture after euthanasia with $CO_2$ and placed in chilled tubes containing sodium heparin. Samples were centrifuged at 4° C. at 13,000 rpm for 5 min followed by extracted with acetonitrile and then analyzed. The results of this study are shown in Table 3.

TABLE 5

Pharmacokinetic analysis of compound 13•HCl in plasma following oral administration in male mice (N = 3).

| Dose mg/kg | $C_{max}$ μM | $t_{max}$ min | $t_{1/2}$ h | $AUC_\infty$ ng · h/mL |
|---|---|---|---|---|
| 3.0 | 0.69 | 60 | 1.1 | 919 |

Example 16

Evaluation of BMP Inhibitor Blockage of Hepcidin in a Zebrafish Model

Figure 5:
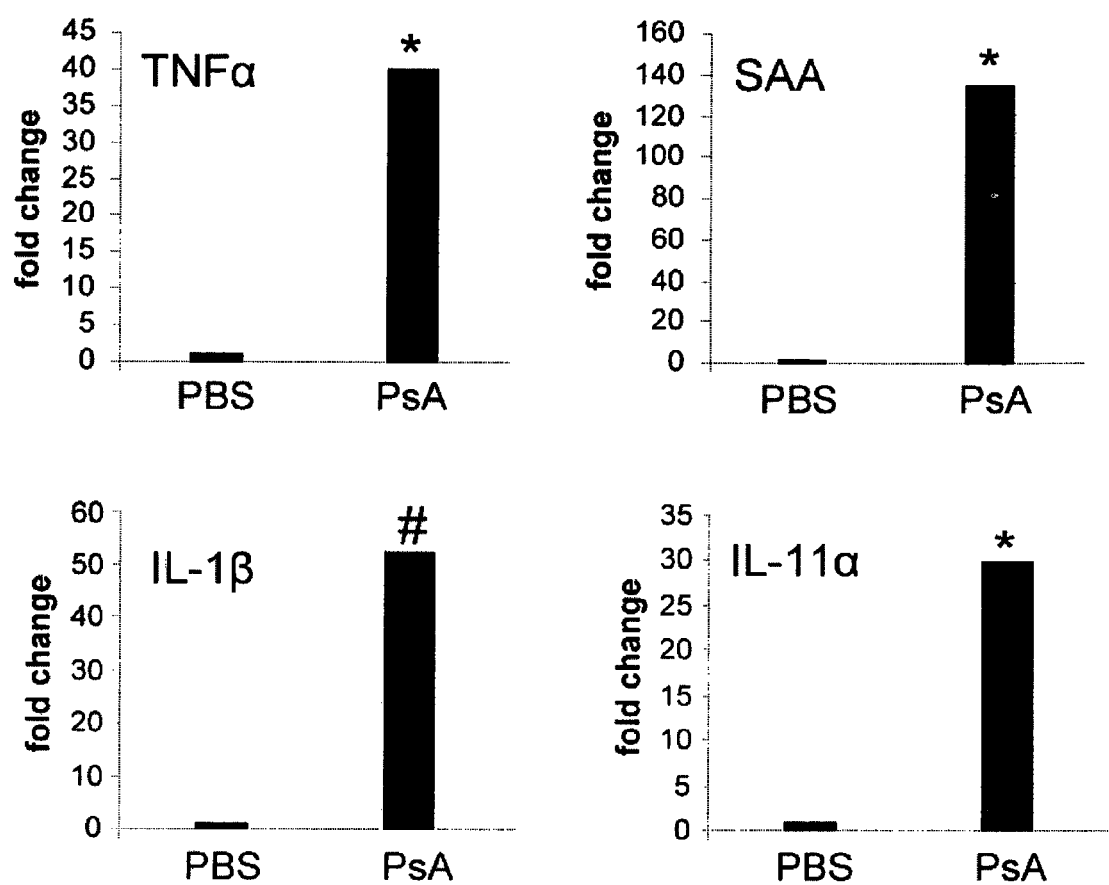
FIG. 5 shows results from RT-qPCR experiments in which zebrafish embryos were microinjected with 5000 live Pseudomonas aeruginosa (PSA) bacteria or PBS at 48 hpf and harvested 5 h later. TNFα, serum amyloid A (SAA), IL-1β, and IL-11α mRNA levels were measured.

The following describes the development an in vivo model of inflammation-induced hepcidin expression that is amenable to facile genetic and pharmacological manipulation. The zebrafish is an attractive organism because it enables rapid knockdown of gene function via morpholino oligonucleotides and because it is highly amenable to pharmacological manipulation. Live *Pseudomonas aeruginosa* (PsA) were microinjected into the yolk of three-day-old zebrafish to induce a rapid and robust inflammatory response. It was determined that injection of bacteria induces robust expression of inflammatory markers. Embryos were injected with 5000 live PsA bacteria or phosphate PBS at 48 hpf and harvested 5 h later. TNFα, serum amyloid A (SAA), IL-1β, and IL-11α mRNA levels were measured by RT-qPCR (FIG. 5; *P<0.001 vs PBS, #P<0.002 vs. PBS). These results demonstrate that PsA markedly increased expression of inflammatory markers in zebrafish embryos.

Figure 6:
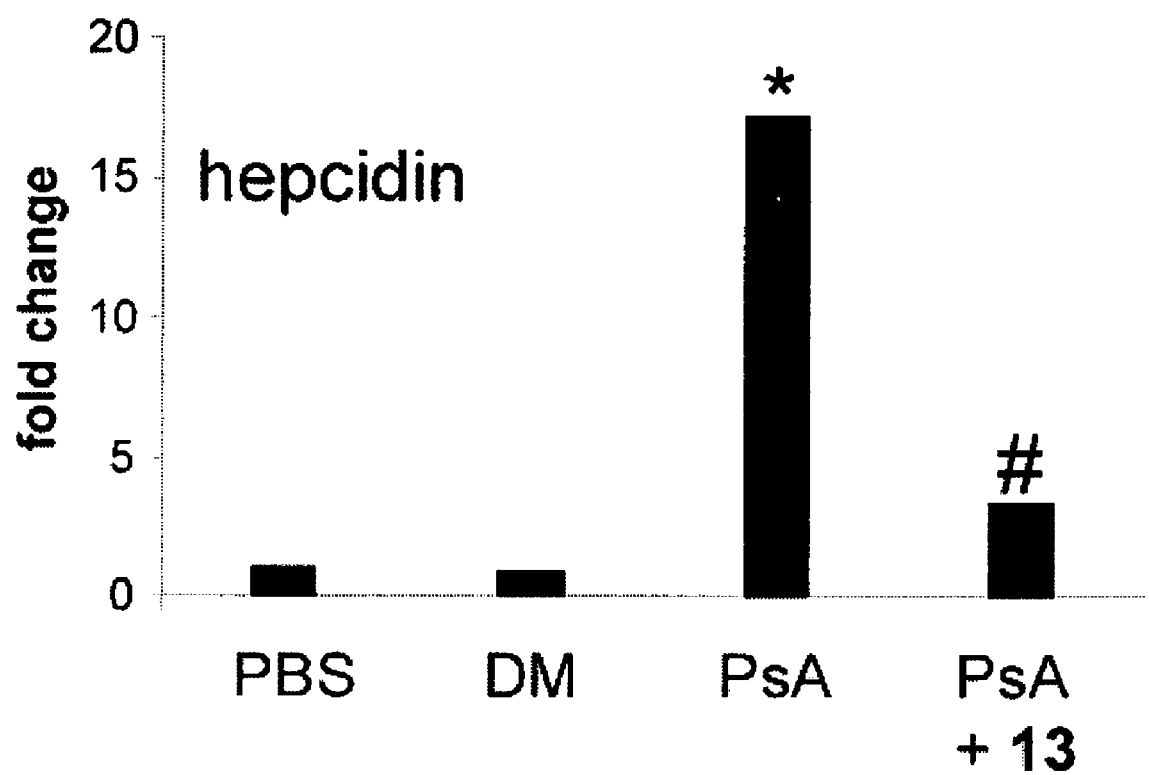
FIG. 6 shows results from RT-qPCR experiments in which zebrafish embryos were injected with PsA or PBS in the presence or absence of 6 μM compound 13, and hepcidin mRNA levels were measured 5 h later.

Next, it was examined whether the inflammatory response evoked by PsA in zebrafish is accompanied by induction of hepcidin. Embryos were injected with PsA or PBS in the presence or absence of 6 μM compound 13 and hepcidin mRNA levels were measured 5 h later by RT-qPCR. PsA injection induced a >15-fold induction of hepcidin within 5 h (FIG. 6; *P<0.0005 vs PBS, #P<0.01 vs PsA). This induction of hepcidin was almost completely blocked by treating the injected zebrafish with compound 13. These data indicate that the inflammation-induced hepcidin expression observed in mice and humans is conserved in zebrafish and that this activity is dependent upon BMP signaling.

Example 17

Compound 13 Inhibits IL6-Induced Hepcidin Expression in HepG2 Hepatoma Cells

Figure 7:
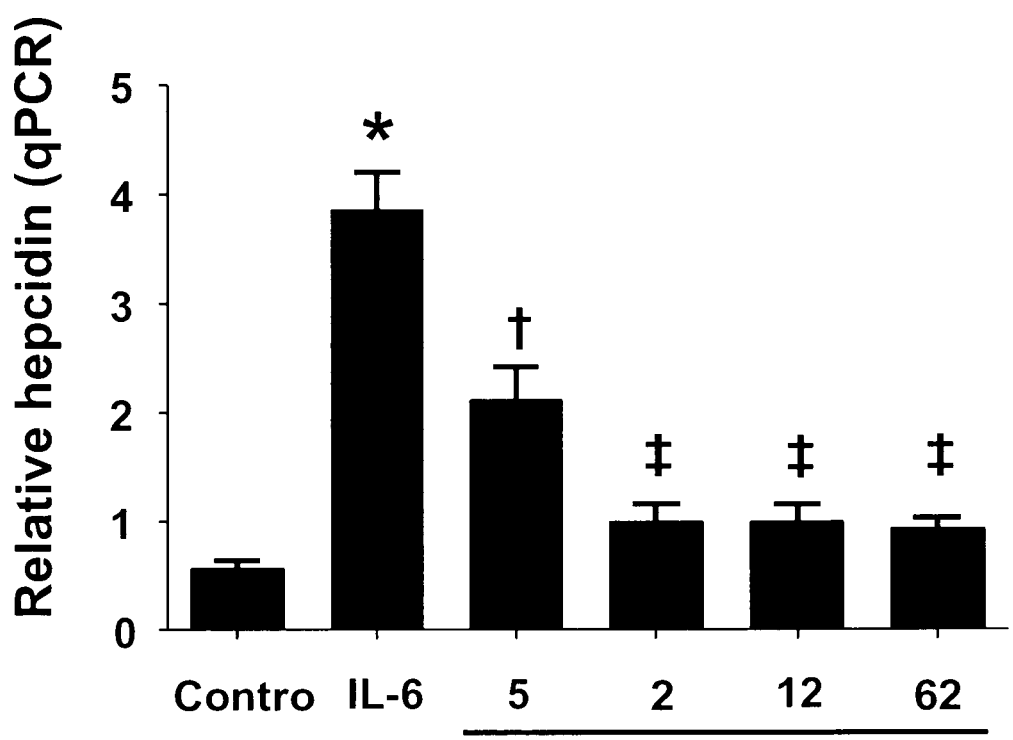
FIG. 7 shows the results of relative RNA level measurements from human HepG2 cells pretreated with compound 13 or vehicle for 30 minutes that were then incubated without and with IL6.

It was previously shown that incubation of Hep3B cells with interleukin 6 (IL6) for 6 h increased hepcidin mRNA levels (~2-fold) and that induction of hepcidin expression could be inhibited by dorsomorphin. It is now shown that incubation of human HepG2 cells with IL6 for 1.5 h increased hepcidin mRNA levels ~7-8-fold. HepG2 cells pretreated with compound 13 (5-625 nM) or vehicle for 30 min. were incubated with IL6 (50 ng/mL) for 1.5 h. Cells were harvested, and hepcidin mRNA and 18S rRNA levels were measured by quantitative RT-PCR. Changes in gene expression were normalized to 18S ribosomal RNA levels using the relative cycle threshold method. Relative hepcidin mRNA levels are presented as fold-change compared with levels in vehicle-treated cells (FIG. 7, N=4 per condition; *P<0.00001 vs. control; †P<0.01 vs. IL-6; ‡P<0.001 vs. IL-6). Incubation with compound 13 abrogated the IL6-mediated increase in hepcidin mRNA levels in a dose-dependent fashion. Pretreatment with cycloheximide, an inhibitor of protein synthesis, did not block the ability of IL6 to induce hepcidin gene expression (data not shown). These results demonstrate that our current lead BMP type I receptor inhibitor, compound 13, can prevent the induction of hepcidin by IL6.

Example 18

Compound 13 Prevents Turpentine-Induced Hypoferrinemia and Microcytic Anemia in Ice To model the anemia of inflammation, C57BL/6 mice were studied in which chronic inflammation was induced by weekly subcutaneous injections of turpentine.

Figure 8:
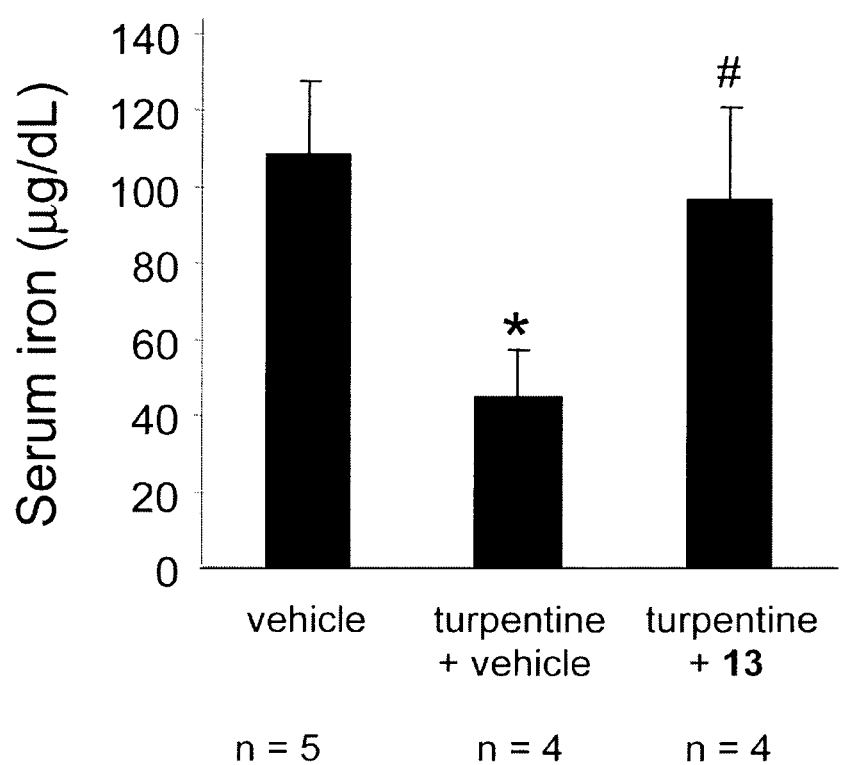
FIG. 8 shows a histogram of serum iron levels of mice which received a subcutaneous injection of turpentine with and without compound 13.
Figure 9:
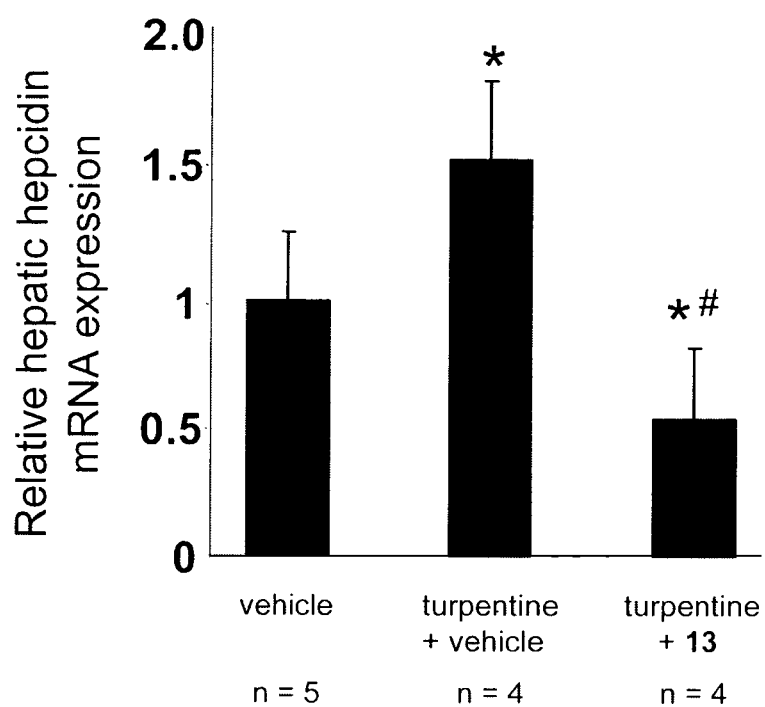
FIG. 9 shows a histogram of relative hepatic hepcidin gene expression in mice which received a subcutaneous injection of turpentine with and without compound 13.

Mice received a subcutaneous injection of turpentine, and 24 h later, serum was obtained for measurement of iron concentrations. Compound 13 (3 mg/kg) or vehicle was administered ip concurrently with turpentine and 12 hours later. Vehicle treated mice without turpentine injection were studied as controls. N=4-5 mice per group. It was found that 24 h after turpentine injection, serum iron levels dropped to <40% of basal iron levels. Administration of compound 13 prevented turpentine-induced reduction in serum iron levels (FIG. 8; *P<0.01 vs vehicle alone. #P<0.01 vs turpentine with vehicle). Twenty-four hours after turpentine injection, hepatic hepcidin mRNA levels increased ~50% (*P<0.01 vs. vehicle). Treatment of animals with two doses of LDN-193189 (3 mg/kg IP every 12 hours) beginning concurrently with turpentine challenge prevented elevation of hepatic hepcidin mRNA levels, (#P<0.05 vs. turpentine, FIG. 9).

Figure 10:
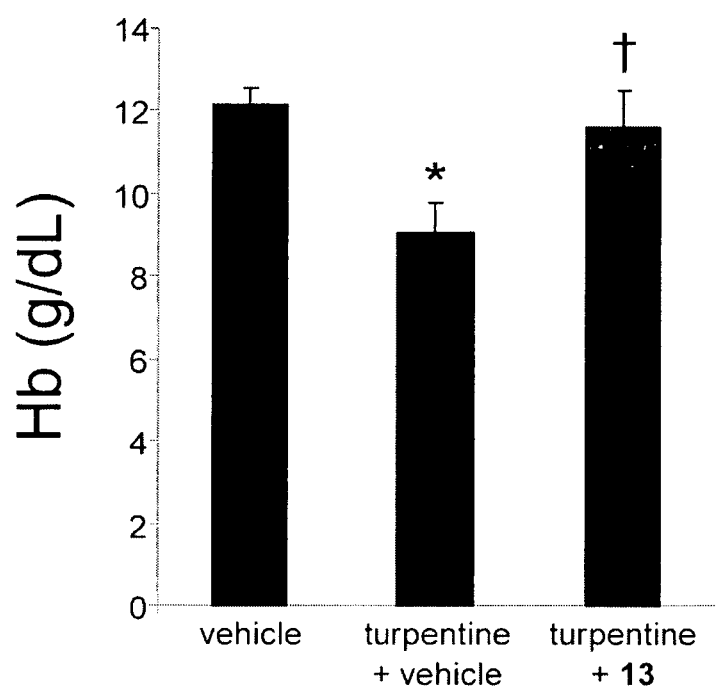
FIG. 10 shows a histogram of hemoglobin (Hb) levels from the blood of mice that received a subcutaneous injection of turpentine weekly for 3 weeks, with and without compound 13.
Figure 11:
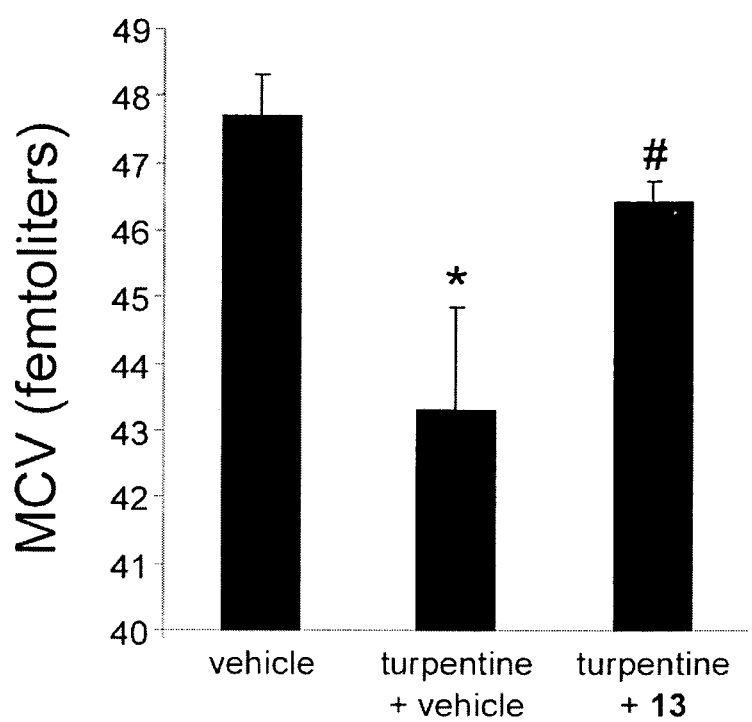
FIG. 11 shows a histogram of MCV levels from the blood of mice that received a subcutaneous injection of turpentine weekly for 3 weeks, with and without compound 13.
Figure 12:
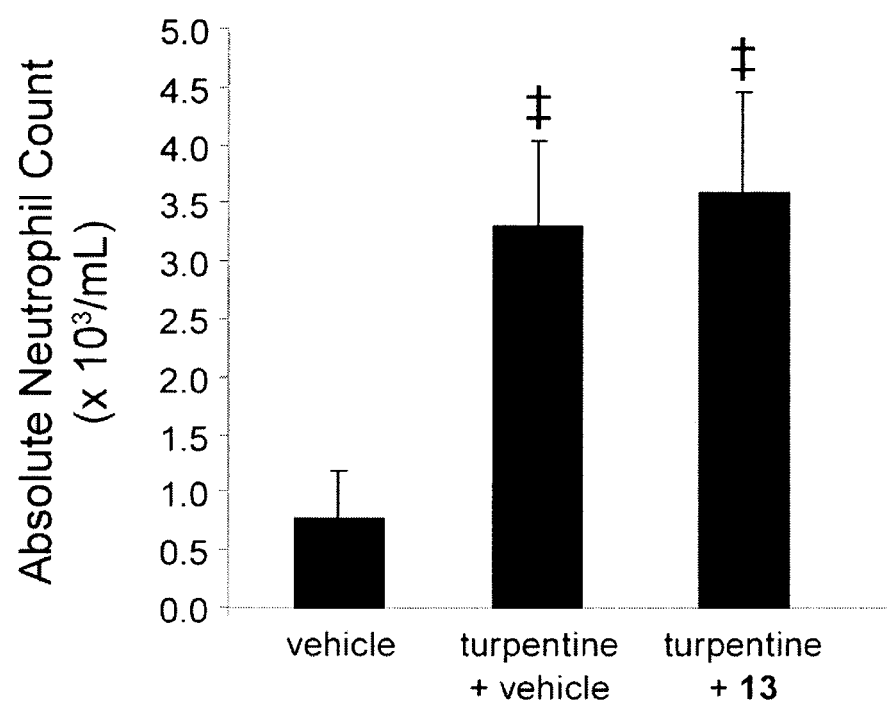
FIG. 12 shows a histogram of absolute neutrophil counts from the blood of mice that received a subcutaneous injection of turpentine weekly for 3 weeks, with and without compound 13.

Mice received a subcutaneous injection of 100 µL turpentine weekly for 3 weeks. Compound 13 or vehicle (3 mg/kg) was administered ip beginning with the first turpentine injection and every 12 h thereafter. Vehicle treated mice without turpentine injection were studied as controls. One week after the final turpentine dose, blood was drawn for Hb levels, mean corpuscular volume (MCV), and absolute neutrophil counts. Hemoglobin (Hb) levels (FIG. 10) and mean corpuscular volume (MCV; FIG. 11) decreased, and absolute neutrophil counts (FIG. 12) increased in turpentine-challenged and vehicle-treated mice, while administration of compound 13 prevented the decline in Hb levels and MCV but did not affect the increase in absolute neutrophil counts (N=3-5 mice per group. *P<0.01 vs. vehicle; †P<0.01 vs. turpentine with vehicle; #P<0.05 vs. turpentine ‡P<0.05 vs. vehicle). Of note, administration of compound 13 (every 12 h for 3 weeks) did not induce weight loss or other evident toxicity in mice. These observations confirm that subcutaneous administration of turpentine induces a microcytic anemia in mice. Moreover, these findings represent the first demonstration that inhibition of BMP signaling can prevent anemia in an animal model of anemia of inflammation.

Example 19

Figure 13:
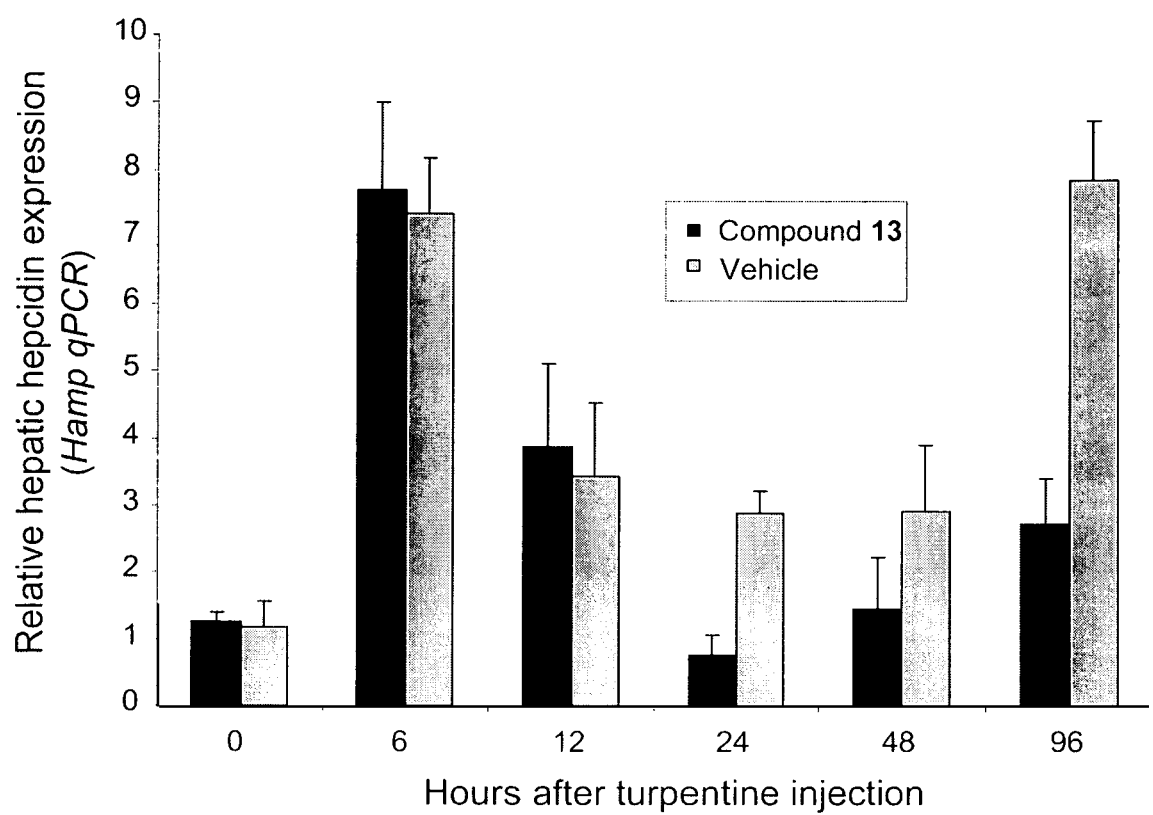
FIG. 13 shows relative levels of hepatic hepcidin gene expression in turpentine-challenged mice treated with vehicle or compound 13.

Compound 13 Suppresses Turpentine-Induced Hepatic Hepcidin Expression at 24 h-96 h Injection of 100 µL of turpentine intrascapularly into 10-week-old male wild-type C57BL/6 mice induced an early rise in hepatic hepcidin levels at 6 h of 7-8-fold over baseline levels, which plateaued at 12-48 hours at approximately 3-fold over basal levels. A subsequent rise in hepatic hepcidin levels was observed at 96 hours. Ongoing treatment with compound 13 (3 mg/kg IP every 12 h) following turpentine challenge effectively suppressed hepcidin elevation at 24-96 hours as compared to vehicle treatment (FIG. 13; n=5 mice for each treatment and time).

Example 20

Treatment of Wild-Type Mice with Compound 13 does not Impact Circulating Numbers of Erythrocyte, Myeloid, Lymphocyte or Thrombocyte Lineages Treatment of 10-week-old male C57BL/6 wild-type mice with compound 13 (3 mg/kg/d IP) for 30 days did not appear to cause myelosuppression, thrombocytopenia, anemia or conversely erythrocytosis (see Table 6). In addition, this treatment did not cause an elevation of serum iron compared to vehicle-treated controls in the steady state after 30 days treatment (data not shown).

TABLE 6

Treatment of wild-type mice with compound 13 does not impact circulating numbers of erythrocyte, myeloid, lymphocyte or thrombocyte lineages.

| Assay | Compound 13 average (n = 4) | SEM | Vehicle average (n = 5) | SEM |
|---|---|---|---|---|
| Total WBC | 1.9 | 0.3 | 2.3 | 0.2 |
| % Neutrophil | 30.8 | 5.4 | 24.0 | 3.1 |
| % Lymphocyte | 63.1 | 7.6 | 69.7 | 4.4 |
| % Monocyte | 3.8 | 0.7 | 4.2 | 0.9 |
| RBC | 9.0 | 0.2 | 8.5 | 0.1 |
| Hb | 11.9 | 0.1 | 12.5 | 0.2 |
| Hct | 43.8 | 0.9 | 42.3 | 0.3 |
| MCV | 48.5 | 1.0 | 50.1 | 0.7 |
| MCHC | 27.3 | 0.3 | 29.6 | 0.3 |
| RDW | 18.6 | 0.0 | 17.7 | 0.2 |
| Platelet count | 830.5 | 73.2 | 628.4 | 86.6 |
| % Reticulocyte | 2.6 | 0.6 | 2.9 | 0.1 |

Units are as follows:
WBC × $10^9$/L;
RBC × $10^{12}$/L;
Hb g/dL;
Hct %;
MCV fl;
MCHC g/dL;
RDW %;
Platelet count × $10^9$/L;
Reticulocyte %.

Example 21

Effect of Compound 13 on Ectopic Calcification

Fibrodysplasia ossificans progressiva (FOP) is caused by the presence of a constitutively-active mutant form of ALK2 in affected individuals (Shore et al. *Nat. Genet.* 38:525-527 (2006)). A specific inhibitor of BMP signaling can be used to prevent excessive bone formation in response to trauma, musculoskeletal stress or inflammation. The BMP inhibitor could also be used to aid in regression of pathologic bone. The BMP inhibitor could be administered systemically or locally to concentrate or limit effects to areas of trauma or inflammation.

Figure 14:
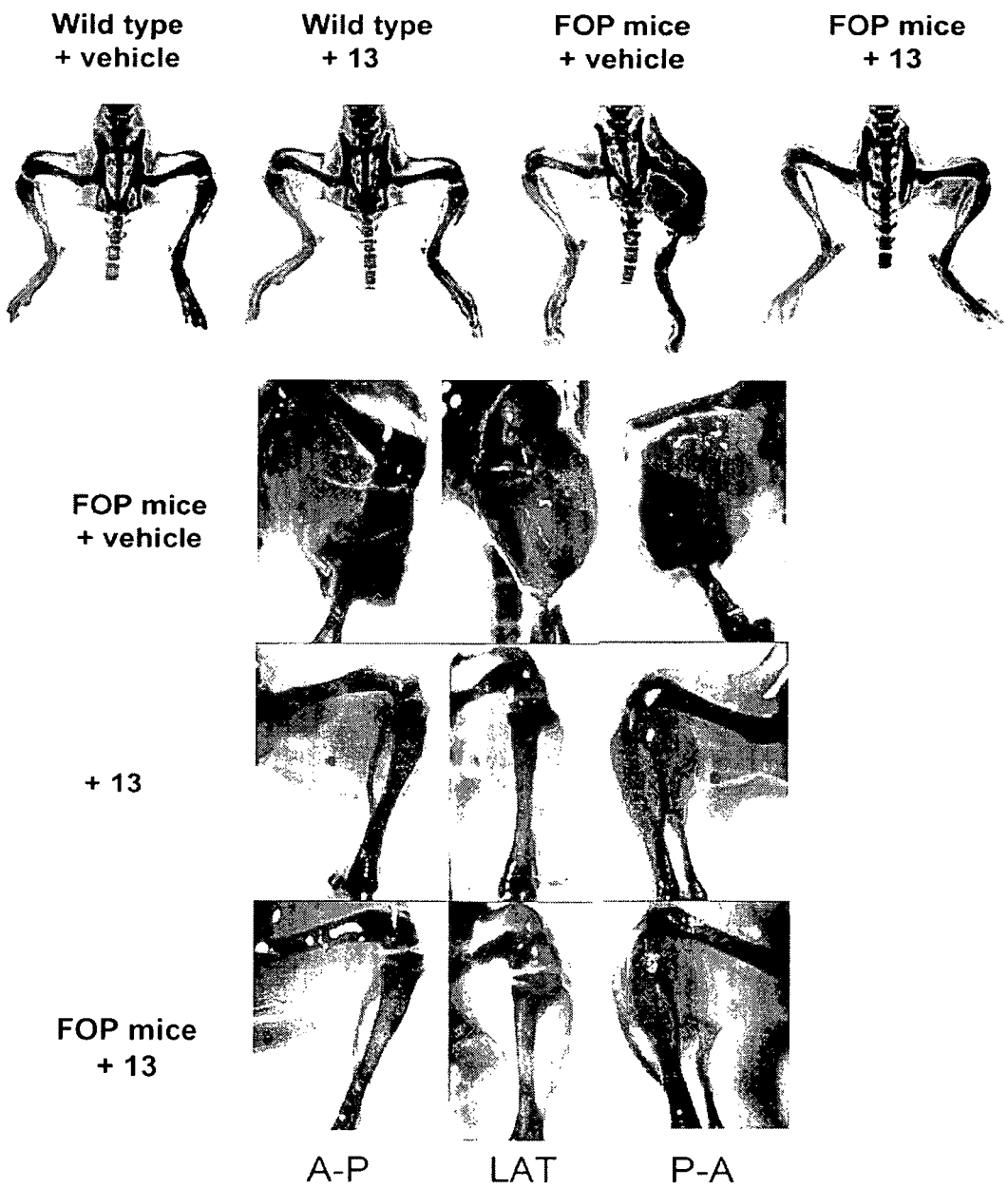
FIG. 14 shows images of fibrodysplasia ossificans progressiva (FOP) mutant mice treated with and without compound 13 to demonstrate the effect of compound 13 upon ectopic calcification. A-P, anterior-posterior; LAT, lateral; P-A, posterior-anterior views of left hindlimb.

A mouse model of FOP was developed in which expression of a constitutively-active mutant form of ALK2 was induced by injecting the popliteal fossa of a genetically-modified mouse with an adenovirus directing expression of Cre recombinase. This model reproduces the ectopic calcification and disability seen in FOP patients. FOP mutant mice treated with adenovirus develop ectopic calcifications within 15 days of treatment. Twice daily administration of compound 13 (3 mg/kg ip) prevented the ectopic calcification and disability (FIG. 14). Mice were fixed and stained with Alizarin Red and Alcian Blue, revealing ectopic calcifications (stained) in the gastrosoleus muscles of the affected limbs of FOP mice only. Wild type mice treated with compound 13 (3 mg/kg BID) or vehicle exhibited normal skeletal development. Treatment of FOP mutant mice with compound 13 but not vehicle inhibited the development of ectopic calcifications.

All publications and patents cited herein are hereby incorporated by reference in their entirety.

Those skilled in the art will recognize, or be able to ascertain using no more than routine experimentation, many equivalents to the specific embodiments of the invention described herein. Such equivalents are intended to be encompassed by the following claims.

Example 22

Figure 15:
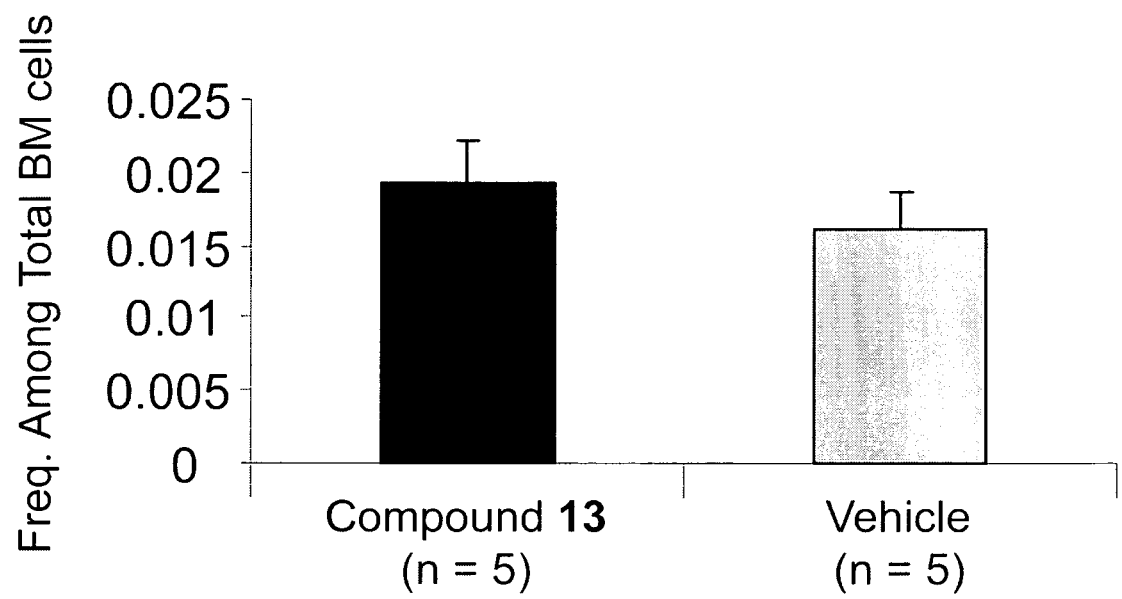
FIG. 15 shows a histogram of the frequency of hematapoietic stem cells in the bone marrow as a result of treatment with or without compound 13.

Treatment with Compound 13 does not Significantly Alter Frequency of Hematopoietic Stem Cells in the Bone Marrow Ten-week-old male C57BL/6 mice were treated chronically with compound 13 (3 mg/kg/d IP) for 30 days, and bone marrow harvested and subjected to multicolor flow cytometry to quantify hematopoietic stem cell lineages based on cell surface marker expression. No significant difference was detected in the frequency of hematopoietic stem cells in the marrow of compound 13-treated mice versus vehicle-injected controls (FIG. 15).

Example 23

Figure 16:
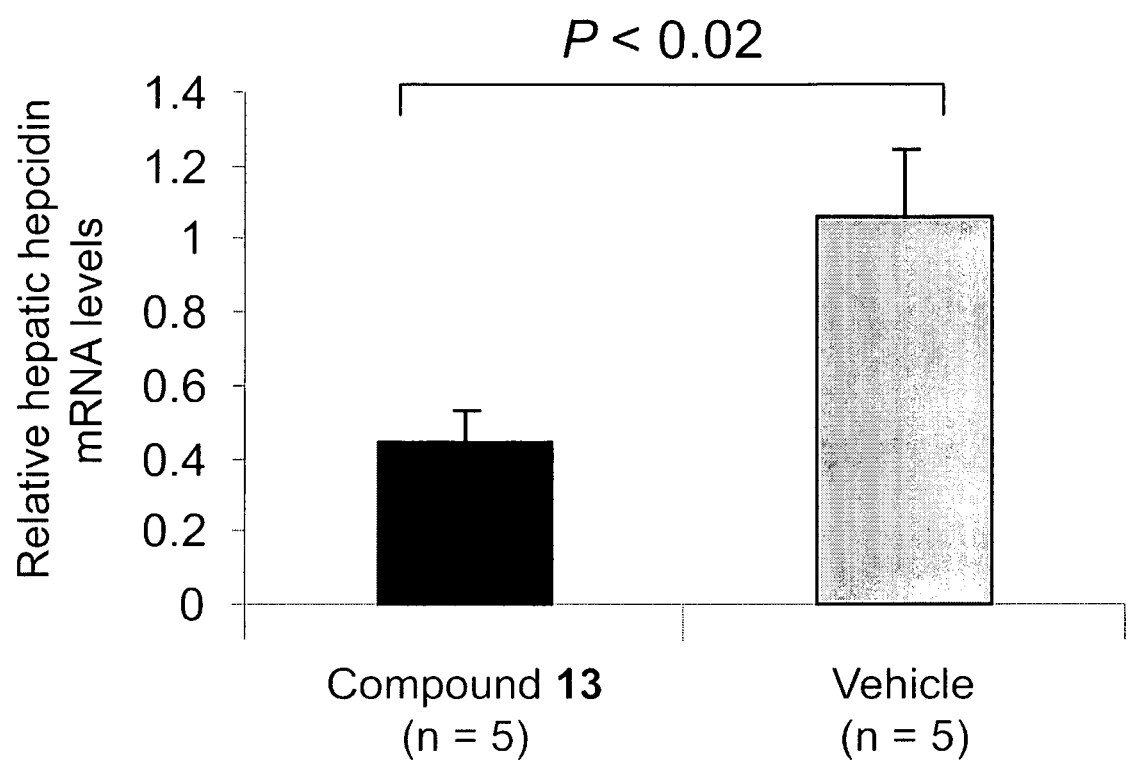
FIG. 16 shows the relative expression of hepcidin in C57BL/6 mice with and without compound 13.

Treatment with Compound 13 Reduces Hepatic Hepcidin Expression in the Steady State Ten-week-old male C57BL/6 mice fed a normal iron replete diet were treated chronically with compound 13 (3 mg/kg/d IP) or vehicle for 30 days, and hepatic hepcidin mRNA levels were measured by quantitative RT-PCR. A significant reduction in basal hepcidin levels to levels 40% of those found in vehicle-treated mice was observed in response to drug treatment (FIG. 16).

Example 24

Turpentine-Induced Model for Anemia of Inflammation

Wild-type 10-week-old male C57BL/6 mice were injected with 100 μL of turpentine subscapularly each week for 3 weeks to induce anemia. After the establishment of anemia, treatment with either vehicle or compound 13 (3 mg/kg/d IP) is begun concurrently with an additional 3 weeks of weekly turpentine injections, to assess the potential for rescuing established turpentine-induced anemia of inflammation.

Compound 13 Improves Established Turpentine-Induced Anemia

Figure 17:
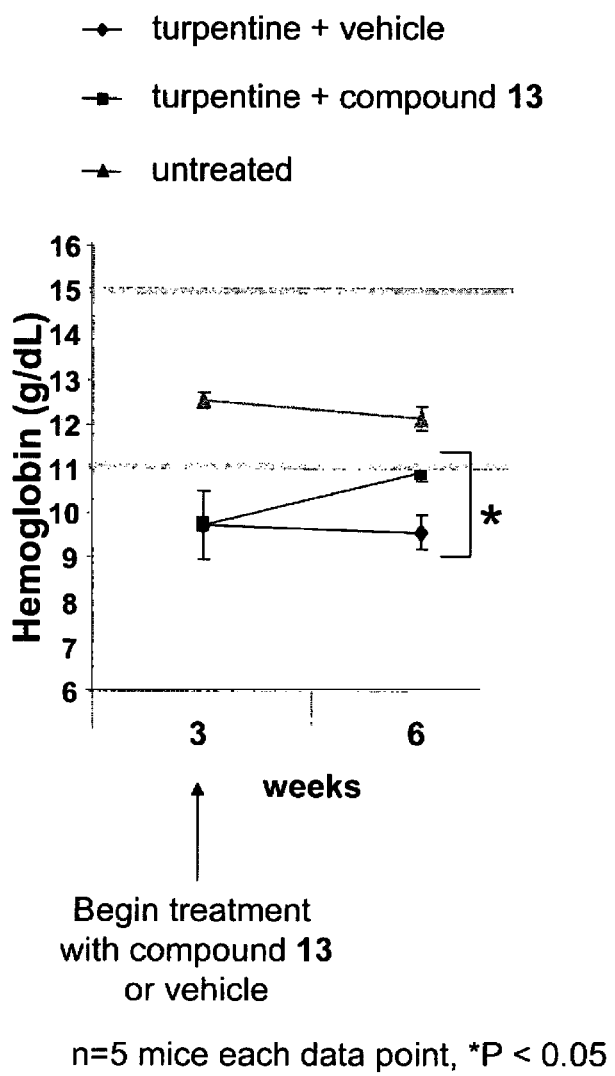
FIG. 17 shows a histogram indicating blood hemoglobin levels in mice that were untreated, treated with turpentine and vehicle, or treated with turpentine and compound 13.
Figure 18:
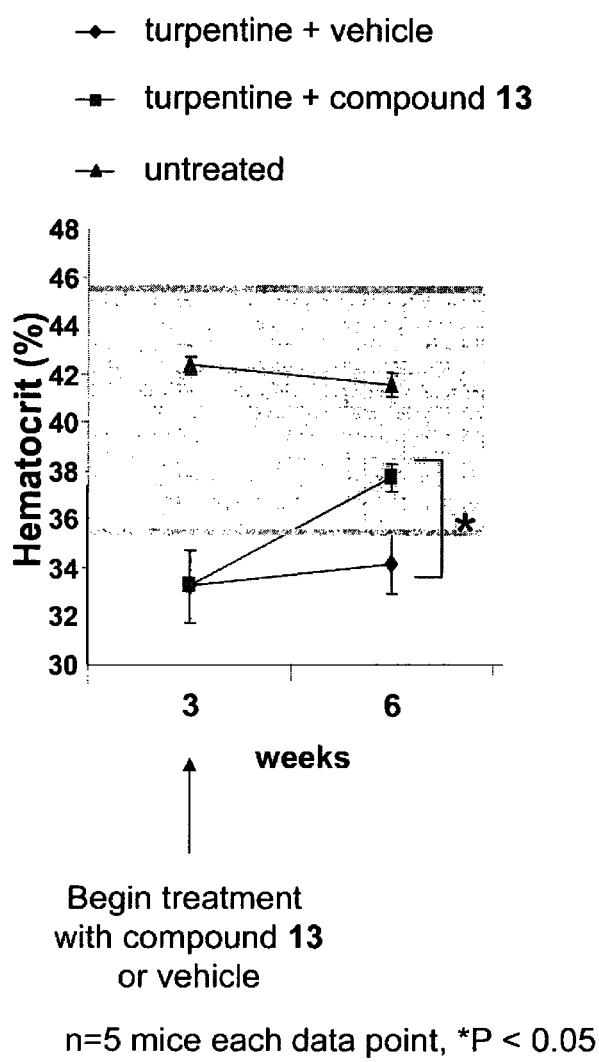
FIG. 18 shows a histogram indicating blood hematocrit levels in mice that were untreated, treated with turpentine and vehicle, or treated with turpentine and compound 13.

Turpentine-treated animals were found to have anemia after 3 weeks of turpentine injections (shaded areas indicate normative values in C57BL/6 mice for each parameter). After beginning compound 13 treatment (3 mg/kg/d IP) for the subsequent 3 weeks, a significant improvement in anemia measured by blood hemoglobin or hematocrit was observed (FIG. 17), compared to vehicle-injected controls, with restoration of hematocrit to values within the normal range (FIG. 18).

Figure 19:
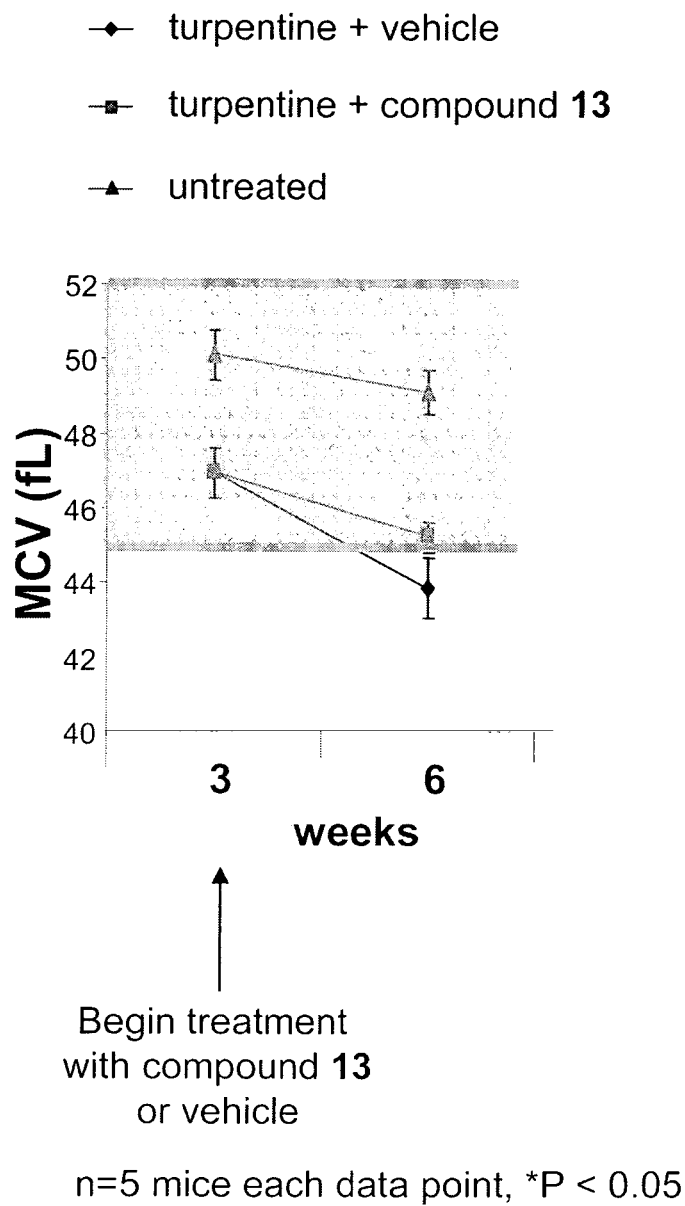
FIG. 19 shows a histogram indicating MCV levels in mice that were untreated, treated with turpentine and vehicle, or treated with turpentine and compound 13.
Figure 20:
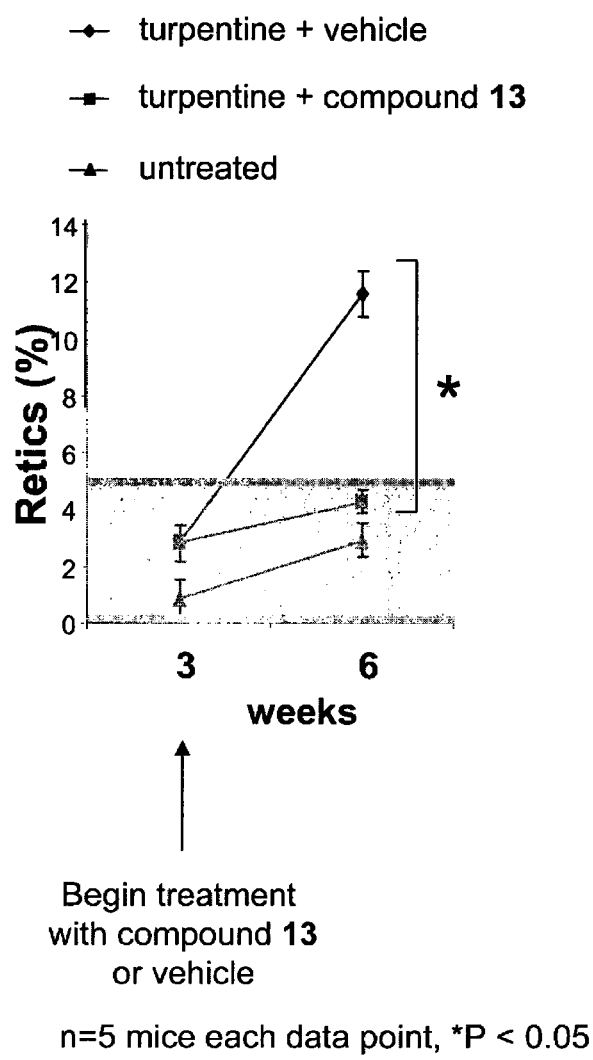
FIG. 20 shows a histogram indicating reticulocyte levels in mice that were untreated, treated with turpentine and vehicle, or treated with turpentine and compound 13.
Figure 21:
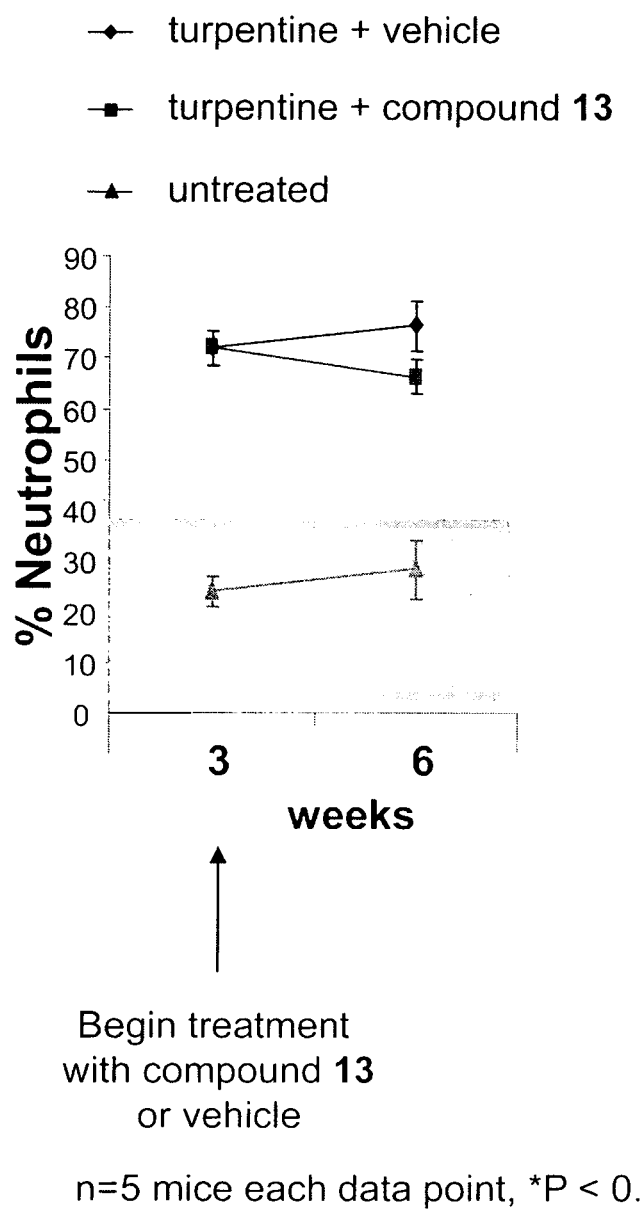
FIG. 21 shows a histogram indicating percent neutrophils levels in mice that were untreated, treated with turpentine and vehicle, or treated with turpentine and compound 13.

Compound 13 Normalizes Reticulocyte Count and MCV in Established Turpentine-Induced Anemia Turpentine-treated animals were found to have relative microcytosis after 3 weeks of turpentine injections. When mice are treated with vehicle for a subsequent 3 weeks of turpentine injections, mean corpuscular volume drops further to abnormal levels, while treatment with compound 13 (3 mg/kg/d IP) restores MCV to low-normal levels (FIG. 19). Treatment with turpentine for 6 continuous weeks results in elevation of reticulocyte counts in the circulation, whereas cotreatment for the final 3 weeks with compound 13 restores high-normal reticulocyte counts (FIG. 20). Turpentine injections induced neutrophilia regardless of treatment with vehicle or compound 13 (FIG. 21). Shaded areas indicate normative values in C57BL/6 mice for each parameter.

Example 25

Prevention of the Development of Vascular Calcification in Mice Deficient in Matrix GLA Protein The following describes an assay that may be used to determine whether BMP inhibitors can prevent the development of vascular calcification in mice deficient in matrix GLA protein (MGP). Wild-type and MGP knockout (MGP−/−) mice can be treated with vehicle or a BMP inhibitor beginning at one week of age. The effect of the drug can be determined at various timepoints (e.g., 7, 14, 21, 28, 35, and 42 days of treatment). Mice can be sacrificed and their aortas harvested for either histology (to evaluate vascular calcification) or for extraction and immunoblotting (to measure phosphorylation of SMAD1/5/8, a measure of BMP signaling). To assess the variability of the model and the efficacy of the treatment, a study can include 10 mice in each experimental group (5 for histology and 5 for immunoblot). Mice may be generated by breeding a pair of MGP+/− mice.

Beginning at 7 days of age (before the onset of vascular calcification in MGP−/− mice), wild-type and MGP−/− mice may receive twice daily an intraperitoneal injection of a BMP inhibitor or vehicle. The inhibitor may be dissolved in 2% (w/v) (2-hydroxypropyl)-β-cyclodextrin in phosphate-buffered saline (PBS), pH 7.4, and 3 mg/kg. After euthanasia, vascular tissues can be fixed in situ with 10% formalin. Tissue sections can be prepared for characterization of elastin (Verhoeff-van Giesen stain) and vascular calcium (von Kossa staining). To assess the efficacy of BMP inhibition, aortic tissues can be harvested without fixation and homogenized in lysis buffer. Protein extracts can be subjected to SDS gel electrophoresis, transferred to nitrocellulose membranes, and reacted with antibodies directed against phosphorylated SMAD1/5/8 and total SMAD1.

Example 26

Treatment Hair Loss

Hair growth is a complex process involving cycles of active hair growth (anagen), resting (telogen), and regression (catagen). Increasing evidence points to an important role for BMP signaling in the regulation of hair follicle growth. Importantly, BMP signaling appears to inhibit the transition from telogen to anagen. Increased expression of noggin, a protein which scavenges BMP ligands, appears to be required for induction of hair follicle growth.

Studies in transgenic mice over-expressing noggin in the skin (Plikus et al. *Nature* 451:340-344. 2008) and in mice in which noggin was injected subcutaneously (Botchkarev et al. *J. Invest. Dermatol.* 118:3-10, 2002) have demonstrated that BMP inhibition can augment hair follicle growth. As a treatment for hair loss, noggin administration has the disadvantage that large amounts of the protein must be administered parenterally. In contrast, small molecule BMP inhibitors may be developed for oral or topical administration.

The following describes an assay that may be used to determine whether inhibitors of bone morphogenetic protein (BMP) signaling can be used to treat hair loss caused by a variety of factors. Specifically, molecules may be tested to test their ability to speed hair regrowth after hair removal in adult mice. For example, five mice may be used for skin histology, and another five may be used to measure levels of BMP inhibitors and BMP signaling (SMAD1/5/8 phosphorylation on immunoblots) in skin tissues.

One group of mice can be studied before hair removal and a second group can be studied immediately after hair removal. Mice can be treated with a BMP inhibitor or its vehicle. Groups of 10 mice can be studied at different timepoints (e.g., 6, 12, and/or 18 days of treatment).

Mice may be treated with a commercial hair remover to induce a cycle of hair growth. At some point later (e.g., 5 days later), the skin color will begin to darken (reflecting early hair growth), and hair will grow back after three weeks. Mice may be treated with and without BMP inhibitor delivered via injection in the abdominal cavity (e.g., via twice daily injections). The ability of BMP inihibitors to cause hair to grow back quicker can then be measured.

In one example, a BMP inhibitor (3 mg/kg in PBS containing 2% cyclodextrin (wt/vol)) or vehicle alone can be administered ip twice daily beginning immediately after depilation. Hair regrowth can be evaluated grossly at 6, 12, and 18 days. Animals can be euthanized at these time points, and histological sections of the skin will be examined for follicle number and size. Skin tissues can also be used for measuring drug levels and SMAD1/5/8 phosphorylation (an index of BMP signaling). As controls, additional mice can be studied before and just after depilation.

Example 27

Compound 13 Prevents IL-6-Induced Increase in Hepcidin Expression

Figure 22:
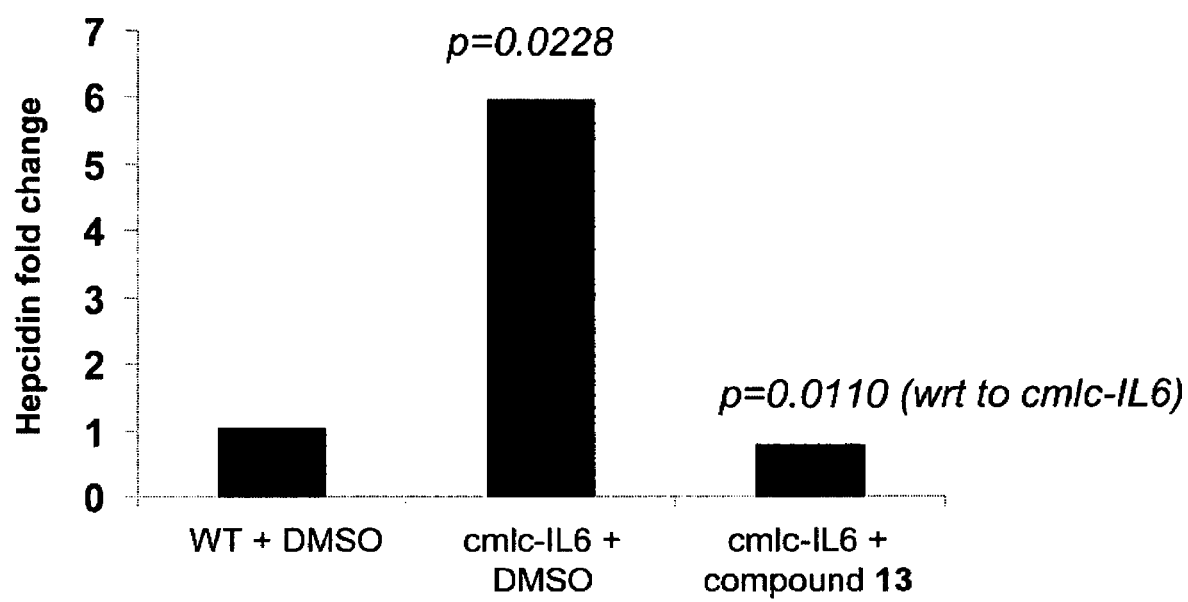
FIG. 22 shows a histogram indicating the relative levels of hepcidin expression in zebrafish that were untreated wild-types, untreated IL-6-expressing, or IL-6-expressing and treated with compound 13.

IL-6 expression was driven in the cardiomyocytes of living zebrafish by mating transgenic zebrafish expressing the Gal4 protein under the control of the cardiac myosin light chain 2 (cmlc) promoter with transgenic zebrafish carrying the human IL-6 gene under the control of a UAS upstream activation sequence (IL-6). Animals carrying both transgenes expressed IL-6 in their cardiomyocytes. IL-6-expressing animals were treated with 6 uM compound 13 or DMSO control by bathing overnight (FIG. 22). At 7 days postfertilization, animals were lysed, total RNA was extracted, and hepcidin expression levels were determined by quantitative RT-PCR with normalization to the housekeeping gene RPL13. Expression of IL-6 caused a 6-fold increase in hepcidin expression relative to wild-type controls. Treatment with compound 13 reduced hepcidin expression to wild-type levels in IL-6-expressing animals. These data suggest that compound 13 can prevent induction of hepcidin expression by the inflammatory cytokine IL-6.

Example 28

Modulation of Vascular Calcification by Inhibition of Bone Morphogenetic Protein Signaling Pharmacologic inhibition of BMP signaling with a selective inhibitor of BMP type I receptor activity, compound 13, can limit the progression of atheromatous plaques and vascular calcification in vivo. ApoE-deficient and LDL-receptor-deficient mice are predisposed to atherosclerotic and calcific vascular lesions, especially when fed high lipid diets (Bostrom et al. Crit Rev Eukaryot Gene Expr 10: 151-159. 2000). Therefore these mice have frequently been used to model atherosclerotic disease. Using these genetically-modified mice, the impact of compound 13 upon the development of spontaneous atherosclerotic and calcific lesions, as well as potentially the vascular remodeling that occurs with vessel injury (a model of restenosis after angioplasty and stent therapies) may be evaluated.

Figure 23:
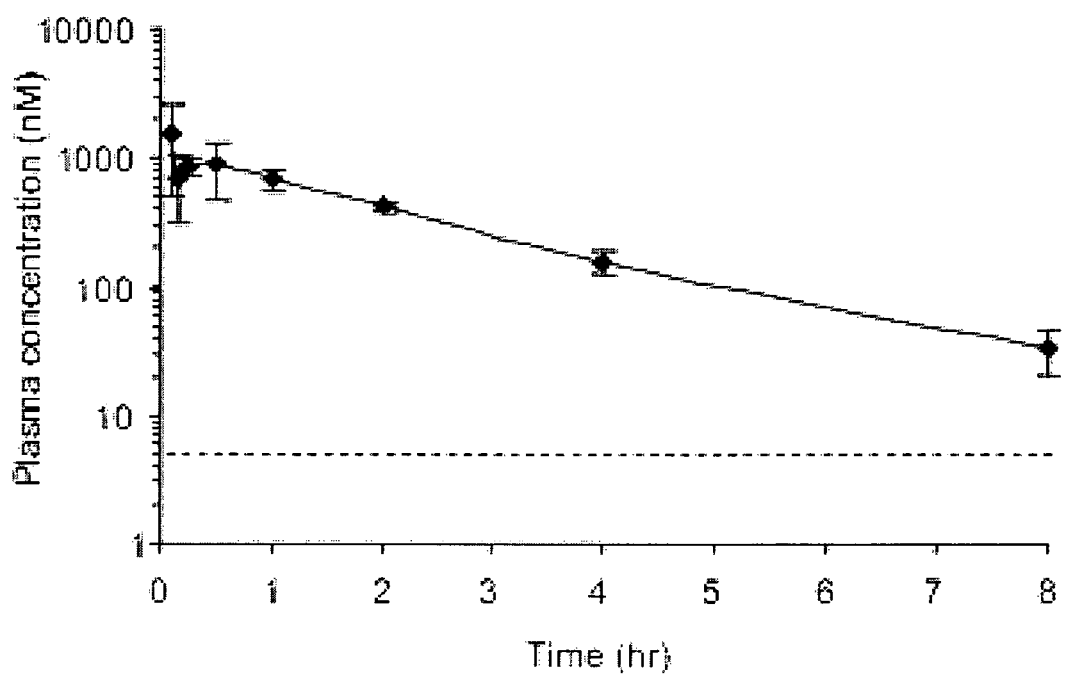
FIG. 23 shows a graph indicating the plasma pharmacokinetics of compound 13 after in mice

Preliminary pharmacokinetic studies were performed by intraperitoneally administering to wild-type mice (C57BL/6) one dose (3 mg/kg) of compound 13 (FIG. 23). Pharmacokinetics via plasma levels of compound 13 were serially measured in individual mice at varying intervals after injection by LC-MS/MS (n=3 mice each point, mean±s.d.). At 8 h following injection, plasma levels were 5-fold greater than the in vitro $IC_{50}$ of compound 13 for BMP4-mediated activation of Smad1/5/8 (indicated by the dashed line). These results suggest that sustained inhibition of BMP signaling can be obtained for >8 hours with a single IP injection of compound 13. Therefore, subsequent studies were performed with twice daily injections of compound 13 at 3 mg/kg intraperitoneally.

Adult (10 week old) LDL-R-deficient mice on a C57BL/6 background were subjected to a high-lipid atherogenic diet, concurrently with vehicle treatment or drug treatment (compound 13 mg/kg IP twice daily) started simultaneously with atherogenic diet. After 16 weeks of high fat diet and drug treatment, aortas, carotids, and left ventricular outflow tract were harvested and prepared as appropriate for histochemical staining or immunohistological staining, by en face mounting and fixation, or for paraffin embedded tissue sections for histology.

Figure 24:
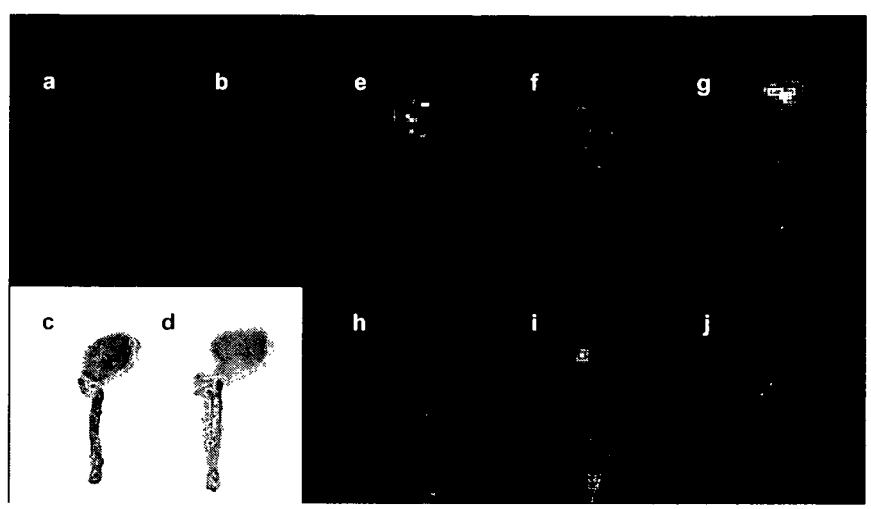
FIG. 24 shows images of aortas, as visualized by LICOR laser scanning after intravenous injection with Osteosense probe (VisEN), obtained from high-fat diet fed LDL-R-deficient mice treated with vehicel control (e, f, and g), high-fat diet fed LDL-R-deficient mice treated with compound 13 (h, i, and j), and wild-type mice given a normal diet (a, b). Non-fluorescent images of wild-type aortas are also depicted (c, d).

To analyze early osteogenesis (as a precursor to calcification), mice were injected intravenously with Osteosense probe (VisEn) 24 hours prior to harvest, and harvested aortas were rinsed with phosphate buffered saline. Visualization of Osteosense probe was accomplished by near-IR fluorescence (750 nM) using a LICOR laser scanner. This technique readily detected signal in aortas obtained from high-fat diet LDL-R-deficient mice treated with vehicle control (e, f, and g), while relatively little background signal was obtained in wild-type mice given a normal diet (a, b). Non-fluorescent imaging of wild-type aortas is also depicted (c, d). Aortas from high fat-fed LDL-R-deficient mice treated with compound 13 (h, i and j) exhibited fluorescence which was less intense than that of vehicle-treated controls, suggesting that inhibition of BMP signaling may be effective in modulating vascular calcification associated with atherosclerosis. These data are representative of data obtained in two independent experiments, utilizing 6 mice per treatment group (FIG. 24).

The invention claimed is:

1. A compound having a structure of Formula I:

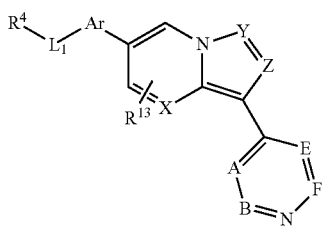

Formula I wherein
X and Y are each N;
Z is $CR^3$;
Ar is substituted or unsubstituted phenyl;
$L_1$ is absent or selected from substituted or unsubstituted alkyl and heteroalkyl;
A and B are both $CR^{16}$;
E and F are both $CR^5$ and both occurrences of $R^5$ taken together with E and F form a substituted or unsubstituted 5- or 6-membered cycloalkyl, heterocycloalkyl, aryl, or heteroaryl ring;
$R^3$ is selected from H and substituted or unsubstituted alkyl;
$R^4$ is selected from H and substituted or unsubstituted alkenyl, alkynyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido;
$R^{15}$, independently for each occurrence, is selected from H and substituted or unsubstituted alkyl, cycloalkyl, heterocyclyl, cycloalkylalkyl, heterocyclylalkyl, halogen, acylamino, carbamate, cyano, sulfonyl, sulfoxido, sulfamoyl, or sulfonamido;
$R^{16}$, independently for each occurrence, is absent or is selected from H and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido, or a pharmaceutically acceptable salt or ester thereof.

2. The compound of claim 1, wherein A and B are each CH.

3. The compound of claim 1 or 2, wherein both instances of $R^5$ taken together with E and F form a 6-membered ring.

4. The compound of claim 3, wherein E and F together represent the group

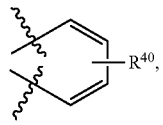

wherein $R^{40}$ is absent or represents from 1-4 substituents selected from substituted or unsubstituted alkyl, cycloalkyl, halogen, acylamino, carbamate, cyano, sulfonyl, sulfoxido, sulfamoyl, or sulfonamido.

5. The compound of claim 1 or 2, wherein $L_1$ has a structure

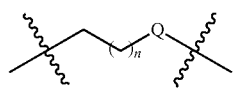

wherein
Q is selected from $CR^{10}R^{11}$, $NR^{12}$, O, S, S(O), and $SO_2$; and
$R^{10}$ and $R^{11}$, independently for each occurrence, are selected from H and substituted or unsubstituted alkyl, cycloalkyl, heterocyclyl, cycloalkylalkyl, heterocyclylalkyl, amino, acylamino, carbamate, amido, amidino, cyano, sulfonyl, sulfoxido, sulfamoyl, or sulfonamido;
$R^{12}$ selected from H and substituted or unsubstituted alkyl, cycloalkyl, heterocyclyl, heterocyclylalkyl, amino, acylamino, carbamate, amido, amidino, sulfonyl, sulfamoyl, or sulfonamido and
n is an integer from 0-4.

6. The compound of claim 1 or 2, wherein $R^4$ is selected from

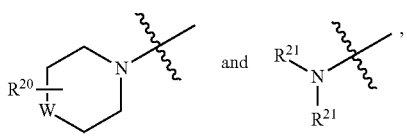

wherein
W is absent or is $C(R^{21})_2$, O, or $NR^{21}$;
$R^{20}$ is absent or is selected from substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfoxido, sulfamoyl, and sulfonamido; and
$R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamido.

7. The compound of claim 1 or 2, wherein $L_1$ is disposed on the para-position of Ar relative to the bicyclic core.

8. A pharmaceutical composition comprising a compound of claim 1 or 2 and a pharmaceutically acceptable excipient or solvent.

* * * * *

UNITED STATES PATENT AND TRADEMARK OFFICE
CERTIFICATE OF CORRECTION

PATENT NO.        : 8,507,501 B2
APPLICATION NO.   : 12/922122
DATED             : August 13, 2013
INVENTOR(S)       : Yu et al.

It is certified that error appears in the above-identified patent and that said Letters Patent is hereby corrected as shown below:

In the Claims:

At column 81, claim number 1, lines 6-13, please replace

"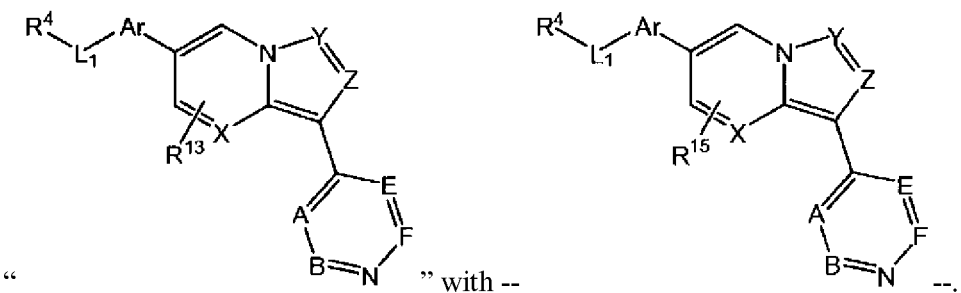" with --  --.

Signed and Sealed this
Twenty-second Day of October, 2013

Teresa Stanek Rea
*Deputy Director of the United States Patent and Trademark Office*